(12) United States Patent
Dell'Accio et al.

(10) Patent No.: US 11,730,755 B2
(45) Date of Patent: Aug. 22, 2023

(54) ROR2 INHIBITORS AND USE THEREOF IN TREATING AND/OR PREVENTING CARTILAGE LOSS

(71) Applicant: QUEEN MARY UNIVERSITY OF LONDON, London (GB)

(72) Inventors: Francesco Dell'Accio, London (GB); Anne-Sophie Thorup, London (GB)

(73) Assignee: Queen Mary University of London, London (GB)

(*) Notice: Subject to any disclaimer, the term of this patent is extended or adjusted under 35 U.S.C. 154(b) by 112 days.

(21) Appl. No.: 16/763,661

(22) PCT Filed: Nov. 16, 2018

(86) PCT No.: PCT/GB2018/053327
§ 371 (c)(1),
(2) Date: May 13, 2020

(87) PCT Pub. No.: WO2019/097247
PCT Pub. Date: May 23, 2019

(65) Prior Publication Data
US 2020/0360417 A1    Nov. 19, 2020

(30) Foreign Application Priority Data
Nov. 16, 2017 (GB) ..................................... 1718985

(51) Int. Cl.
| | | |
|---|---|---|
| *C07H 21/02* | (2006.01) | |
| *A61K 31/713* | (2006.01) | |
| *A61P 19/02* | (2006.01) | |
| *A61K 38/00* | (2006.01) | |
| *C12N 15/113* | (2010.01) | |
| *C12N 15/63* | (2006.01) | |
| *G01N 33/68* | (2006.01) | |

(52) U.S. Cl.
CPC .......... *A61K 31/713* (2013.01); *A61K 38/005* (2013.01); *A61P 19/02* (2018.01); *C12N 15/113* (2013.01); *C12N 15/63* (2013.01); *G01N 33/6803* (2013.01); *C12N 2310/14* (2013.01); *C12N 2310/531* (2013.01); *G01N 2800/105* (2013.01); *G01N 2800/50* (2013.01)

(58) Field of Classification Search
CPC .................... C12N 15/113; C12N 2310/14
See application file for complete search history.

(56) References Cited

U.S. PATENT DOCUMENTS

| | | |
|---|---|---|
| 6,908,744 B1 | 6/2005 | DeChiara et al. |
| 2005/0148506 A1 | 7/2005 | Billiard et al. |
| 2009/0047287 A1 | 2/2009 | Billiard et al. |
| 2009/0074742 A1 | 3/2009 | Kobayashi |
| 2009/0226463 A1 | 9/2009 | Billiard et al. |

FOREIGN PATENT DOCUMENTS

| | | | |
|---|---|---|---|
| WO | WO 01/068812 | 9/2001 | |
| WO | WO 2004/094641 A2 * | 11/2004 | ........... C12N 15/113 |
| WO | WO 2007/098198 | 8/2007 | |
| WO | WO 2007/098198 A2 * | 8/2007 | ........... C12N 15/113 |
| WO | WO 2013/103637 | 7/2013 | |
| WO | WO 2016/142768 | 9/2016 | |
| WO | WO 2017/127702 | 7/2017 | |

OTHER PUBLICATIONS

Elbashir et al. (The EMBO Journal, vol. 20, No. 23, pp. 6877-6888, 2001).*
Morioka et al. (Cancer Sci, 2009, 100, 7, 1227-1233).*
Afzal et al. "Recessive Robinow syndrome, allelic to dominant brachydactyly type B, is caused by mutation of ROR2," Nature Genetics, Aug. 2000, vol. 25, No. 4, pp. 419-422.
Al-Shawi et al. "Expression of the Ror1 and Ror2 receptor tyrosine kinase genes during mouse development," Development Genes and Evolution, Apr. 2001, vol. 211, No. 4, pp. 161-171.
Bokhoven et al. "Mutation of the gene encoding the ROR2 tyrosine kinase causes autosomal recessive Robinow syndrome," Nature Genetics, Aug. 2000, vol. 25, pp. 423-426.
Buckwalter et al. "The Impact of Osteoarthritis," Clinical Orthopaedics and Related Research, 2004, No. 427S, pp. S6-S15.
Castano Betancourt et al. "Genome-wide association and functional studies identify the DOT1L gene to be involved in cartilage thickness and hip osteoarthritis," PNAS, May 22, 2012, vol. 109, No. 21, pp. 8218-8223.
Clements et al. "Gene Deletion of Either Interleukin-1β, Interleukin-1β-Converting Enzyme, Inducible Nitric Oxide Synthase, or Stromelysin 1 Accelerates the Development of Knee Osteoarthritis in Mice After Surgical Transection of the Medial Collateral Ligament and Partial Medial Meniscectomy," Arthritis & Rheumatism, Dec. 2003, vol. 48, No. 12, pp. 3452-3463.
Dechiara et al. "Ror2, encoding a receptor-like tyrosine kinase, is required for cartilage and growth plate development," Nature Genetics, Mar. 2000, vol. 24, pp. 271-274.
Decker et al. "Genesis and morphogenesis of limb synovial joints and articular cartilage," Matrix Biology, Oct. 2014, vol. 39, pp. 5-10.
Dell'Accio et al. "Identification of the Molecular Response of Articular Cartilage to Injury, by Microarray Screening," Arthritis & Rheumatism, May 2008, vol. 58, No. 5, pp. 1410-1421.
Enomoto-Iwamoto et al. "The Wnt Antagonist Frzb-1 Regulates Chondrocyte Maturation and Long Bone Development during Limb Skeletogenesis," Developmental Biology, Nov. 2002, vol. 251, No. 1, pp. 142-156.
Forrester "The Ror receptor tyrosine kinase family," CMLS, Cellular and Molecular Life Sciences, 2002, vol. 59, pp. 83-96.
Gao et al. "Wnt Signaling Gradients Establish Planar Cell Polarity by Inducing Vangl2 Phosphorylation through Ror2," Developmental Cell, Feb. 2011, vol. 20, No. 2, pp. 163-176.

(Continued)

Primary Examiner — Amy H Bowman
(74) Attorney, Agent, or Firm — Sheridan Ross P.C.

(57) ABSTRACT

The present invention relates to anti-ROR2 inhibitors and uses thereof in treating and/or preventing cartilage loss.

1 Claim, 15 Drawing Sheets
Specification includes a Sequence Listing.

(56) References Cited

OTHER PUBLICATIONS

Glasson et al. "Deletion of active ADAMTS5 prevents cartilage degradation in a murine model of osteoarthritis," Nature, Mar. 2005, vol. 434, No. 7033, pp. 644-648.
Guo et al. "Wnt/β-catenin signaling is sufficient and necessary for synovial joint formation," Genes & Development, Oct. 2004, vol. 18, No. 19, pp. 2404-2417.
Hartmann et al. "Wnt-14 Plays a Pivotal Role in Inducing Synovial Joint Formation in the Developing Appendicular Skeleton," Cell, Feb. 2001, vol. 104, No. 3, pp. 341-351.
Hill et al. "Canonical Wnt/β-Catenin Signaling Prevents Osteoblasts from Differentiating into Chondrocytes," Developmental Cell, May 2005, vol. 8, No. 5, pp. 727-738.
Hooge et al. "Male IL-6 gene knock out mice developed more advanced osteoarthritis upon aging," Osteoarthritis and Cartilage, 2005, vol. 13, pp. 66-73.
Kerkhof et al. "Radiographic osteoarthritis at three joint sites and FRZB, LRP5, and LRP6 polymorphisms in two population-based cohorts," Osteoarthritis and Cartilage, 2008, vol. 16, pp. 1141-1149.
Kozhemyakina et al. "Identification of a Prg4-positive articular cartilage progenitor cell population," Arthritis & Rheumatology, May 2015, vol. 67, No. 5, pp. 1261-1273.
Liu et al. "The Orphan Receptor Tyrosine Kinase Ror2 Promotes Osteoblast Differentiation and Enhances ex Vivo Bone Formation," Molecular Endocrinology, 2007, vol. 21, No. 2, pp. 376-387.
Liu et al. "Wnt5a Induces Homodimerization and Activation of Ror2 Receptor Tyrosine Kinase," Journal of Cellular Biochemistry, 2008, vol. 105, pp. 497-502.
Lories et al. "Evidence for a differential association of the Arg200Trp single-nucleotide polymorphism in FRZB with hip osteoarthritis and osteoporosis," Rheumatology, Jan. 2006, vol. 45, No. 1, pp. 113-114.
Loughlin et al. "Functional variants within the secreted frizzled-related protein 3 gene are associated with hip osteoarthritis in females," PNAS, Jun. 29, 2004, vol. 101, No. 26, pp. 9757-9762.
Luyten et al. "Wnt signaling and osteoarthritis," Bone, 2009, vol. 44, pp. 522-527.
MacLauchlan et al. "Genetic deficiency of Wnt5a diminishes disease severity in a murine model of rheumatoid arthritis," Arthritis Research & Therapy, 2017, vol. 196, article 166, 11 pages.
Maeda et al. "Wnt5a-Ror2 signaling between osteoblast-lineage cells and osteoclast precursors enhances osteoclastogenesis," Nature Medicine, Mar. 2012, vol. 18, No. 3, pp. 405-412.
Nagase et al. "Aggrecanases and cartilage matrix degradation," Arthritis Research & Therapy, 2003, vol. 5, No. 2, pp. 94-103.
Oldridge et al. "Dominant mutations in ROR2, encoding an orphan receptor tyrosine kinase, cause brachydactyly type B," Nature Genetics, Mar. 2000, vol. 24, pp. 275-278.
Park et al. "Alternative Wnt Signaling Activates YAP/TAZ," Cell, Aug. 2015, vol. 162, pp. 780-794.
Saito et al. "Transcriptional regulation of endochondral ossification by HIF-2α during skeletal growth and osteoarthritis development," Nature Medicine, Jun. 2010, vol. 16, No. 6, pp. 678-686.
Schwabe et al. "Ror2 Knockout Mouse as a Model for the Developmental Pathology of Autosomal Recessive Robinow Syndrome," Developmental Dynamics, 2004, vol. 229, pp. 400-410.
Sen et al. "Expression and function of wingless and frizzled homologs in rheumatoid arthritis," PNAS, Mar. 2000, vol. 97, No. 6, pp. 2791-2796.
Sherwood et al. "The Role of CXCR2 Signalling in Articular Cartilage Homeostasis," Annals of the Rheumatic Diseases, Mar. 2013, vol. 72, Supplement 1, pp. A63-A64.
Sherwood et al. "Cellular and molecular mechanisms of cartilage damage and repair," Drug Discovery Today, Aug. 2014, vol. 19, No. 8, pp. 1172-1177.
Stanton et al. "ADAMTS5 is the major aggrecanase in mouse cartilage in vivo and in vitro," Nature, Mar. 2005, vol. 434, No. 7033, pp. 648-652.
Yamamoto et al. "Cthrc1 Selectively Activates the Planar Cell Polarity Pathway of Wnt Signaling by Stabilizing the Wnt-Receptor Complex," Developmental Cell, Jul. 2008, vol. 15, No. 1, pp. 23-36.
Yang et al. "Hypoxia-inducible factor-2α is a catabolic regulator of osteoarthritic cartilage destruction," Nature Medicine, Jun. 2010, vol. 16, No. 6, pp. 687-693.
Yang et al. "Wnt5a/Ror2 Mediates Temporomandibular Joint Subchondral Bone Remodeling," Journal of Dental Research, 2015, vol. 94, No. 6, pp. 803-812.
Dickinson et al. "The Wnt5a Receptor, Receptor Tyrosine Kinase-Like Orphan Receptor 2, Is a Predictive Cell Surface Marker of Human Mesenchymal Stem Cells with an Enhanced Capacity for Chondrogenic Differentiation: ROR2+ Mesenchymal Stem Cells for Cartilage Repair," Stem Cells, Aug. 2017, vol. 35, No. 11, pp. 2280-2291.
International Search Report and Written Opinion for International (PCT) Patent Application No. PCT/GB2018/053327, dated Apr. 1, 2019, 16 pages.

* cited by examiner

Ror2: Sham surgery

Ror2: DMM

IgG: DMM

Medial Tibia

ROR2 INHIBITORS AND USE THEREOF IN TREATING AND/OR PREVENTING CARTILAGE LOSS

CROSS REFERENCE TO RELATED APPLICATIONS

This application is a national stage application under 35 U.S.C. 371 and claims the benefit of PCT Application No. PCT/GB2018/053327 having an international filing date of 16 Nov. 2018, which designated the United States, which PCT application claimed the benefit of Great Britain Patent Application No. 1718985.3, filed 16 Nov. 2017, the disclosures of which are hereby incorporated by reference in their entireties.

REFERENCE TO SEQUENCE LISTING

This application contains a Sequence Listing submitted as an electronic text file named "Sequence_Listing.txt", having a size in bytes of 52000 bytes, and created on 16 Nov. 2017. The information contained in this electronic file is hereby incorporated by reference in its entirety pursuant to 37 CFR § 1.52(e)(5).

FIELD OF THE INVENTION

The present invention relates to the treatment and/or prevention of cartilage loss, such as the cartilage loss that occurs in osteoarthritis, chondral defects, osteochondral defects or trauma. Thus, the present invention relates to the treatment of osteoarthritis, and to the amelioration of one or more symptoms of osteoarthritis. The invention also relates to the promotion of cartilage repair, for example, by promoting new cartilage growth and differentiation and/or by reducing or preventing cartilage degradation. The present invention is directed to the use of inhibitors of ROR2, and in particular the use of anti-ROR2 antibodies or siRNA targeting ROR2 for the treatment of these conditions. The present invention also relates to the use of inhibitors of ROR2 in methods of enhancing the capacity of autologous cell preparations to produce cartilage in vivo. The present invention also relates to diagnostic and predictive methods for cartilage loss, osteoarthritis, osteoarthritis associated pain and/or cartilage degradation involving determining the expression level and/or the activity of ROR2.

BACKGROUND OF THE INVENTION

Osteoarthritis (OA) is a joint disease characterized by breakdown of the articular cartilage, the tissue that covers the ends of the long bones allowing frictionless joint motion and bone changes including thickening of the bone supporting the cartilage and excessive bone formation at the margins of the joint (osteophytes). OA affects up to ⅓ of the population over the age of 45 is the main cause of chronic disability worldwide and costs between 1 and 2% of the GDP in westernized countries. OA is usually caused by pathological, chronic mechanical injury, for instance excessive body weight, joint malalignment, or joint instability, such as lesions to ligaments and menisci Inflammation is sometimes present in OA joints as a consequence of tissue damage but does not drive disease progression and in fact mice lacking the gene encoding for the inflammatory cytokines IL-6 and IL-1 or the chemokine receptor CXCR2 are more susceptible to OA (Clements et al., 2003; Hooge et al., 2005; Sherwood et al., 2013).

In addition to osteoarthritis, cartilage loss is also the disabling outcome of inflammatory arthritis such as rheumatoid arthritis or psoriatic arthritis. In such conditions, even when with current anti-inflammatory therapies we manage to control inflammation, if cartilage damage has already occurred, patients will still experience symptoms such as joint pain and loss of mobility and joint damage will progress further, independently of inflammation, driven by the pathological biomechanics due to the initial cartilage loss.

Cartilage defects are found in 60% of all arthroscopic procedures, can be chronically painful and can lead to osteoarthritis. Current therapeutic approaches only result in only transient improvement as in the case of microfracture, or, in the case of autologous chondrocyte implantation, the autologous nature of the cell product impedes upscaling, implies complex surgery, and makes production costs unsuitable for routine application.

Cartilage regeneration is desirable to treat tracheomalacia, where, due to trauma or inflammation, the cartilage of the trachea collapses thereby impeding respiration. Cartilage regeneration can also be useful to reconstruct ears or nose after trauma, burns or inflammatory conditions that destroy this tissue.

Articular cartilage is an avascular tissue composed of chondrocytes, which secrete a large amount of glycosaminoglycan (GAG)-rich extracellular matrix composed mostly by the proteoglycan Aggrecan and collagen type II. In resting conditions cartilage has an extremely low turnover. After injury, however, homeostatic mechanisms are deployed including the upregulation of the cartilage transcription factor SOX-9 and of its transcriptional targets COL2A1 and ACAN (which encode for the main components of the cartilage extracellular matrix Collagen type II and Aggrecan). In favourable conditions, such responses restore cartilage integrity and compensate for the injurious stimuli (Buckwalter et al., 2004; Sherwood et al., 2014). If the injury is too severe and sustained (obesity, trauma, malalignment), or if, because of genetic factors or age, the homeostatic response is defective, cartilage loss prevails and progresses. Further cartilage loss is mediated by the activation of extracellular matrix-degrading enzymes such as matrix metalloproteinases (MMPs) and aggrecanases ADAMTS-4 and ADAMTS-5 (Nagase and Kashiwagi, 2003; Glasson et al., 2005; Stanton et al., 2005).

Many of the signals that trigger this homeostatic response to injury also play important roles in embryonic skeletal development (Dell'Accio et al., 2008a; Sherwood et al., 2014). WNT signalling in particular is essential for joint specification and development (Hartmann and Tabin, 2001; Guo et al., 2004) but also controls the differentiation and fate of skeletal progenitors by favouring osteogenic and blocking chondrogenic differentiation (Hill et al., 2005). WNTs are a family of 19 pleiotropic morphogens that, after binding to their receptors called Frizzled (FZD), signal through multiple pathways: the "canonical" β catenin-dependent pathway, and a number of less understood "non-canonical" pathways one of which, the planar cell polarity (PCP) pathway, involving the co-receptor ROR2 (Yamamoto et al., 2008; Gao et al., 2011). In the canonical pathway, the engagement of "canonical" WNTs (such as WNT1) with FZD receptors leads to dimerization of FZD with their co-receptors LRP-5 or LRP-6, accumulation of cytoplasmic β catenin, which then translocates to the nucleus, binds to TCF/LEF1 transcription factors and activates transcription of target genes. In the WNT PCP pathway, FZD engagement by "non canonical" WNTs such as WNT-5A leads to heterodimerization with the co-receptor ROR2 (a tyrosine kinase receptor), the phosphorylation of the intracellular molecule Vang12 and downstream events that are distinct from those driven by canonical WNT signalling (Gao et al., 2011).

WNT signalling has a double role in cartilage. In adult cartilage, the most superficial cell layer is composed of progenitor cells which supply chondrocytes throughout life (Kozhemyakina et al., 2015). Canonical WNT signalling maintains this progenitor population by preventing its precocious chondrocytic differentiation (Decker et al., 2014). In mature chondrocytes, however, canonical WNT signalling promotes a form of terminal differentiation called chondrocyte hypertrophy (Enomoto-Iwamoto et al., 2002). During skeletal development, chondrocyte hypertrophy precedes cartilage calcification and ultimately its replacement by bone. In physiological conditions, articular chondrocytes are resistant to hypertrophy. During OA, mechanical damage triggers ectopic chondrocyte hypertrophy, which in turn drives cartilage breakdown and OA progression (Saito et al., 2010; Yang et al., 2010). In keeping with this, allelic variants of genes associated with increased canonical WNT activation are associated with a higher risk of developing OA (Loughlin et al., 2004; Lories et al., 2006; Kerkhof et al., 2008; Luyten et al., 2009; Castaño Betancourt et al., 2012). Because of this double role of WNT signalling (one beneficial: maintain an essential progenitor population and one pathological), targeting canonical WNT signalling in OA has so far been disappointing.

The role of the WNT PCP pathway, mediated by ROR2, in skeletal biology is less well studied. During embryonic development, Ror2 was expressed mainly in the permanent cartilages including the anterior portion of the ribs and prospective articular cartilage, but also in the growth plate and other organs such as the dermis and the embryonic telencephalon (DeChiara et al., 2000; Al-shawi et al., 2001). Loss of ROR2 during development resulted in shorter long bones and delayed cartilage calcification, hypertrophy and endochondral bone formation (DeChiara et al., 2000). In humans, loss of ROR2 results in Robinow syndrome, which is a form of dwarfism and closely phenocopies the phenotype of ROR2 loss in mice (Afzal et al., 2000; Schwabe et al., 2004).

It has also been observed that cultured mesenchymal stem cells (MSCs) isolated from OA subjects expressed higher levels of ROR2 than MSCs isolated from healthy control individuals (Dickinson et al. 2017). In the same study it was found that the MSCs from OA subjects produced cartilage with higher levels of type II collagen as compared to the non-OA cells.

Thus, the role of ROR2 in adult cartilage and in the context of OA in particular is unclear.

In the clinic, OA is usually treated by managing the pain and inflammation associated with OA. For example, subjects with OA may be prescribed non-opioid analgesics, such as paracetamol, or non-steroidal anti-inflammatory drugs (NSAID). However, many OA subjects suffer from severe pain and inflammation and require treatment with steroids and/or opioid analgesics, such as codeine or tramadol, which are associated with numerous adverse effects including headaches, dizziness, drowsiness, tired feeling, constipation, diarrhoea, nausea, vomiting, and stomach pain amongst others. In some instances, subjects may become dependent on opioid analgesics with deleterious consequences. Eliminating pain does not restore joint integrity: in fact, the function of pain is to prevent over-use of an already compromised joint. Therefore, in clinical trials testing the efficacy of extremely potent pain killers such as blocking NGF/TRKA signalling resulted in very severe accelerated joint destruction in a subset of patients. Therefore pain control alone is not a suitable option with patients with cartilage loss. In addition, pain relief does not improve other disabling symptoms of osteoarthritis such as reduced joint mobility and muscle weakness.

Less common approaches for treating OA involve injecting an affected joint with either hyaluronic acid (believed to improve joint lubrication) or platelet rich plasma (PRP) which has a concentration of growth factors and cytokines and is proposed to stimulate localised healing. However, the clinical evidence for either of these treatment approaches is weak and efficacy has not thus far been convincingly demonstrated.

Accordingly, there remains a need for new and improved therapies for OA, particularly therapies that are able to promote cartilage repair and/or ameliorate the pain associated with OA.

SUMMARY OF THE INVENTION

The present invention is based, at least in part, on the surprising findings that (i) ROR2 is upregulated in cartilage following injury, (ii) ROR2 activity drives cartilage breakdown, (iii) ROR2 blockade improves the symptoms and structural outcomes of OA in mice, including sustained relief from OA associated pain and (iv) ROR2 blockade in human chondrocytes promotes human cartilage formation in vivo.

In this regard, the present inventors have demonstrated that ROR2 expression from the articular surface was lost postnatally and was reactivated by injury in adulthood. Further, in OA, ROR2 was found to be upregulated in cartilage as a result local inflammation and mechanical stress. ROR2 activation resulted in loss of cartilage extracellular matrix and chondrocytic differentiation. ROR2 blockade was sufficient for chondrogenic differentiation of the MC3H10T1/2 mesenchymal stem cell line, supported cartilage extracellular matrix production and suppressed the expression of the cartilage degrading enzymes ADAMTS-4 and -5.

Importantly, ROR2 silencing in therapeutic regime protected mice from instability-induced OA with improved structural outcome and sustained pain relief. Finally, ROR2 blockade improved differentiation and extracellular matrix production in human cartilage organoids in vivo after implantation in nude mice.

Thus, in one aspect the present invention provides a ROR2 inhibitor for use in treating and/or preventing cartilage loss and/or treating and/or preventing osteoarthritis, treating and/or preventing osteoarthritis associated pain, promoting cartilage repair, and/or preventing cartilage degradation, wherein the ROR2 inhibitor is selected from the group consisting of an oligonucleotide directed against ROR2, an anti-ROR2 antibody or fragment thereof, a soluble fragment of an ROR2 protein.

In one embodiment, the oligonucleotide of the invention is single stranded or double stranded.

In one embodiment, the oligonucleotide of the invention comprises DNA or RNA.

In one embodiment, the oligonucleotide of the invention is a short interfering RNA (siRNA).

In one embodiment, the oligonucleotide of the invention is a double stranded RNA (dsRNA).

In one embodiment, the oligonucleotide of the invention is a short hairpin RNA (shRNA).

In one embodiment, the shRNA of the invention comprises a polynucleotide sequence selected from the group consisting of:
(i) 5' GGUUCACGACUGCGAAUCCAGGACCUGGA 3' (SEQ ID NO: 15), a fragment comprising at least 10 contiguous nucleotides of SEQ ID NO: 15, and variants thereof having up to three nucleotide substitutions;
(ii) 5' AAGACCAUUACCGCCACUGGCGUCCUGUU 3' (SEQ ID NO: 16), a fragment comprising at least 10 contiguous nucleotides of SEQ ID NO: 16, and variants thereof having up to three nucleotide substitutions;
(iii) 5' AUGGAUUACAGAGGAACGGCAAGCAC-CAC 3' (SEQ ID NO: 17), a fragment comprising at least 10 contiguous nucleotides of SEQ ID NO: 17, and variants thereof having up to three nucleotide substitutions;
(iv) 5' AAGCAGAAGGCAUCUGCGUCCACACCGCA 3' (SEQ ID NO: 18), a fragment comprising at least 10 contiguous nucleotides of SEQ ID NO: 18, and variants thereof having up to three nucleotide substitutions;
(v) 5' CCUUGAGCAUGAUCUUCAGCUACUGUUCC 3' (SEQ ID NO: 19), a fragment comprising at least 10 contiguous nucleotides of SEQ ID NO: 19, and variants thereof having up to three nucleotide substitutions; and
(vi) nucleotide sequences complementary to any one of SEQ ID NOs:15-19, nucleotide sequences complementary to fragment comprising at least 10 contiguous nucleotides of SEQ ID NOs: 15-19, and variants thereof having up to three nucleotide substitutions.

In one embodiment, the oligonucleotide of the invention is a micro RNA (miRNA).

In one embodiment, the oligonucleotide of the invention is a guide RNA comprising a guide sequence that hybridises to site within an endogenous ROR2 gene and targets a CRISPR-Cas enzyme to said site.

In one embodiment, the oligonucleotide of the invention is 10-35 nucleotides in length.

In one embodiment, the oligonucleotide of the invention is an antisense oligonucleotide (AON).

In one embodiment, the siRNA of the invention comprises a nucleotide sequence selected from the group consisting of:
(i) 5' AAGUCUACAAAGGUCACCUGU 3' (SEQ ID NO: 1), a fragment comprising at least 10 contiguous nucleotides of SEQ ID NO: 1, and variants thereof having up to three nucleotide substitutions;
(iii) 5' AAGUCUACAAAGGUCACCUGUCCUGUCUC 3' (SEQ ID NO: 2) a fragment comprising at least 10 contiguous nucleotides of SEQ ID NO: 2, and variants thereof having up to three nucleotide substitutions;
(iii) 5' AAACAGGUGACCUUUGUAGAC 3' (SEQ ID NO: 3), a fragment comprising at least 10 contiguous nucleotides of SEQ ID NO: 3, and variants thereof having up to three nucleotide substitutions;
(iv) 5' AAACAGGUGACCUGUAGACCCUGUCUC 3' (SEQ ID NO: 4), a fragment comprising at least 10 contiguous nucleotides of SEQ ID NO: 4, and variants thereof having up to three nucleotide substitutions; and
(v) nucleotide sequences complementary to any one of SEQ ID NOs: 1-4, nucleotide sequences complementary to fragment comprising at least 10 contiguous nucleotides of SEQ ID NOs: 1-4, and variants thereof having up to three nucleotide substitutions.

In one embodiment, the siRNA of the invention comprises the sequences of:
(i) 5' AAGUCUACAAAGGUCACCUGU 3' (SEQ ID NO: 1), a fragment comprising at least 10 contiguous nucleotides of SEQ ID NO: 1, or a variant thereof having up to three nucleotide substitutions; and/or
(ii) 5' AAACAGGUGACCUUUGUAGAC 3' (SEQ ID NO: 3), a fragment comprising at least 10 contiguous nucleotides of SEQ ID NO: 3, or a variant thereof having up to three nucleotide substitutions.

In one embodiment, the siRNA is conjugated to a carrier or is encapsulated within an extracellular vesicle, a liposome or a dendrimer. The carrier may be selected from the group consisting of atelocollagen, a lipid such as cholesterol, a biological polymer, and a metallic nanoparticle such as a gold nanoparticle.

In one embodiment, the anti-ROR2 antibody is a blocking antibody.

In one embodiment, the anti-ROR2 antibody is: (a) an intact anti-ROR2 antibody; or (b) a fragment of an anti-ROR2 antibody selected from the group consisting of:
(i) a Fv fragment, optionally wherein the Fv fragment is a single chain Fv fragment or a disulphide-bonded Fv fragment; and
(ii) a Fab fragment; optionally wherein the Fab-like fragment is Fab' fragment or a F(ab')2 fragment.

In one embodiment, the anti-ROR2 antibody is a murine antibody, a chimeric antibody, a humanized antibody, or a human antibody.

In one embodiment, the anti-ROR2 antibody is a monoclonal antibody.

In one embodiment, the ROR2 inhibitor for use in treating and/or preventing cartilage loss and/or treating and/or preventing osteoarthritis, treating and/or preventing osteoarthritis associated pain, promoting cartilage repair, and/or preventing cartilage degradation is a soluble fragment of an ROR2 protein comprising all or a portion of an extracellular domain of an ROR2 protein.

The present invention also provides an ROR2 inhibitor which is a soluble fragment of an ROR2 protein comprising all or a portion of an extracellular domain of a ROR2 protein.

The extracellular domain may comprise a polypeptide having at least 50% identity to SEQ ID NO: 10. The soluble fragment of an ROR2 protein may further comprise a membrane anchor. The membrane anchor may be connected to the C-terminus of the extracellular domain. The membrane anchor may be connected to extracellular domain of the ROR2 protein by a linker. The membrane anchor may be a glycosylphosphatidylinositol (GPI) anchor.

The soluble fragment of the ROR2 protein further comprises an affinity tag. The affinity tag may be C-terminal to the extracellular domain or the membrane anchor. The affinity tag may be selected from the group consisting of a Myc/His tag, a Myc tag, a His tag, a glutathione S-transferase (GST) tag, a maltose binding protein (MBP) tag, a Strep tag II, a FLAG tag, an alkaline phosphatase tag, a bacteriophage T7 epitope tag (T7-tag), a calmodulin binding peptide (CBP) tag, a galactose binding protein (GBP) tag, a human influenza hemagglutinin (HA) tag, and combinations thereof.

The soluble fragment of the ROR2 protein further comprises a cleavage tag arranged to permit the affinity tag to be cleaved from the soluble fragment of the ROR2 protein. The cleavage tag may be C-terminal to the extracellular domain or the membrane anchor and N-terminal to the affinity tag. The cleavage tag may be selected from the group consisting of a enterokinase cleavage tag, a tobacco etch virus protease cleavage site, a thrombin cleavage tag, a factor Xa (FXa) cleavage tag, a human rhinovirus (HRV) 3C Protease ('PreScission') cleavage tag, and combinations thereof.

In another aspect, the present invention provides short interfering RNA (siRNA) directed against ROR2, wherein the siRNA comprises a sequence selected from the group consisting of:
(i) 5' AAGUCUACAAAGGUCACCUGU 3' (SEQ ID NO: 1), a fragment comprising at least 10 contiguous nucleotides of SEQ ID NO: 1, and variants thereof having up to three nucleotide substitutions;
(iii) 5' AAGUCUACAAAGGUCACCUGUCCUGUCUC 3' (SEQ ID NO: 2) a fragment comprising at least 10 contiguous nucleotides of SEQ ID NO: 2, and variants thereof having up to three nucleotide substitutions;
(iii) 5' AAACAGGUGACCUUUGUAGAC 3' (SEQ ID NO: 3), a fragment comprising at least 10 contiguous nucleotides of SEQ ID NO: 3, and variants thereof having up to three nucleotide substitutions;
(iv) 5' AAACAGGUGACCUGUAGACCCUGUCUC 3' (SEQ ID NO: 4), a fragment comprising at least 10 contiguous nucleotides of SEQ ID NO: 4, and variants thereof having up to three nucleotide substitutions; and
(v) nucleotide sequences complementary to any one of SEQ ID NOs:1-4, nucleotide sequences complementary to fragment comprising at least 10 contiguous nucleotides of SEQ ID NOs: 1-4, and variants thereof having up to three nucleotide substitutions.

In one embodiment, the siRNA of the invention comprises the sequences:
(i) 5' AAGUCUACAAAGGUCACCUGU 3' (SEQ ID NO: 1), a fragment comprising at least 10 contiguous nucleotides of SEQ ID NO: 1, or a variant thereof having up to three nucleotide substitutions; and/or
(ii) 5' AAACAGGUGACCUUUGUAGAC 3' (SEQ ID NO: 3), a fragment comprising at least 10 contiguous nucleotides of SEQ ID NO: 3, or a variant thereof having up to three nucleotide substitutions.

In one embodiment, the siRNA of the invention is 10-35 nucleotides in length.

In another aspect, the present invention provides an siRNA of the present invention for use as a medicament.

In another aspect, the present invention provides a soluble ROR2 protein comprising an extracellular domain of an ROR2 protein of the present invention for use as a medicament.

In another aspect, the present invention provides an siRNA of the invention for use in treating and/or preventing cartilage loss and/or treating and/or preventing osteoarthritis, treating and/or preventing osteoarthritis associated pain, promoting cartilage repair, and/or preventing cartilage degradation.

An siRNA of the invention may be conjugated to a carrier or encapsulated within a liposome. The carrier may be selected from the group consisting of atelocollagen, a lipid such as cholesterol, a biological polymer, and a metallic nanoparticle such as a gold nanoparticle.

In another aspect, the present invention provides a vector comprising a nucleotide sequence encoding an ROR2 inhibitor as defined herein or a siRNA of the invention. The vector may be selected from the group consisting of a lentiviral vector, a retroviral vector, and adeno-associated viral (AAV) vector.

In another aspect, the present invention provides an isolated cell comprising a vector according of the invention.

In another aspect, the present invention provides a pharmaceutical composition comprising an ROR2 inhibitor as defined herein, an siRNA of the invention, a vector of the invention, or an isolated cell of the invention, together with a pharmaceutically acceptable carrier or excipient.

In another aspect, the present invention provides an isolated cell of the invention or a pharmaceutical composition of the invention for use as a medicament.

In another aspect, the present invention provides an isolated cell of the invention or a pharmaceutical composition of the invention for use in treating and/or preventing cartilage loss and/or treating and/or preventing osteoarthritis, treating and/or preventing osteoarthritis associated pain, promoting cartilage repair, and/or preventing cartilage degradation.

In another aspect, the present invention provides a method of treating and/or preventing cartilage loss and/or treating and/or preventing osteoarthritis, treating and/or preventing osteoarthritis associated pain, promoting cartilage repair, and/or preventing cartilage degradation, the method comprising administering to an individual in need thereof a ROR2 inhibitor as defined herein, a siRNA of the invention, a vector of the invention, an isolated cell of the invention or a pharmaceutical composition of the invention.

In one embodiment of the method of the invention, administration of the ROR2 inhibitor, the siRNA, vector, the isolated cell or the pharmaceutical composition promotes cartilage repair.

In one embodiment, the method of the invention ameliorates one or more symptoms of osteoarthritis.

In one embodiment of the method of the invention, the ROR2 inhibitor, the siRNA, the vector, the isolated cell or the pharmaceutical composition inhibitor reduces osteoarthritis associated pain.

In another aspect, the present invention provides the use of an ROR2 inhibitor as defined herein, an siRNA of the present invention, a vector according of the present invention, an isolated cell of the present invention or a pharmaceutical composition of the present invention for manufacture of a medicament for treating and/or preventing cartilage loss and/or treating and/or preventing osteoarthritis, treating and/or preventing osteoarthritis associated pain, promoting cartilage repair, and/or preventing cartilage degradation.

In another aspect, the present invention provides a kit comprising an siRNA of the invention together with one or more carriers, and optionally instructions for conjugating the siRNA to the carrier, optionally wherein the carrier is selected from the group consisting of atelocollagen, a lipid such as cholesterol, a biological polymer, and a metallic nanoparticle such as a gold nanoparticle.

In another aspect, the present invention provides a method of diagnosing a subject with cartilage loss, osteoarthritis, osteoarthritis associated pain and/or cartilage degradation or a method for predicting that a subject has increased susceptibility to cartilage loss, osteoarthritis, osteoarthritis associated pain and/or cartilage comprising the step of:
(i) determining the expression level and/or the activity of ROR2 in a sample previously obtained from the subject.

In one embodiment, the diagnostic or predictive method of the invention further comprises the step of:
(ii) comparing the expression level and/or the activity of ROR2 determined in step (i) to one or more reference values.

In one embodiment, the one or more reference value is selected the expression level and/or activity of ROR2 in a sample obtained from a healthy control subject. The healthy control subject may have been previously determined not to exhibit cartilage loss, osteoarthritis, osteoarthritis associated pain and/or cartilage degradation. In one embodiment, the one or more reference values may have been previously determined. In one embodiment, the one or more reference values are stored on a computer readable medium.

In one embodiment, the diagnostic or predictive method of the invention further comprises the step of administering to the subject an ROR2 inhibitor. The ROR2 inhibitor may be selected from the group consisting of an oligonucleotide directed against ROR2, an anti-ROR2 antibody or fragment thereof, a soluble fragment of an ROR2 protein. In one embodiment, the diagnostic or predictive method of the invention further comprises the step of administering to the subject an ROR2 inhibitor of the invention, an siRNA directed against ROR2 of the invention, a vector of the invention, an isolated cell of the invention and/or a pharmaceutical composition of the invention.

In the diagnostic or predictive methods of the present invention, the subject may be diagnosed with cartilage loss, osteoarthritis, osteoarthritis associated pain and/or cartilage degradation or the subject is predicted to have increased susceptibility to cartilage loss, osteoarthritis, osteoarthritis associated pain and/or cartilage degradation if the expression level and/or activity level of ROR2 is at least 5%, 10%, 15%, 20%, 25%, 30%, 35%, 40%, 45%, 50%, 55%, 60%, 65%, 70%, 75%, 80%, 85%, 90%, 95%, or 100% higher than the one or more reference values; or the subject may be diagnosed with cartilage loss, osteoarthritis, osteoarthritis associated pain and/or cartilage degradation or the subject is predicted to have increased susceptibility to cartilage loss, osteoarthritis, osteoarthritis associated pain and/or cartilage degradation if the expression level and/or activity level of ROR2 is at least 1.5-fold, 2.0-fold, 2.5-fold, 3.0-fold, 3.5-fold, 4.0-fold, 5.0-fold, 10-fold, 20-fold, 50-fold, 100-fold or 1000-fold higher than the one or more reference values.

In the diagnostic or predictive methods of the present invention, the ROR2 activity determined in step (i) may be selected from:
(a) ROR2 induced inhibition of Wnt-β-catenin signalling;
(b) ROR2 tyrosine phosphorylation;
(c) phosphorylation of one or more ROR2 downstream targets, optionally wherein the ROR2 downstream target is 14-3-3beta scaffold protein;
(d) expression of one or more ROR2 target genes, optionally wherein the ROR2 target genes are selected from the group consisting of Ctgf, Yap, Taz and Wnt5a;
(e) the capacity of ROR2 to form a receptor complex; and
(f) combinations of any of (a) to (e).

In one embodiment, the diagnostic or predictive method of the invention further comprise determining the expression levels of one or more ROR2 target genes. The ROR2 target genes may be selected from the group consisting of Ctgf, Yap, Taz and Wnt5a.

In the diagnostic or predictive methods of the present invention the sample may be a peripheral blood sample, a cartilage tissue sample, a synovial sample or an intra-articular sample.

Any of the diagnostic or predictive methods of the present invention may be performed ex-vivo or in vitro on samples previously obtained from the subject. Thus, in one embodiment, the diagnostic or predictive method of the present invention is an ex-vivo method or an in vitro method.

DETAILED DESCRIPTION OF THE INVENTION

Figure 1A:
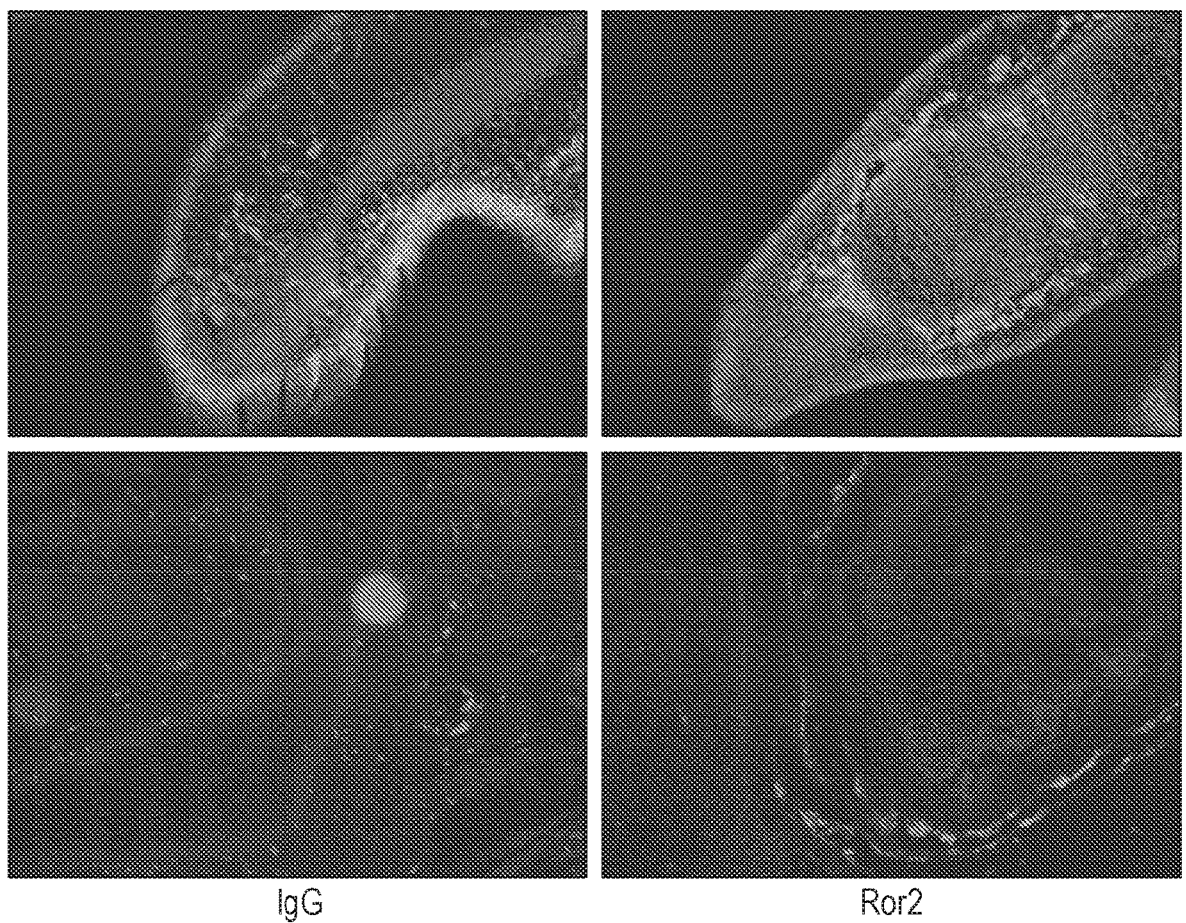
FIG. 1. ROR2 is not detectable in normal cartilage and is upregulated in osteoarthritis. (A) Detection of ROR2 in most superficial cartilage layer of the articular cartilage in mouse embryos at stage 18.5 days post coitum (dpc). (B) Detection of ROR2 in postnatal mice one week after inducing osteoarthritis by surgical destabilization of the medial meniscus (DMM). (C) Detection of ROR2 expression in human articular cartilage. (D) Western blot confirming ROR2 expression in human cartilage and synovial membrane.

The term "comprises" (comprise, comprising) should be understood to have its normal meaning in the art, i.e. that the stated feature or group of features is included, but that the term does not exclude any other stated feature or group of features from also being present. The term "consists of" should also be understood to have its normal meaning in the art, i.e. that the stated feature or group of features is included, to the exclusion of further features. For every embodiment in which "comprises" or "comprising" is used, the present invention provides a further embodiment in which "consists of" or "consisting of" is used. Thus, every disclosure of "comprises" should be considered to be a disclosure of "consists of".

ROR2

ROR-family receptor tyrosine kinases form a small sub-family of receptor tyrosine kinases (RTKs), characterized by a conserved, unique domain architecture. ROR RTKs are evolutionary conserved throughout the animal kingdom and act as alternative receptors and co-receptors for Wnt ligands.

The Ror2 gene encodes Receptor Tyrosine Kinase Like Orphan Receptor (ROR2), tyrosine kinase and type I trans-membrane protein, which is also known as Tyrosine-Protein Kinase Transmembrane Receptor ROR2, Neurotrophic Tyrosine Kinase Receptor-Related 2 (NTRKR2).

In humans, mutations in the ROR2 gene cause two distinct developmental syndromes, recessive Robinow syndrome (RRS; MIM 268310) and dominant brachydactyly type B1 (BDB1; MIM 113000).

ROR2 proteins are integral membrane protein comprising an extracellular portion, a transmembrane domain and an intracellular portion. The terms "extracellular portion of an ROR2 protein" and "extracellular domain of an ROR2 protein" may be used interchangeably herein. The extracellular portion/domain of an ROR2 protein may also be referred to as the "ECD" of an ROR2 protein. Typically, the extracellular portion of ROR2 comprises, from the N-terminus: a signal peptide, an immunoglobulin (Ig) domain, a cysteine rich domain (CRD) and a Kringle domain. C-terminal to the Kringle domain is a transmembrane domain followed by the intracellular portion. The intracellular portion of ROR2 typically comprises, from the N-terminus: a tyrosine kinase domain, a first serine/threonine (Ser/Thr) rich domain, a proline rich domain and a second Ser/Thr rich domain. Each of the Ig domain, CRD and the Kringle domain of the extracellular portion are likely to mediate protein-protein interactions, for example interactions with activating ligands of ROR2, such as Wnt family members. In particular, the CRD is known to bind activating ligands of the Wnt family.

An example human ROR2 protein has the amino acid sequence:

(SEQ ID NO: 5)
MARGSALPRRPLLCIPAVWAAAALLLSVSRTSGEVEVLDPNDPLGPLDGQ
DGPIPTLKGYFLNFLEPVNNITIVQGQTAILHCKVAGNPPPNVRWLKNDA
PVVQEPRRIIIRKTEYGSRLRIQDLDTTDTGYYQCVATNGMKTITATGVL
FVRLGPTHSPNHNFQDDYHEDGFCQPYRGIACARFIGNRTIYVDSLQMQG
EIENRITAAFTMIGTSTHLSDQCSQFAIPSFCHFVFPLCDARSRAPKPRE
LCRDECEVLESDLCRQEYTIARSNPLILMRLQLPKCEALPMPESPDAANC
MRIGIPAERLGRYHQCYNGSGMDYRGTASTTKSGHQCQPWALQHPHSHHL
SSTDFPELGGGHAYCRNPGGQMEGPWCFTQNKNVRMELCDVPSCSPRDSS
KMGILYILVPSIAIPLVIACLFFLVCMCRNKQKASASTPQRRQLMASPSQ
DMEMPLINQHKQAKLKEISLSAVRFMEELGEDRFGKVYKGHLFGPAPGEQ
TQAVAIKTLKDKAEGPLREEFRHEAMLRARLQHPNVVCLLGVVTKDQPLS
MIFSYCSHGDLHEFLVMRSPHSDVGSTDDDRTVKSALEPPDFVHLVAQIA
AGMEYLSSHHVVHKDLATRNVLVYDKLNVKISDLGLFREVYAADYYKLLG
NSLLPIRWMAPEAIMYGKFSIDSDIWSYGVVLWEVFSYGLQPYCGYSNQD
VVEMIRNRQVLPCPDDCPAWVYALMIECWNEFPSRRPRFKDIHSRLRAWG
NLSNYNSSAQTSGASNTTQTSSLSTSPVSNVSNARYVGPKQKAPPFPQPQ
FIPMKGQIRPMVPPPQLYIPVNGYQPVPAYGAYLPNFYPVQIPMQMAPQQ
VPPQMVPKPSSHHSGSGSTSTGYVTTAPSNTSMADRAALLSEGADDTQNA
PEDGAQSTVQEAEEEEEGSVPETELLGDCDTLQVDEAQVQLEA

Within the amino acid sequence of SEQ ID NO: 5, the following amino acid residues correspond to the domains of ROR2 as shown in Table 1 below.

| Portion | Domain | First amino acid residue | Last amino acid residue |
|---|---|---|---|
| Extracellular | Ig | 74 | 141 |
| | CRD | 174 | 299 |
| | Kringle | 316 | 394 |
| | Transmembrane | 407 | 428 |
| Intracellular | Tyrosine kinase | 473 | 746 |
| | First Ser/Thr rich | 748 | 782 |
| | Proline rich | 783 | 857 |
| | Second Ser/Thr rich | 858 | 882 |

An example human cDNA encoding ROR2 has the nucleotide sequence:

(SEQ ID NO: 6)
ggacgcatcgtagaaaggggtggtggcgcccgaccccgcgcccggcccgaagctctgagg gcttcccggcccccactgcctgcggcatggcccggggctcggcgctcccgcggcggccgct gctgtgcatcccggccgtctggcggccgccgcgcttctgctctcagtgtcccggacttca ggtgaagtggaggttctggatccgaacgacccctttaggacccct tgatgggcaggacggcc cgattccaactctgaaaggttactttctgaattttctggagccagtaaacaatatcaccat tgtccaaggccagacggcaattctgcactgcaaggtggcaggaaacccaccccctaacgtg cggtggctaaagaatgatgccccggtggtgcaggagccgcggcggatcatcatccggaaga -continued

```
cagaatatggttcacgactgcgaatccaggacctggacacgacagacactggctactacca gtgcgtggccaccaacgggatgaagaccattaccgccactggcgtcctgtttgtgcggctg ggtccaacgcacagcccaaatcataactttcaggatgattaccacgaggatgggttctgcc agccttaccggggaattgcctgtgcacgcttcattggcaaccggaccatttatgtggactc gcttcagatgcaggggggagattgaaaaccgaatcacagcggccttcaccatgatcggcacg tctacgcacctgtcggaccagtgctcacagttcgccatccatccttctgccacttcgtgt ttcctctgtgcgacgcgcgctcccgggcacccaagccgcgtgagctgtgccgcgacgagtg cgaggtgctggagagcgacctgtgccgccaggagtacaccatcgcccgctccaacccgctc atcctcatgcggcttcagctgcccaagtgtgaggcgctgccatgcctgagagccccgacg ctgccaactgcatgcgcattggcatcccagccgagaggctgggccgctaccatcagtgcta taacggctcaggcatggattacagaggaacggcaagcaccaccaagtcaggccaccagtgc cagccgtgggccctgcagcaccccacagccaccacctgtccagcacagacttccctgagc ttggagggggcacgcctactgccggaaccccggaggccagatggagggccctggtgctt tacgcagaataaaaacgtacgcatggaactgtgtgacgtaccctcgtgtagtccccgagac agcagcaagatggggattctgtacatcttggtccccagcatcgcaattccactggtcatcg cttgccttttcttcttggtttgcatgtgccggaataagcagaaggcatctgcgtccacacc gcagcggcgacagctgatggcctcgcccagccaagacatggaaatgcccctcattaaccag cacaaacaggccaaactcaaagagatcagcctgtctgcggtgaggttcatggaggagctgg gagaggaccggtttgggaaagtctacaaaggtcacctgttcggccctgccccggggagca gacccaggctgtggccatcaaaacgctgaaggacaaagcggaggggcccctgcgggaggag ttccggcatgaggctatgctgcgagcacggctgcaacaccccaacgtcgtctgcctgctgg gcgtggtgaccaaggaccagcccctgagcatgatcttcagctactgttcgcacggcgacct ccacgaattcctggtcatgcgctcgccgcactcggacgtgggcagcaccgatgatgaccgc acggtgaagtccgccctggagccccccgacttcgtgcaccttgtggcacagatcgcggcgg ggatggagtacctatccagccaccacgtggttcacaaggacctggccacccgcaatgtgct agtgtacgacaagctgaacgtgaagatctcagacttgggcctcttccgagaggtgtatgcc gccgattactacaagctgctggggaactcgctgctgcctatccgctggatggccccagagg ccatcatgtacggcaagttctccatcgactcagacatctggtcctacggtgtggtcctgtg ggaggtcttcagctacggcctgcagccctactgcgggtattccaaccaggatgtggtggag atgatccggaaccggcaggtgctgccttgccccgatgactgtcccgcctgggtgtatgccc tcatgatcgagtgctggaacgagttccccagccggcggcccgcttcaaggacatccacag ccggctccgagcctggggcaaccttccaactacaacagctcggcgcagacctcggggggcc agcaacaccacgcagaccagctccctgagcaccagcccagtgagcaatgtgagcaacgccc gctacgtggggcccaagcagaaggcccgcgccttcccacagccccagttcatccccatgaa gggccagatcagacccatggtgcccccgccgcagctctacatccccgtcaacggctaccag ccggtgccggcctatgggcctacctgcccaacttctacccggtgcagatcccaatgcaga tggccccgcagcaggtgcctcctcagatggtcccaagcccagctcacaccacagtggcag tggctccaccagcacaggctacgtcaccacggcccccctccaacacatccatggcagacagg gcagccctgctctcagagggcgctgatgacacacagaacgcccagaagatggggcccaga gcaccgtgcaggaagcagaggaggaggaggaaggctctgtcccagagactgagctgctggg ggactgtgacactctgcaggtggacgaggcccaagtccagctggaagcttgagtggcacca
```

-continued

```
gggcccagggttcggggatagaagcccgccgagacccacagggacctcagtcacctttg agaagacaccatactcagcaatcacaagagcccgccggccagtgggcttgtttgcagactg ggtgaggtggagccctgctcctctctgtcctctgacacagctgccctgcctaggagcaccc aagccaggcaggggtctggcagcacggcgtcctggggagcaggacacatggtcatcccca gggctgtatacattgattctggtggtagactggtagtgagcagcaaatgcctttcaagaaa ataggtggcagcttcactccatgtcatatatggagtgaatatttcaaaacgttgggaataa gggcctgcaaaaggca
```

The extracellular portion of an example human ROR2 protein has the amino acid sequence:

(SEQ ID NO: 10)
MARGSALPRRPLLCIPAVWAAAALLLSVSRTSGEVEVLDPNDPLGP

LDGQDGPIPTLKGYFLNFLEPVNNITIVQGQTAILHCKVAGNPPPN

VRWLKNDAPVVQEPRRIIIRKTEYGSRLRIQDLDTTDTGYYQCVAT

NGMKTITATGVLFVRLGPTHSPNHNFQDDYHEDGFCQPYRGIACAR

FIGNRTIYVDSLQMQGEIENRITAAFTMIGTSTHLSDQCSQFAIPS

FCHFVFPLCDARSRAPKPRELCRDECEVLESDLCRQEYTIARSNPL

ILMRLQLPKCEALPMPESPDAANCMRIGIPAERLGRYHQCYNGSGM

DYRGTASTTKSGHQCQPWALQHPHSHHLSSTDFPELGGGHAYCRNP

GGQMEGPWCFTQNKNVRMELCDVPSCSPRDSSKMGILY

The ROR2 extracellular portion of SEQ ID NO: 10 may be encoded by the nucleotide sequence:

(SEQ ID NO: 11)
ATGGCCCGGGGCTCGGCGCTCCCGCGGCGGCCGCTGCTGTGCATCC

CGGCCGTCTGGGCGGCCGCCGCGCTTCTGCTCTCAGTGTCCCGGAC

TTCAGGTGAAGTGGAGGTTCTGGATCCGAACGACCCTTTAGGACCC

CTTGATGGGCAGGACGGCCCGATTCCAACTCTGAAAGGTTACTTTC

TGAATTTTCTGGAGCCAGTAAACAATATCACCATTGTCCAAGGCCA

GACGGCAATTCTGCACTGCAAGGTGGCAGGAAACCCACCCCCTAAC

GTGCGGTGGCTAAAGAATGATGCCCCGGTGGTGCAGGAGCCGCGGC

GGATCATCATCCGGAAGACAGAATATGGTTCACGACTGCGAATCCA

GGACCTGGACACGACAGACACTGGCTACTACCAGTGCGTGGCCACC

AACGGGATGAAGACCATTACCGCCACTGGCGTCCTGTTTGTGCGGC

TGGGTCCAACGCACAGCCCAAATCATAACTTTCAGGATGATTACCA

CGAGGATGGGTTCTGCCAGCCTTACCGGGGAATTGCCTGTGCACGC

TTCATTGGCAACCGGACCATTTATGTGGACTCGCTTCAGATGCAGG

GGGAGATTGAAAACCGAATCACAGCGGCCTTCACCATGATCGGCAC

GTCTACGCACCTGTCGGACCAGTGCTCACAGTTCGCCATCCCATCC

TTCTGCCACTTCGTGTTTCCTCTGTGCGACGCGCGCTCCCGGGCAC

CCAAGCCGCGTGAGCTGTGCCGCGACGAGTGCGAGGTGCTGGAGAG

CGACCTGTGCCGCCAGGAGTACACCATCGCCCGCTCCAACCCGCTC
```

```
ATCCTCATGCGGCTTCAGCTGCCCAAGTGTGAGGCGCTGCCCATGC

CTGAGAGCCCCGACGCTGCCAACTGCATGCGCATTGGCATCCCAGC

CGAGAGGCTGGGCCGCTACCATCAGTGCTATAACGGCTCAGGCATG

GATTACAGAGGAACGGCAAGCACCACCAAGTCAGGCCACCAGTGCC

AGCCGTGGGCCCTGCAGCACCCCCACAGCCACCACCTGTCCAGCAC

AGACTTCCCTGAGCTTGGAGGGGGGCACGCCTACTGCCGGAACCCC

GGAGGCCAGATGGAGGGCCCCTGGTGCTTTACGCAGAATAAAAACG

TACGCATGGAACTGTGTGACGTACCCTCGTGTAGTCCCCGAGACAG

CAGCAAGATGGGGATTCTGTAC
```

The CRD of an example human ROR2 protein has the amino acid sequence:

(SEQ ID NO: 12)
CQPYRGIACARFIGNRTIYVDSLQMQGEIENRITAAFTMIGTSTHL

SDQCSQFAIPSFCHFVFPLCDARSRAPKPRELCRDECEVLESDLCR

QEYTIARSNPLILMRLQLPKCEALPMPESPDAAN

The CRD domain of SEQ ID NO: 12 may be encoded by the nucleotide sequence:

(SEQ ID NO: 13)
CTGCCAGCCTTACCGGGGAATTGCCTGTGCACGCTTCATTGGCAAC

CGGACCATTTATGTGGACTCGCTTCAGATGCAGGGGGAGATTGAAA

ACCGAATCACAGCGGCCTTCACCATGATCGGCACGTCTACGCACCT

GTCGGACCAGTGCTCACAGTTCGCCATCCCATCCTTCTGCCACTTC

GTGTTTCCTCTGTGCGACGCGCGCTCCCGGGCACCCAAGCCGCGTG

AGCTGTGCCGCGACGAGTGCGAGGTGCTGGAGAGCGACCTGTGCCG

CCAGGAGTACACCATCGCCCGCTCCAACCCGCTCATCCTCATGCGG

CTTCAGCTGCCCAAGTGTGAGGCGCTGCCCATGCCTGAGAGCCCCG

ACGCTGCCAAC

An example mouse ROR2 protein has the amino acid sequence of:

(SEQ ID NO: 7)
MARGWVRPSRVPLCARAVWTAAALLLWTPWTAGEVEDSEAIDTLGQ

PDGPDSPLPTLKGYFLNFLEPVNNITIVQGQTAILHCKVAGNPPPN

VRWLKNDAPVVQEPRRVIIRKTEYGSRLRIQDLDTTDTGYYQCVAT
NGLKTITATGVLYVRLGPTHSPNHNFQDDDQEDGFCQPYRGIACAR
FIGNRTIYVDSLQMQGEIENRITAAFTMIGTSTQLSDQCSQFAIPS
FCHFVFPLCDARSRAPKPRELCRDECEVLENDLCRQEYTIARSNPL
ILMRLQLPKCEALPMPESPDAANCMRIGIPAERLGRYHQCYNGSGA
DYRGMASTTKSGHQCQPWALQHPHSHRLSSTEFPELGGGHAYCRNP
GGQVEGPWCFTQNKNVRVELCDVPPCSPRDGSKMGILYILVPSIAI
PLVIACLFFLVCMCRNKQKASASTPQRRQLMASPSQDMEMPLISQH
KQAKLKEISLSTVRFMEELGEDRFGKVYKGHLFGPAPGEPTQAVAI
KTLKDKAEGPLREEFRQEAMLRARLQHPNIVCLLGVVTKDQPLSMI

FSYCSHGDLHEFLVMRSPHSDVGSTDDDRTVKSALEPPDFVHVVAQ
IAAGMEFLSSHHVVHKDLATRNVLVYDKLNVRISDLGLFREVYSAD
YYKLMGNSLLPIRWMSPEAVMYGKFSIDSDIWSYGVVLWEVFSYGL
QPYCGYSNQDVVEMIRSRQVLPCPDDCPAWVYALMIECWNEFPSRR
PRFKDIHSRLRSWGNLSNYNSSAQTSGASNTTQTSSLSTSPVSNVS
NARYMAPKQKAQPFPQPQFIPMKGQIRPLVPPAQLYIPVNGYQPVP
AYGAYLPNFYPVQIPMQMAPQQVPPQMVPKPSSHHSGSGSTSTGYV
TTAPSNTSVADRAALLSEGTEDAQNIAEDVAQSPVQEAEEEEEGSV
PETELLGDNDTLQVTEAAHVQLEA

An example mouse cDNA encoding ROR2 has the nucleotide sequence:

(SEQ ID NO: 8)
```
atggctcggggctgggtgcggccgagccgtgtgcctctgtgcgcccggccgtctggacg
gctgcggcgctcctgctctggacaccctggacggcaggtgaagtggaagattcggaggca
atcgacacccttgggacaacctgatggaccggacagcccacttcccactctgaaaggctac
tttctgaatttctggagccagtcaacaatatcaccattgttcagggccagacggcaatc
ctgcactgcaaggtggcgggaaacccacctcccaatgtgcggtggctgaagaatgatgcc
ccggttgtgcaagagccacgaagggtcgtcatccggaagacagaatacggctcccggctg
cggatccaagacctggacacaacagacacaggctactaccagtgtgtggctaccaacggg
ctgaagaccatcactgccactgggttctatatgtgcggctcggtccgacgcacagcccg
aaccacaattttcaggatgacgatcaggaagatggcttctgccagccgtaccgagggatc
gcttgtgcgcgcttcattgggaaccggactatttatgtggactccctccagatgcagggg
gagattgaaaaccgaatcacagctgccttcaccatgatcggcacctccacgcaactgtca
gaccagtgttcacagtttgccatcccatccttctgccacttcgtcttccctctgtgcgac
gcatgctcccgggcgcccaagcctcgcgaactgtgccgggatgaatgtgaggtgctggag
aacgacctgtgccgccaggagtacaccatcgcccgctccaacccgctcatcctcatgcgg
ctccagctgcccaagtgcgaagcgctgcccatgcccgagagcccggatgctgcgaactgc
atgcgcatcggggatccccgcggagaggctggtcgctaccaccagtgctacaacggctcc
ggcgccgattacagggggatggccagtaccaccaagtcaggccaccagtgtcagccttgg
gctctgcagcaccccacagccatcgcctatccagcacggaattccctgagctgggagga
ggccatgcctactgccggaaccccgggggccagatggaaggcccgtggtgctttacgcag
aataaaaacgtacgcgtggaactgtgtgacgtaccccgtgtagtcccgatatggcagc
aagatggggattctgtacatcctggtccccagcattgctatccccctggtcatcgcttgc
ctgttcttcctcgtctgcatgtgccgcaacaaacagaaggcttcggcctccacccacag
cgccggcagctgatggcctctcccagccaggacatggagatgccactcatcagccagcac
aaacaggccaaactcaaagagatcagcttgtccacagtgaggttcatggaggagctcggg
gaggaccggtttggcaaggtctacaaaggccacctgttcgggcctgccccaggagaacca
acccaggccgtggccatcaagacgctgaaagacaaggctgaggggcccctgcgggaggag
ttccggcaagaggcgatgctccgggcccgactgcagcaccccaacatcgtctgtcctcc
taggcgtcgtgaccaaggaccaacccttgagcatgatcttcagctactgttcccatggcgac
```

```
-continued
cttcatgaattcctggtcatgcgctcgccgcactccgatgtgggcagcaccgatgacgac cgcacagtgaagtcagccctggagccccggacttcgtgcacgtggtggcgcagatcgct gcggggatggagttcctgtccagccaccacgtgtgccataaggacctggccacacgcaat gtgctggtgtacgacaagctgaacgtgaggatctcagacttgggcctcttccgtgaggta tactccgcagattactacaaactcatgggcaattcactgctgcccatccgctggatgtcc cccgaggccgtcatgtatggaaagttctccatcgactctgacatctggtcctacggtgtg gtcctctgggaggtctttagctacggcctgcagccctactgtgggtactccaaccaggac gtggtggagatgatccggagccggcaggtgctgccctgcccggatgactgccccgcctgg gtctatgccctcatgattgaatgctggaatgagttcccaagccggaggccccgctttaag gacatccacagccggctccggtcctggggcaacctatccaactataatagttccgcgcag acctcaggagccagcaacaccacacagaccagctccctgagcaccagcccgtaagcaat gtgagcaatgcccgctatatggccccaagcagaaggcccagcccttcccacagcctcag ttcatcccatgaagggtcagatcagaccttggtgcccccgcacagctgtacatcccg gtgaacggctatcagccggtaccggcatacggggcctacctgcccaacttctacccagtc cagatccccatgcagatggccccacagcaggtgcccctcagatggtccccaagccgagc tcacaccacagtggcagcggctccaccagcactggctacgtcaccacggcgccctccaat acatctgtggcggacagggcggccctactctctgagggcaccgaggatgtacagaacatc gcggaagacgtggcccagagccctgtgcaggaagcagaggaggaggaggagggtctgtc cctgagactgaactcctgggagacaatgacacgctccaggtgaccgaggcggctcatgtc cagcttgaagcctga
```

The ROR2 receptor has been shown to bind members of the Wnt family of secreted extracellular glycoproteins involved in a variety of signalling pathways, including Wnt5a, Wnt3a, Wnt1, Wnt11, Wnt4 and Wnt16. Wnt5a, Wnt3a, Wnt1, Wnt11, Wnt4 and Wnt16 can activate ROR-2 dependent signalling (Gao et al., (2011) Dev. Cell 20: 163-176).Wnt5a has been shown to induce ROR2 homodimerization and tyrosine phosphorylation in U2OS human osteoblastic cells. Furthermore, in the presence of Wnt5a increased phosphorylation of the ROR2 substrate 14-3-3beta scaffold protein was observed, indicating that Wnt5a binding causes activation of the ROR2 signalling cascade (Liu et al. 2008). The Wnt5a/ROR2 signalling pathway inhibits canonical Wnt-β-catenin signalling (mediated by the receptor Frizzled).

ROR2 targets the Ctgf gene which encodes connective tissue growth factor. ROR2 also targets the Yap, Taz, and Wnt5a genes which encode YAP (yes-associated protein), TAZ and WNT5A proteins respectively (Park et al. (2015) Cell 162: 780-794). Monomeric ROR2 may also interact with other proteins to form a receptor complex capable of downstream signalling. For example, on activation two ROR2 molecules may interact to form a homodimer. Alternatively, ROR2 may form a heterodimer with ROR1. ROR2 may also interact (e.g. bind to) other ROR2 co-receptors, including but not limited to frizzled receptors or scaffolding proteins (e.g. syndecans). These interactions may be necessary for downstream signalling by ROR2 and therefore ROR2 signalling may be inhibited by disrupting these interactions.

Thus, ROR2 activation/inhibition may be evaluated by a number of different methods, such as measuring (i) ROR2 induced inhibition of Wnt-β-catenin signalling, (ii) ROR2 tyrosine phosphorylation, (iii) phosphorylation of ROR2 downstream targets, such as 14-3-3beta scaffold protein, (iv) expression of ROR2 target genes, such as Ctgf, Yap, Taz and Wnt5a, or (v) the capacity of ROR2 to form a receptor complex (e.g. whether ROR2 can interact with other members of the receptor complex). A person skilled in the art, would be able to select appropriate techniques for measuring each of (i) to (v).

ROR2 Inhibitors

The present invention relates to ROR2 inhibitors and therapeutic uses thereof in treating and/or preventing cartilage loss and/or treating and/or preventing osteoarthritis, treating and/or preventing osteoarthritis associated pain, promoting cartilage repair, and/or preventing cartilage degradation.

An ROR2 inhibitor may partially or fully inhibit (e.g. reduce, prevent, abolish, or ameliorate) at least one function or activity of ROR2. For example, as defined herein, an ROR2 inhibitor of the invention inhibits at least one activity or function of ROR2 that results in, for example, stimulation of chondrocyte differentiation (which may be associated with increased expression of chondrocytic differentiation markers e.g. COL2A1, AGGRECAN, ERG), decreased expression of Col1A1 and/or ColX, decreased expression of collagen degrading enzymes ADAMTS-4 and ADAMTS-5, increased accumulation of GAG (for example reduced degradation of GAG and/or increased expression of GAG), and/or reduction in OA associated pain. Inhibition of ROR2 may also result in decreased transcription of an endogenous Ctgf gene and/or decreased expression of an endogenous CTGF protein An ROR2 inhibitor of the invention may act via any mechanism that reduces at least one function or activity of ROR2. By way of example, an ROR2 inhibitor of the invention may inhibit a function or activity of ROR2 by:

(a) reducing or preventing transcription of an endogenous Ror2 gene (e.g. introducing a mutation into the endogenous Ror2 gene or deleting a portion of the endogenous Ror2 gene);

(b) reducing or preventing translation of mRNA encoding an ROR2 protein (e.g. by targeting the mRNA encoding the ROR2 protein for degradation);

(c) reducing or preventing the interaction between an ROR2 protein and one or more activating ligands such as Wnt family members (e.g. Wnt5a, Wnt3a, Wnt1, Wnt11, Wnt4 and Wnt16);

(d) reducing or preventing the interaction between an ROR2 protein and a member of an ROR2 receptor complex, for example by reducing or preventing the interaction between a first ROR2 protein and a second ROR2 protein, and/or reducing or preventing the interaction between an ROR2 protein and an ROR1 protein, a frizzled receptor protein and/or a scaffold protein (e.g. a syndecan);

(e) reducing or preventing the interaction between ROR2 interaction with downstream targets, such as 14-3-3beta scaffold protein, and/or (f) reducing or preventing ROR2's ability to phosphorylate a downstream target protein (e.g. 14-3-3beta).

An ROR2 inhibitor of the invention may reduce or prevent the interaction between an endogenous ROR2 and its activating ligands by competing by binding to one or more activating ligands of ROR2, such as a Wnt family member (e.g. Wnt5a, Wnt3a, Wnt1, Wnt11, Wnt4 and/or Wnt16).

In one embodiment, the ROR2 inhibitor is a soluble ROR2 protein. The terms "soluble ROR2 protein" and "soluble fragment of an ROR2 protein" are used interchangeably herein. The soluble ROR2 protein may comprise all or a portion of one or more extracellular domains of a full-length ROR2 protein, such as an ROR2 protein having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, or at least 99.9% sequence identity to SEQ ID NO: 5 or an ROR2 protein encoded by a polynucleotide having at having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, or at least 99.9% sequence identity to SEQ ID NO: 6.

The soluble ROR2 protein may comprise all or a portion of one or more extracellular domains of an ROR2 protein having the sequence of SEQ ID NO: 5. The soluble ROR2 protein may comprise all or a portion of one or more extracellular domains of an ROR2 protein encoded by a polynucleotide having the sequence of SEQ ID NO: 6.

The soluble ROR2 protein may comprise all or a portion of one or more extracellular domains of a full-length ROR2 protein having the sequence of SEQ ID NO: 7 or a full-length ROR2 protein having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, or at least 99.9% sequence identity to SEQ ID NO: 7. The soluble ROR2 protein may comprise all or a portion of one or more extracellular domains of a full-length ROR2 protein encoded by a polynucleotide having the sequence of SEQ ID NO: 8 or a polynucleotide having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, or at least 99.9% sequence identity to SEQ ID NO: 8.

As discussed above, the extracellular portion/domain of ROR2 comprises, from the N-terminus: a signal peptide, an immunoglobulin (Ig) domain, a cysteine rich domain (CRD) and a Kringle domain. The extracellular portion/domain of human ROR2 protein may have amino acid sequence of SEQ ID NO: 10.

The soluble ROR2 protein may comprise a polypeptide having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, or at least 99.9% sequence identity to SEQ ID NO: 10. The soluble ROR2 protein may comprise a polypeptide having the sequence of SEQ ID NO: 10.

The soluble ROR2 protein may comprise a polypeptide encoded by a polynucleotide having the sequence of SEQ ID NO: 11 or a polynucleotide having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, or at least 99.9% sequence identity to SEQ ID NO: 11.

The soluble ROR2 protein may comprise all or a portion of the CRD domain of ROR2. As discussed above, an example CRD domain of a human ROR2 protein has the sequence of SEQ ID NO 12. An example CRD domain of a human ROR2 protein is encoded by a polynucleotide having the sequence of SEQ ID NO: 13. The soluble ROR2 protein may comprise a polypeptide having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, or at least 99.9% sequence identity to SEQ ID NO: 12. The soluble protein may comprise a polypeptide having the sequence of SEQ ID NO: 12. The soluble ROR2 protein may comprise a polypeptide encoded by a polynucleotide having the sequence of SEQ ID NO: 13 or a polynucleotide having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, or at least 99.9% sequence identity to SEQ ID NO: 13.

The soluble ROR2 protein may comprise a fragment of an extracellular portion/domain of an ROR2 protein. The fragment of the extracellular portion/domain may be a functional fragment capable of partially or fully inhibiting (e.g. reducing, preventing, abolishing, or ameliorating) at least one function or activity of ROR2. For example, the fragment of the extracellular portion/domain of an ROR2 protein may be capable of:

(i) reducing or preventing the interaction between an ROR2 protein and one or more activating ligands such as Wnt family members (e.g. Wnt5a, Wnt3a, Wnt1, Wnt11, Wnt4 and Wnt16);

(ii) reducing or preventing the interaction between an ROR2 protein and a member of an ROR2 receptor complex, for example by reducing or preventing the interaction between a first ROR2 protein and a second ROR2 protein, and/or reducing or preventing the interaction between an ROR2 protein and an ROR1 protein, a frizzled receptor protein and/or a scaffold protein (e.g. a syndecan);

(iii) reducing or preventing the interaction between ROR2 interaction with downstream targets, such as 14-3-3beta scaffold protein, and/or (iv) reducing or preventing ROR2's ability to phosphorylate a downstream target protein (e.g. 14-3-3beta).

The fragment of the extracellular portion/domain an ROR2 protein may be capable of reducing or preventing the interaction between an endogenous ROR2 and its activating ligands by competing by binding to one or more activating ligands of ROR2, such as a Wnt family member (e.g. Wnt5a, Wnt3a, Wnt1, Wnt11, Wnt4 and/or Wnt16).

The soluble ROR2 protein may comprise a fragment of a polypeptide having the sequence of SEQ ID NO: 10 or a polypeptide having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, or at least 99.9% sequence identity to SEQ ID NO: 10.

The soluble ROR2 protein may comprise a fragment of a polypeptide encoded by a polynucleotide having the sequence of SEQ ID NO: 11 or a polynucleotide having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9% sequence identity to SEQ ID NO: 11.

The fragment of the extracellular portion/domain of an ROR2 protein may be at least about 10, 20, 30, 40, 50, 60, 70, 80, 90, 100, 120, 140, 160, 180, 200, 225, 250, 275, 300, 325, 350, 375, or 400 amino acids in length. The fragment of the extracellular portion/domain of an ROR2 protein may be about 10, 20, 30, 40, 50, 60, 70, 80, 90, 100, 120, 140, 160, 180, 200, 225, 250, 275, 300, 325, 350, 375, or 400 amino acids in length. The fragment of the extracellular portion/domain of an ROR2 protein may be from 10 to 400, from 20 to 375, from 30 to 350, from 40 to 325, from 50 to 300, from 60 to 275, from 70 to 250, from 90 to 225, from 100 to 200, from 120 to 180, from 140 to 160 amino acids in length.

The fragment of the extracellular portion/domain of an ROR2 protein may comprise at least about 10, 20, 30, 40, 50, 60, 70, 80, 90, 100, 120, 140, 160, 180, 200, 225, 250, 275, 300, 325, 350, 375, or 400 contiguous amino acids of SEQ ID NO: 10 or a polypeptide having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, or at least 99.9% sequence identity to SEQ ID NO: 10. The fragment of the extracellular portion/domain of an ROR2 protein may comprise about 10, 20, 30, 40, 50, 60, 70, 80, 90, 100, 120, 140, 160, 180, 200, 225, 250, 275, 300, 325, 350, 375, or 400 contiguous amino acids of SEQ ID NO: 10 or a polypeptide having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, or at least 99.9% sequence identity to SEQ ID NO: 10. The fragment of the extracellular portion/domain of an ROR2 protein may comprise from 10 to 400, from 20 to 375, from 30 to 350, from 40 to 325, from 50 to 300, from 60 to 275, from 70 to 250, from 90 to 225, from 100 to 200, from 120 to 180, from 140 to 160 contiguous amino acids of SEQ ID NO: 10 or a polypeptide having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, or at least 99.9% sequence identity to SEQ ID NO: 10.

The fragment of the extracellular portion/domain of an ROR2 protein may comprise at least about 10, 20, 30, 40, 50, 60, 70, 80, 90, 100, 120, 140, 160, 180, 200, 225, 250, 275, 300, 325, 350, 375, or 400 contiguous amino acids of a polypeptide encoded by a polynucleotide having the sequence of SEQ ID NO: 11 or a polynucleotide having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, or at least 99.9% sequence identity to SEQ ID NO: 11. The fragment of the extracellular portion/domain of an ROR2 protein may comprise about 10, 20, 30, 40, 50, 60, 70, 80, 90, 100, 120, 140, 160, 180, 200, 225, 250, 275, 300, 325, 350, 375, or 400 contiguous amino acids of a polypeptide encoded by a polynucleotide having the sequence of SEQ ID NO:

11 or a polynucleotide having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, or at least 99.9% sequence identity to SEQ ID NO: 11. The fragment of the extracellular portion/domain of an ROR2 protein may comprise from 10 to 400, from 20 to 375, from 30 to 350, from 40 to 325, from 50 to 300, from 60 to 275, from 70 to 250, from 90 to 225, from 100 to 200, from 120 to 180, from 140 to 160 contiguous amino acids of a polypeptide encoded by a polynucleotide having the sequence of SEQ ID NO: 11 or a polynucleotide having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, or at least 99.9% sequence identity to SEQ ID NO: 11.

The fragment of the extracellular portion/domain of an ROR2 protein may comprise at least about 10, 20, 30, 40, 50, 60, 70, 80, 90, 100, 120, 140, 160, 180, 200, 225, 250, 275, 300, 325, 350, 375, or 400 contiguous amino acids of SEQ ID NO: 7 or a polypeptide having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, or at least 99.9% sequence identity to SEQ ID NO: 7. The fragment of the extracellular portion/domain of an ROR2 protein may comprise about 10, 20, 30, 40, 50, 60, 70, 80, 90, 100, 120, 140, 160, 180, 200, 225, 250, 275, 300, 325, 350, 375, or 400 contiguous amino acids of SEQ ID NO: 7 or a polypeptide having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, or at least 99.9% sequence identity to SEQ ID NO: 7. The fragment of the extracellular portion/domain of an ROR2 protein may comprise from 10 to 400, from 20 to 375, from 30 to 350, from 40 to 325, from 50 to 300, from 60 to 275, from 70 to 250, from 90 to 225, from 100 to 200, from 120 to 180, from 140 to 160 contiguous amino acids of SEQ ID NO: 7 or a polypeptide having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, or at least 99.9% sequence identity to SEQ ID NO: 7.

The fragment of the extracellular portion/domain of an ROR2 protein may comprise at least about 10, 20, 30, 40, 50, 60, 70, 80, 90, 100, 120, 140, 160, 180, 200, 225, 250, 275, 300, 325, 350, 375, or 400 contiguous amino acids of a polypeptide encoded by a polynucleotide having the sequence of SEQ ID NO: 8 or a polynucleotide having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, or at least 99.9% sequence identity to SEQ ID NO: 8. The fragment of the extracellular portion/ domain of an ROR2 protein may comprise about 10, 20, 30, 40, 50, 60, 70, 80, 90, 100, 120, 140, 160, 180, 200, 225, 250, 275, 300, 325, 350, 375, or 400 contiguous amino acids amino acids of a polypeptide encoded by a polynucleotide having the sequence of SEQ ID NO: 8 or a polynucleotide having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, or at least 99.9% sequence identity to SEQ ID NO: 8. The fragment of the extracellular portion/domain of an ROR2 protein may comprise from 10 to 400, from 20 to 375, from 30 to 350, from 40 to 325, from 50 to 300, from 60 to 275, from 70 to 250, from 90 to 225, from 100 to 200, from 120 to 180, from 140 to 160 contiguous amino acids amino acids of a polypeptide encoded by a polynucleotide having the sequence of SEQ ID NO: 8 or a polynucleotide having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, or at least 99.9% sequence identity to SEQ ID NO: 8.

The soluble ROR2 protein may usefully comprise other domains, linkers, cleavage tags, and/or affinity tags in addition to an extracellular portion/domain of an ROR2 protein. For example, the soluble ROR2 protein may further comprise a suitable membrane anchor capable of targeting the soluble ROR2 protein to cells. Any suitable membrane anchor known in the art may be used in the soluble ROR2 proteins of the present invention. The person skilled in the art is able to select a suitable membrane anchor.

An example membrane anchor that can be used in the soluble ROR2 proteins of the present invention is a GPI anchor. A GPI anchor typically comprises a core of phosphoethanolamine (PE)-3Man-GlcN-phosphatidylinositol (PI)-glycerol linked to alkyl, alkyl fatty acids or ceramide chains, which are able to interact hybrophobically with a lipid bilayer e.g. a cell membrane. The membrane anchor may be connected to the C-terminus of the extracellular domain of the ROR2 protein.

The membrane anchor may be connected to the extracellular portion/domain of the ROR2 protein by a linker. Accordingly, where the ROR2 protein comprises a GPI anchor, said GPI anchor may be connected to the C-terminus of the extracellular portion/domain of the ROR2 protein by a linker, which may be referred to as a GPI linker. An example GPI linker may have the following amino acid sequence SSSTTTTTTTTLLLLLLLLLLLLLL (SEQ ID NO: 9). The GP1 linker may be encoded by the following nucleotide sequence: AGCAGCAGCACCACCACCAC-CACCACCACCACCCTGCTGCTGCTGCTGCT GCTGCTGCTGCTGCTGCTG (SEQ ID NO: 14). SEQ ID NO: 14 may be followed by a stop codon e.g. TGA, TAA or TAG (for example in a vector).

The soluble fragment of the ROR2 protein may further comprise an affinity tag. The inclusion of an affinity tag allows the soluble ROR2 protein to be readily isolated and/or purified. Any suitable affinity tag know in the art may be used in the soluble ROR2 protein. The person skilled in the art is able to select a suitable affinity tag.

The affinity tag may be selected from the group consisting of a Myc/His tag, a Myc tag, a His tag, a glutathione S-transferase (GST) tag, a maltose binding protein (MBP) tag, a Strep tag II, a FLAG tag, an alkaline phosphatase tag, a bacteriophage T7 epitope tag (T7-tag), a calmodulin binding peptide (CBP) tag, a galactose binding protein (GBP) tag, a human influenza hemagglutinin (HA) tag, and combinations thereof.

The affinity tag may be C-terminal to the extracellular portion/domain or the membrane anchor.

In one embodiment, the soluble fragment of the ROR2 protein further comprises a cleavage tag arranged to permit the affinity tag to be cleaved from the soluble fragment of the ROR2 protein. In this way, the soluble ROR2 protein may be captured via the affinity tag and then recovered by cleaving the cleavage tag. The cleavage tag may be C-terminal to the extracellular portion/domain or the membrane anchor and N-terminal to the affinity tag. The cleavage tag is selected from the group consisting of a enterokinase cleavage tag, a tobacco etch virus protease cleavage site, a thrombin cleavage tag, a factor Xa (FXa) cleavage tag, a human rhinovirus (HRV) 3C Protease ('PreScission') cleavage tag.

In one embodiment, the cleavage tag is an enterokinase cleavage tag. For example, an enterokinase cleavage tag having the amino acid sequence KDDDD (SEQ ID NO: 20). The enterokinase cleavage tag may be encoded by the nucleotide sequence AAAGATGATGATGAT (SEQ ID NO: 21). Alternatively, the enterokinase cleavage tag may be encoded by the nucleotide sequence:

```
                                   (SEQ ID NO: 22)
AGCAGCAGCACCACCACCACCACCACCACCACCCTGCTGCTGCTGC

TGCTGCTGCTGCTGCTGCTGCTGCTGCTGAAAGATGATGATGATGA

ACAAAAACTCATCTCAGAAGAGGATCTGAATATGCATACCGGTCAT

CATCACCATCACCATTGA
```

In one embodiment, the cleavage tag is a tobacco etch virus protease cleavage tag. For example, a tobacco etch virus protease cleavage tag having the amino acid sequence GQFYLNE (SEQ ID NO: 23). The tobacco etch virus protease cleavage tag may be encoded by the nucleotide sequence GGCCAGTTTTATCTGAACGAA (SEQ ID NO: 24). Alternatively, the tobacco etch virus protease cleavage tag may be encoded by the nucleotide sequence:

```
                                   (SEQ ID NO: 25)
AGCAGCAGCACCACCACCACCACCACCACCACCCTGCTGCTGCTGC

TGCTGCTGCTGCTGCTGCTGCTGCTGCTGGGCCAGTTTTATCTGAA
```

An example soluble ROR2 protein of the invention comprising an extracellular portion/domain of an ROR2 protein and a GPI linker has the amino acid sequence:

(SEQ ID NO: 26)
MARGSALPRRPLLCIPAVWAAAALLLSVSRTSGEVEVLDPNDPLGP

LDGQDGPIPTLKGYFLNFLEPVNNITIVQGQTAILHCKVAGNPPPN

VRWLKNDAPVVQEPRRIIRKTEYGSRLRIQDLDTTDTGYYQCVATN

GMKTITATGVLFVRLGPTHSPNHNFQDDYHEDGFCQPYRGIACARF

IGNRTIYVDSLQMQGEIENRITAAFTMIGTSTHLSDQCSQFAIPSF

CHFVFPLCDARSRAPKPRELCRDECEVLESDLCRQEYTIARSNPLI

LMRLQLPKCEALPMPESPDAANCMRIGIPAERLGRYHQCYNGSGMD

YRGTASTTKSGHQCQPWALQHPHSHHLSSTDFPELGGGHAYCRNPG

GQMEGPWCFTQNKNVRMELCDVPSCSPRDSSKMGILYSSSTTTTTT

TTLLLLLLLLLLLLLL

Thus, the present invention provides an ROR2 inhibitor comprising the polypeptide of SEQ ID NO: 26. The present invention also provides an ROR2 inhibitor comprising a polypeptide having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, or at least 99.9% sequence identity to SEQ ID NO: 26.

An example soluble ROR2 protein of the invention comprising an extracellular portion/domain of an ROR2 protein and a GPI linker is encoded by a polynucleotide having the sequence:

(SEQ ID NO: 27)
ATGGCCCGGGGCTCGGCGCTCCCGCGGCGGCCGCTGCTGTGCATCC

CGGCCGTCTGGGCGGCCGCCGCGCTTCTGCTCTCAGTGTCCCGGAC

TTCAGGTGAAGTGGAGGTTCTGGATCCGAACGACCCTTTAGGACCC

CTTGATGGCAGGACGGCCCGATTCCAACTCTGAAAGGTTACTTTC

TGAATTTTCTGGAGCCAGTAAACAATATCACCATTGTCCAAGGCA

GACGGCAATTCTGCACTGCAAGGTGGCAGGAAACCCACCCCCTAAC

GTGCGGTGGCTAAAGAATGATGCCCCGGTGGTGCAGGAGCCGCGGC

GGATCATCATCCGGAAGACAGAATATGGTTCACGACTGCGAATCCA

GGACCTGGACACGACAGACACTGGCTACTACCAGTGCGTGGCCACC

AACGGGATGAAGACCATTACCGCCACTGGCGTCCTGTTTGTGCGGC

TGGGTCCAACGCACAGCCCAAATCATAACTTTCAGGATGATTACCA

CGAGGATGGGTTCTGCCAGCCTTACCGGGGAATTGCCTGTGCACGC

TTCATTGGCAACCGGACCATTTATGTGGACTCGCTTCAGATGCAGG

GGGAGATTGAAAACCGAATCACAGCGGCCTTCACCATGATCGGCAC

GTCTACGCACCTGTCGGACCAGTGCTCACAGTTCGCCATCCCATCC

TTCTGCCACTTCGTGTTTCCTCTGTGCGACGCGCGCTCCCGGGCAC

CCAAGCCGCGTGAGCTGTGCCGCGACGAGTGCGAGGTGCTGGAGAG

CGACCTGTGCCGCCAGGAGTACACCATCGCCCGCTCCAACCCGCTC

ATCCTCATGCGGCTTCAGCTGCCCAAGTGTGAGGCGCTGCCCATGC

CTGAGAGCCCCGACGCTGCCAACTGCATGCGCATTGGCATCCCAGC

CGAGAGGCTGGGCCGCTACCATCAGTGCTATAACGGCTCAGGCATG

GATTACAGAGGAACGGCAAGCACCACCAAGTCAGGCCACCAGTGCC

AGCCGTGGGCCCTGCAGCACCCCCACAGCCACCACCTGTCCAGCAC

AGACTTCCCTGAGCTTGGAGGGGGGCACGCCTACTGCCGGAACCCC

GGAGGCCAGATGGAGGGCCCCTGGTGCTTTACGCAGAATAAAAACG

TACGCATGGAACTGTGTGACGTACCCTCGTGTAGTCCCCGAGACAG

CAGCAAGATGGGGATTCTGTACAGCAGCAGCACCACCACCACCACC

ACCACCACCCTGCTGCTGCTGCTGCTGCTGCTGCTGCTGCTGCTGC

TGCTGAAAGATGATGATGATGAACAAAAACTCATCTCAGAAGAGGA

TCTGAATATGCATACCGGTCATCATCACCATCACCATTGA

Thus, the present invention provides an isolated polynucleotide having the sequence of SEQ ID NO: 27 or an isolated polynucleotide having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, or at least 99.9% sequence identity to SEQ ID NO: 27

The present invention also provides an ROR2 inhibitor comprising a polypeptide encoded by SEQ ID NO: 27. The present invention also provides an ROR2 inhibitor comprising a polypeptide encoded by a polynucleotide having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, or at least 99.9% sequence identity to SEQ ID NO: 27.

In one embodiment, the soluble ROR2 protein comprises from N-terminal to C-terminal: (i) an extracellular portion/domain of an ROR2 protein; (ii) a GPI linker; (iii) an enterokinase cleavage tag; and (iv) a Myc/His tag. An example soluble ROR2 protein of the invention comprising from N-terminal to C-terminal: (i) an extracellular portion/domain of an ROR2 protein; (ii) a GPI linker; (iii) an enterokinase cleavage tag; and (iv) a Myc/His tag has the amino acid sequence:

(SEQ ID NO: 28)
MARGSALPRRPLLCIPAVWAAAALLLSVSRTSGEVEVLDPNDPLGP

LDGQDGPIPTLKGYFLNFLEPVNNITIVQGQTAILHCKVAGNPPPN

VRWLKNDAPVVQEPRRIIRKTEYGSRLRIQDLDTTDTGYYQCVATN

GMKTITATGVLFVRLGPTHSPNHNFQDDYHEDGFCQPYRGIACARF

IGNRTIYVDSLQMQGEIENRITAAFTMIGTSTHLSDQCSQFAIPS

FCHFVFPLCDARSRAPKPRELCRDECEVLESDLCRQEYTIARSNP

LILMRLQLPKCEALPMPESPDAANCMRIGIPAERLGRYHQCYNGSG

```
MDYRGTASTTKSGHQCQPWALQHPHSHHLSSTDFPELGGGHAYCRN

PGGQMEGPWCFTQNKNVRMELCDVPSCSPRDSSKMGILYSSSTTTT

TTTTLLLLLLLLLLLLLLLKDDDDEQKLISEEDLNMHTGHHHHHH
```

Thus, the present invention provides an ROR2 inhibitor comprising the polypeptide of SEQ ID NO: 28. The present invention also provides an ROR2 inhibitor comprising a polypeptide having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, or at least 99.9% sequence identity to SEQ ID NO: 28.

An example soluble ROR2 protein of the invention comprising from N-terminal to C-terminal: (i) an extracellular portion/domain of an ROR2 protein; (ii) a GPI linker; (iii) an enterokinase cleavage tag; and (iv) a Myc/His tag is encoded by a polynucleotide having the sequence:

```
                                            (SEQ ID NO: 29)
ATGGCCCGGGGCTCGGCGCTCCCGCGGCGGCCGCTGCTGTGCATCC

CGGCCGTCTGGGCGGCCGCCGCGCTTCTGCTCTCAGTGTCCCGGAC

TTCAGGTGAAGTGGAGGTTCTGGATCCGAACGACCCTTTAGGACCC

CTTGATGGGCAGGACGGCCCGATTCCAACTCTGAAAGGTTACTTTC

TGAATTTTCTGGAGCCAGTAAACAATATCACCATTGTCCAAGGCCA

GACGGCAATTCTGCACTGCAAGGTGGCAGGAAACCCACCCCCTAAC

GTGCGGTGGCTAAAGAATGATGCCCCGGTGGTGCAGGAGCCGCGGC

GGATCATCATCCGGAAGACAGAATATGGTTCACGACTGCGAATCCA

GGACCTGGACACGACAGACACTGGCTACTACCAGTGCGTGGCCACC

AACGGGATGAAGACCATTACCGCCACTGGCGTCCTGTTTGTGCGGC

TGGGTCCAACGCACAGCCCAAATCATAACTTTCAGGATGATTACCA

CGAGGATGGGTTCTGCCAGCCTTACCGGGGAATTGCCTGTGCACGC

TTCATTGGCAACCGGACCATTTATGTGGACTCGCTTCAGATGCAGG

GGGAGATTGAAAACCGAATCACAGCGGCCTTCACCATGATCGGCAC

GTCTACGCACCTGTCGGACCAGTGCTCACAGTTCGCCATCCCATCC

TTCTGCCACTTCGTGTTTCCTCTGTGCGACGCGCGCTCCCGGGCAC

CCAAGCCGCGTGAGCTGTGCCGCGACGAGTGCGAGGTGCTGGAGAG

CGACCTGTGCCGCCAGGAGTACACCATCGCCCGCTCCAACCCGCTC

ATCCTCATGCGGCTTCAGCTGCCCAAGTGTGAGGCGCTGCCCATGC

CTGAGAGCCCCGACGCTGCCAACTGCATGCGCATTGGCATCCCAGC

CGAGAGGCTGGGCCGCTACCATCAGTGCTATAACGGCTCAGGCATG

GATTACAGAGGAACGGCAAGCACCACCAAGTCAGGCCACCAGTGCC

AGCCGTGGGCCCTGCAGCACCCCCACAGCCACCACCTGTCCAGCAC

AGACTTCCCTGAGCTTGGAGGGGGGCACGCCTACTGCCGGAACCCC

GGAGGCCAGATGGAGGGCCCCTGGTGCTTTACGCAGAATAAAAACG

TACGCATGGAACTGTGTGACGTACCCTCGTGTAGTCCCCGAGACAG

CAGCAAGATGGGGATTCTGTACAGCAGCAGCACCACCACCACCACC
```

```
ACCACCACCCTGCTGCTGCTGCTGCTGCTGCTGCTGCTGCTGCTGC

TGCTGAAAGATGATGATGATGAACAAAAACTCATCTCAGAAGAGGA

TCTGAATATGCATACCGGTCATCATCACCATCACCATTGA
```

Thus, the present invention provides an isolated polynucleotide having the sequence of SEQ ID NO: 29 or an isolated polynucleotide having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, or at least 99.9% sequence identity to SEQ ID NO: 29.

The present invention also provides an ROR2 inhibitor comprising a polypeptide encoded by SEQ ID NO: 29. The present invention also provides an ROR2 inhibitor comprising a polypeptide encoded by a polynucleotide having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, or at least 99.9% sequence identity to SEQ ID NO: 29.

In one embodiment, the soluble ROR2 protein comprises from N-terminal to C-terminal: (i) an extracellular portion/domain of an ROR2 protein; (ii) a GPI linker; (iii) a tobacco etch virus protease cleavage tag; and (iv) a Myc/His tag. An example soluble ROR2 protein of the invention comprising from N-terminal to C-terminal: (i) an extracellular domain of an ROR2 protein; (ii) a GPI linker; (iii) a tobacco etch virus protease cleavage tag; and (iv) a Myc/His tag has the amino acid sequence:

```
                                            (SEQ ID NO: 30)
MARGSALPRRPLLCIPAVWAAAALLLSVSRTSGEVEVLDPNDPLGP

LDGQDGPIPTLKGYFLNFLEPVNNITIVQGQTAILHCKVAGNPPPN

VRWLKNDAPVVQEPRRIIIRKTEYGSRLRIQDLDTTDTGYYQCVATN

GMKTITATGVLFVRLGPTHSPNHNFQDDYHEDGFCQPYRGIACARF

IGNRTIYVDSLQMQGEIENRITAAFTMIGTSTHLSDQCSQFAIPSF

CHFVFPLCDARSRAPKPRELCRDECEVLESDLCRQEYTIARSNPLI

LMRLQLPKCEALPMPESPDAANCMRIGIPAERLGRYHQCYNGSGMD

YRGTASTTKSGHQCQPWALQHPHSHHLSSTDFPELGGGHAYCRNPG

GQMEGPWCFTQNKNVRMELCDVPSCSPRDSSKMGILYSSSTTTTTT

TTLLLLLLLLLLLLLLGQFYLNEEQKLISEEDLNMHTGHHHHHH
```

Thus, the present invention provides an ROR2 inhibitor comprising the polypeptide of SEQ ID NO: 30. The present invention also provides an ROR2 inhibitor comprising a polypeptide having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, or at least 99.9% sequence identity to SEQ ID NO: 30.

An example soluble ROR2 protein of the invention comprising from N-terminal to C-terminal: (i) an extracellular portion/domain of an ROR2 protein; (ii) a GPI linker; (iii) a tobacco etch virus protease cleavage tag; and (iv) a Myc/His tag is encoded by a polynucleotide having the sequence:

(SEQ ID NO: 31)
```
ATGGCCCGGGGCTCGGCGCTCCCGCGGCGGCCGCTGCTGTGCATCC
CGGCCGTCTGGGCGGCCGCCGCGCTTCTGCTCTCAGTGTCCCGGAC
TTCAGGTGAAGTGGAGGTTCTGGATCCGAACGACCCTTTAGGACCC
CTTGATGGCAGGACGGCCCGATTCCAACTCTGAAAGGTTACTTTC
TGAATTTTCTGGAGCCAGTAAACAATATCACCATTGTCCAAGGCA
GACGGCAATTCTGCACTGCAAGGTGGCAGGAAACCCACCCCCTAAC
GTGCGGTGGCTAAAGAATGATGCCCCGGTGGTGCAGGAGCCGCGGC
GGATCATCATCCGGAAGACAGAATATGGTTCACGACTGCGAATCCA
GGACCTGGACACGACAGACACTGGCTACTACCAGTGCGTGGCCACC
AACGGGATGAAGACCATTACCGCCACTGGCGTCCTGTTTGTGCGGC
TGGGTCCAACGCACAGCCCAAATCATAACTTTCAGGATGATTACCA
CGAGGATGGGTTCTGCCAGCCTTACCGGGGAATTGCCTGTGCACGC
TTCATTGGCAACCGGACCATTTATGTGGACTCGCTTCAGATGCAGG
GGGAGATTGAAAACCGAATCACAGCGGCCTTCACCATGATCGGCAC
GTCTACGCACCTGTCGGACCAGTGCTCACAGTTCGCCATCCCATCC
TTCTGCCACTTCGTGTTTCCTCTGTGCGACGCGCGCTCCCGGGCAC
CCAAGCCGCGTGAGCTGTGCCGCGACGAGTGCGAGGTGCTGGAGAG
CGACCTGTGCCGCCAGGAGTACACCATCGCCCGCTCCAACCCGCTC
ATCCTCATGCGGCTTCAGCTGCCCAAGTGTGAGGCGCTGCCCATGC
CTGAGAGCCCCGACGCTGCCAACTGCATGCGCATTGGCATCCCAGC
CGAGAGGCTGGGCCGCTACCATCAGTGCTATAACGGCTCAGGCATG
GATTACAGAGGAACGGCAAGCACCACCAAGTCAGGCCACCAGTGCC
AGCCGTGGGCCCTGCAGCACCCCCACAGCCACCACCTGTCCAGCAC
AGACTTCCCTGAGCTTGGAGGGGGGCACGCCTACTGCCGGAACCCC
GGAGGCCAGATGGAGGGCCCCTGGTGCTTTACGCAGAATAAAAACG
TACGCATGGAACTGTGTGACGTACCCTCGTGTAGTCCCCGAGACAG
CAGCAAGATGGGGATTCTGTACAGCAGCAGCACCACCACCACCACC
ACCACCACCCTGCTGCTGCTGCTGCTGCTGCTGCTGCTGCTGCTGC
TGCTGGGCCAGTTTTATCTGAACGAAGAACAAAAACTCATCTCAGA
AGAGGATCTGAATATGCATACCGGTCATCATCACCATCACCATTGA
```

Thus, the present invention provides an isolated polynucleotide having the sequence of SEQ ID NO: 31 or an isolated polynucleotide having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, or at least 99.9% sequence identity to SEQ ID NO: 31.

The present invention also provides an ROR2 inhibitor comprising a polypeptide encoded by SEQ ID NO: 31. The present invention also provides an ROR2 inhibitor comprising a polypeptide encoded by a polynucleotide having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, or at least 99.9% sequence identity to SEQ ID NO: 31.

Oligonucleotides Directed Against ROR2

The present invention provides oligonucleotides directed against ROR2 for use in treating osteoarthritis and/or promoting cartilage repair and/or treating osteoarthritis associated pain. Such oligonucleotides directed against ROR2 are ROR2 inhibitors according to the present invention.

In the context of this invention, the term "oligonucleotide" refers to an oligomer of nucleotide or nucleoside monomers consisting of naturally-occurring bases, sugars and intersugar (backbone) linkages. The term "oligonucleotide" also includes oligomers comprising non-naturally occurring monomers, or portions thereof, which function similarly. Such modified or substituted oligonucleotides are often preferred over native forms because of properties such as, for example, enhanced cellular uptake, reduced immunogenicity, and increased stability in the presence of nucleases.

Oligonucleotides are generally classified as deoxyribooligonucleotides or ribooligonucleotides, which are oligomers of DNA or RNA molecules. A deoxyribooligonucleotide consists of a 5-carbon sugar (deoxyribose) which is joined covalently to phosphate at the 5' and 3' carbons of the sugar to form an alternating, unbranched polymer. A ribooligonucleotide consists of a similar repeating structure where the 5-carbon sugar is ribose.

The oligonucleotides described herein can be single-stranded DNA or RNA, double-stranded DNA or RNA, DNA-RNA hybrids, or chimeric DNA-RNA structures. Examples of double-stranded RNA include, e.g., siRNA, short hairpin RNA (shRNA) and other RNAi agents such as pre-miRNA. Single-stranded oligonucleotides include, e.g., antisense oligonucleotides, ribozymes, mature miRNA, and triplex-forming oligonucleotides.

Using known techniques and based on a knowledge of the sequence of an Ror2 gene (e.g. based on the nucleotide sequences of SEQ ID NOs: 2 and 4), double-stranded RNA (dsRNA) molecules can be designed to suppress the Ror2 gene by sequence homology-based targeting of its RNA transcript. Such dsRNAs may be siRNAs, usually in a stem-loop ("hairpin") configuration, or micro-RNAs (miR-NAs). The sequence of such dsRNAs will comprise a portion that corresponds with that of a portion of the mRNA transcript of the Ror2 gene. This portion will usually be 100% complementary to the target portion within the allele comprising the dominant mutation but lower levels of complementarity (e.g. 60% or more, 65% or more, 70% or more, 75% or more, 80% or more, 85% or more, 90% or more, or 95% or more) may also be used.

Using known techniques and based on a knowledge of the sequence of a Ror2 gene (e.g. based on the nucleotide sequences of SEQ ID NOs: 2 and 4), a single-stranded antisense oligonucleotides can be designed to suppress the allele by sequence homology-based targeting of its RNA transcript. The sequence of such antisense oligonucleotides will comprise a portion that corresponds with that of a portion of the mRNA transcript or the Ror2 gene. This portion will usually be 100% complementary to the target portion within the allele comprising the dominant mutation but lower levels of complementarity (e.g. 60% or more, 65% or more, 70% or more, 75% or more, 80% or more, 85% or more, 90% or more or 95% or more) may also be used. In one embodiment, the oligonucleotide is an antisense oligonucleotide (AON). The AON may act by binding to pre-mRNA or mRNA via Watson-Crick base pairing and induces gene suppression by mechanisms such as through RNase H-mediated mRNA degradation. The AON may have a nucleotide sequence that is complementary to the mRNA encoding.

In some instances, the total length of the oligonucleotide may be up to 100, 90, 80, 70, 60, 50, 40, or 30 nucleotides. In others, the total length may be 29, 28, 27, 26, 25, 24, 23, 22, 21, 20, 19, 18, 17, 16, 15, 14, 13, 12, 11 or 10 nucleotides, particularly 14-25 nucleotides.

The AONs of the invention can be gapmers or altimers. A gapmer is a chimeric AON that contains a central block of DNA molecules and is flanked by blocks of 2'-O modified ribooligonucleotides or other artificially modified ribooligonucleotide monomers that protect the internal block from nuclease degradation. The oligonucleotides contain DNA bases, wherein some or all of the DNA bases have a phosphorothioated backbone. For example, none, 5 or more, 10 or more, 15 or more, 20 or more, 25 or more, or all of the DNA bases have a phosphorothioated backbone. DNA that contain phosphorothioated backbones provide an increased resistance to nucleases compared to unmodified DNA.

In one embodiment, the oligonucleotide comprises modifications to help enhance the properties of the oligonucleotide. Hence, the oligonucleotides of the invention may be modified by the substitution of at least one nucleotide with at least one modified nucleotide, ideally so that the in vivo and in vitro stability of the oligonucleotide is enhanced as compared to a corresponding unmodified oligonucleotide. The modified nucleotide may, for instance, be a sugar-modified nucleotide or a nucleobase-modified nucleotide. In some instances, two, three, four, five, six or seven modified nucleotides may be included, or at least that number, in others eight, nine, ten, eleven or twelve such modifications, or at least that number, may be included, in other cases, fifteen, twenty, twenty-one, twenty-two, twenty three, twenty-four, twenty-five or at least such numbers may be modified. In still others all of the nucleotides may be modified, or all but one, two, three, four or five nucleotides.

In some instances, the modified nucleotide is a 2'-deoxy ribonucleotide. In certain instances, the 2'-deoxy ribonucleotide is 2'-deoxy guanosine or 2'-deoxy adenosine. In other instances, the modified nucleotide is a 2'-O-methylguanosine, 2'-O-methyl (e.g., 2'-O-methylcytidine, 2'-O-methylpseudouridine, 2'-O-methyluridine, 2'-O-methyladenosine, 2'-O-methyl) ribonucleotide. In some cases, the modified nucleotide is selected from a 2'-amino, 2'-thio and 2'-fluoro modified ribonucleotide. In a further instances, the modified nucleotide is selected from the group consisting of 2'-fluoro-cytidine, 2'-fluoro-uridine, 2'-fluoro-guanosine, 2'-fluoro-adenosine, 2'-amino-cytidine, 2'-amino-uridine, 2'-amino-adenosine, 2'-amino-guanosine, 2'-amino-butyryl-pyrene-uridine and 2'-amino-adenosine. In an additional instances, the modified nucleotide is selected from 5-iodo-uridine, ribo-thymidine, 5-bromo-uridine, 2-aminopurine, 5-methyl-cytidine, 5-fluoro-cytidine, and 5-fluoro-uridine, 2,6-di-aminopurine, 4-thio-uridine, and 5-amino-allyl-uridine.

In some instances, the modified nucleotide includes: derivatization of the 5 position, for instance being selected from 5-(2-amino) propyl uridine, 5-bromo uridine, 5-propyne uridine, 5-propenyl uridine; derivatization of the 6 position, for instance 6-(2-amino)propyl uridine; derivatization of the 8-position for adenosine and/or guanosines, for instance 8-bromo guanosine, 8-chloro guanosine, or 8-fluoroguanosine, Nucleotide analogs which may be employed include deaza nucleotides, e.g., 7-deaza-adenosine; O- and N-modified (for instance alkylated, such as N6-methyl adenosine) nucleotides; and other heterocyclically modified nucleotide analogs. Examples of modifications to the sugar portion of the nucleotides which may be employed include the 2' OH-group being replaced by a group selected from H, OR, R, F, Cl, Br, I, SH, SR, NH2, NHR, NR2, COOR, or OR, wherein R is substituted or unsubstituted C1-C6 alkyl, alkenyl, alkynyl, aryl and so on. The phosphate group of the nucleotide may also be modified, such as by substituting one or more of the oxygens of the phosphate group with sulphur (for instance by employing phosphorothioates). Modifications may decrease the rate of hydrolysis of polynucleotides comprising the modified bases, for example by inhibiting degradation by exonucleases. In one preferred instance, the oligonucleotide is resistant to ribonucleases. Oligonucleotides which may be employed include those with modifications to promote such resistance, for instance an oligonucleotide of the invention may have preferably been modified with a 2'-O-methyl group (e.g., 2'-O-methylcytidine, 2'-O-methylpseudouridine, 2'-O-methylguanosine, 2'-O-methyluridine, 2'-O-methyladenosine, 2'-O-methyl) and additionally comprise a phosphorothioate backbone.

In some instances, oligonucleotides comprise oligonucleotides that contain phosphorothioate and 2'-O-methyl (e.g., 2'-O-methylcytidine, 2'-O-methylpseudouridine, 2'-O-methylguanosine, 2'-O-methyluridine, 2'-O-methyladenosine, 2'-O-methyl) modification. Other forms of oligonucleotide modifications may be employed, for example, locked nucleic acids (oligonucleotides comprising at least one 2'-C, 4'-C-oxy-methylene-linked bicyclic ribonucleotide monomer). In some instances the modified nucleotide employed may be 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluraci 1,5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

In some instances, the modified oligonucleotide may include modifications to the phosphate backbone such as methyl phosphonates, methyl phosphonothioates, phosphoromorpholidates, phosphoropiperazidates and phosphoramidates. In one example, every other one of the internucleotide bridging phosphate residues may be modified as described. In another non-limiting example, such oligonucleotides are oligonucleotides wherein at least one, or all, of the nucleotides contain a 2' loweralkyl moiety (e.g., C1-C4, linear or branched, saturated or unsaturated alkyl, such as methyl, ethyl, ethenyl, propyl, 1-propenyl, 2-propenyl, and isopropyl).

In one embodiment, the oligonucleotide is a small interfering RNA (siRNA). An siRNA acts by activating the RNAi-induced suppression complex (also known as the RISC complex). A siRNA of the invention may be unmodified or modified is capable of suppressing (i.e. partially or completely preventing) expression of an ROR2 protein. The siRNA of the invention may prevent expression of an Ror2 gene. The siRNA of the invention may prevent translation of an mRNA encoding a ROR2 protein. The siRNA of the invention may reduce or prevent ROR2 protein expression by affecting the post translational modification of an ROR2 protein. A siRNA of the invention may be between about 5 to 60 nucleotides in length, about 5 to 55 nucleotides in length, about 5 to 50 nucleotides in length, about 5 to 45 nucleotides in length, about 5 to 40 nucleotides in length, about 5 to 35 nucleotides in length, about 5 to 30 nucleotides in length, about 5 to 25 nucleotides in length, about 5 to 20 nucleotides in length, about 5 to 15 nucleotides in length, or about 5 to 10 nucleotides in length.

In some embodiments, the modified siRNA contains at least one 2'O-Me purine or pyrimidine nucleotide such as a 2'O-Me-guanosine, 2'O-Me-uridine, 2'O-Me-adenosine, and/or 2'O-Me-cytosine nucleotide. The modified nucleotides can be present in one strand (i.e., sense or antisense) or both strands of the siRNA. The siRNA sequences may have overhangs or blunt ends.

The modified siRNA may comprises from about 1% to about 100% (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, or 100%) modified nucleotides in the double-stranded region of the siRNA duplex. In certain embodiments, one, two, three, four, five, six, seven, eight, nine, ten, or more of the nucleotides in the double-stranded region of the siRNA comprise modified nucleotides.

Suitable siRNA sequences can be identified using any means known in the art. Typically, the methods described in Elbashir et al., *Nature,* 411:494-498 (2001) and Elbashir et al., *EMBO J.,* 20:6877-6888 (2001) are combined with rational design rules set forth in Reynolds et al., *Nature Biotech.,* 22(3):326-330 (2004).

Preferably, siRNA are chemically synthesized. The oligonucleotides that comprise the siRNA molecules of the invention can be synthesized using any of a variety of techniques known in the art, such as those described in Usman et al., *J. Am. Chem. Soc.,* 109:7845 (1987); Scaringe et al., *Nucl. Acids Res.,* 18:5433 (1990); Wincott et al., *Nucl. Acids Res.,* 23:2677-2684 (1995); and Wincott et al., *Methods Mol. Bio.,* 74:59 (1997). The synthesis of oligonucleotides makes use of common nucleic acid protecting and coupling groups, such as dimethoxytrityl at the 5'-end and phosphoramidites at the 3'-end. Alternatively, siRNA molecules can be assembled from two distinct oligonucleotides, wherein one oligonucleotide comprises the sense strand and the other comprises the antisense strand of the siRNA. For example, each strand can be synthesized separately and joined together by hybridization or ligation following synthesis and/or deprotection. In certain other instances, siRNA molecules can be synthesized as a single continuous oligonucleotide fragment, where the self-complementary sense and antisense regions hybridize to form an siRNA duplex having hairpin secondary structure.

In one embodiment, the oligonucleotide directed against ROR2 is a guide RNA comprising a guide RNA sequence and a tracr RNA. The guide RNA sequence is capable of hybridizing to a target sequence with the DNA sequence of an endogenous Ror2 gene. The tracr RNA is coupled to the guide RNA sequence. The guide RNA hybridises to the site within the Ror2 and targets a CRISPR-Cas enzyme to said site. In some embodiments, the guide sequence is between 10-30, or between 15-25, or between 15-20 nucleotides in length. Preferably the CRISPR-Cas enzyme is a Type II CRISPR enzyme, for example Cas-9. The enzyme complexes with the guide RNA. In one embodiment, the enzyme is active and acts as an endonuclease to cleave the DNA either via activation of the non-homologous end-joining or homologous DNA repair pathway, resulting in a blunt end cut or a nick. A repair template sequence can be supplied and be introduced into the allele by homologous recombination, thereby replacing the sequence that it targeted, such as a mutation in the DNA of an allele. In another embodiment, the enzyme is targeted to the DNA of the dominant mutant allele but the enzyme comprises one or more mutations that reduce or eliminate its endonuclease activity such that it does not edit the mutant allele but does prevent or reduce its transcription. In another embodiment, the enzyme can be engineered such that it is fused to a transcriptional repressor to reduce or disable its endonuclease function. The enzyme will be able to bind the guide RNA and be targeted to the DNA sequence, but no cleavage of the DNA takes place. The Ror2 gene may be suppressed, for example, by the shutting down of the promoter or blockage of RNA polymerase. In another embodiment, the transcription repressor may be bound to the tracr sequence. Functional domains can be attached to the tracr sequence by incorporating protein-binding RNA aptamer sequences, as described in Konermann et al (Genome-scale transcriptional activation by an engineered CRISPR-Cas9 complex, Nature, Vol 000, 2014). The transcription repressor-tracr sequence complex may be used to target other moieties to a precise gene location as desired.

The oligonucleotide of the invention may be conjugated with a peptide or receptor. To assist with delivery of the oligonucleotide, the peptide may for example be a cell penetrating peptide. This technique is described in, for example, WO2009/147368, WO2013/030569, WO2012/150960 and WO2004/097017.

In one embodiment, the oligonucleotides of the present invention may be conjugated to a carrier or encapsulated within a liposome. The present invention provides an siRNA of the invention conjugated to a carrier or encapsulated within a liposome. In one embodiment, the carrier is selected from the group consisting of atelocollagen, a lipid such as cholesterol, a biological polymer, and a metallic nanoparticle such as a gold nanoparticle.

The oligonucleotides of the invention may be complementary to a region of the RNA transcript from a Ror2 gene, e.g. an endogenous Ror2 gene. In one instance, the oligonucleotide will be complementary to 10, 11, 12, 13, 14, 15, 16, 17, 18, 19, 20, 21, 22, 23, 24, 25, 26, 27, 28, 29, or 30 nucleotides of that sequence, preferably complementary to 13-25 or 16-21 nucleotides of that sequence.

In one instance, the oligonucleotide of the invention is at least 10, 11, 12, 13, 14, 15, 16, 17, 18, 19, 20, 21, 22, 23, 24, 25, 26 or 27 nucleotides in length, preferably at least 19, 20, 21, 22, 23, 24, 25 or 26 nucleotides in length. In one embodiment, the oligonucleotide of the invention is between 10 and 35 nucleotides in length, for example, 10, 11, 12, 13, 14, 15, 16, 17, 18, 19, 20, 21, 22, 23, 24, 25, 26, 27, 28, 29, 30, 31, 32, 33, 34, 35 nucleotides in length. In one embodiment, the oligonucleotide of the invention is between 18 and 30 nucleotides in length, for example, 18, 19, 20, 21, 22, 23, 24, 25, 26, 27, 28, 29 30 nucleotides in length. In one embodiment, the oligonucleotide of the invention is 21 nucleotides in length. In one embodiment, the oligonucleotide of the invention is 29 nucleotides in length. It may be that the region of the oligonucleotide capable of hybridisation to is that length, or at least that length, but there are also additional nucleotides at the 5' and/or 3' ends of the oligonucleotide, though in other instances the overall length of the oligonucleotide is that number of nucleotides.

In general, oligonucleotide sequences which are perfectly complementary to a portion of the target RNA may preferably be employed. In some instances though sequence variations that might be expected due to genetic mutation, strain polymorphism, or evolutionary divergence may be present. For example, oligonucleotide sequences with insertions, deletions, and single point mutations relative to the target sequence may also be effective for inhibition. Greater than 70% sequence identity (or complementarity), e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% sequence identity, between the oligonucleotide sequence and the target RNA, e.g., target pre-mRNA, is preferred.

Sequence identity, including determination of sequence complementarity for nucleic acid sequences, may be determined by sequence comparison and alignment algorithms known in the field. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=# of identical positions/total # of positions*100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) *Proc. Natl. Acad. Sci. USA* 87:2264-68, modified as in Karlin and Altschul (1993) *Proc. Natl. Acad. Sci. USA* 90:5873-77. Such an algorithm is incorporated into the BLAST programs (version 2.0) of Altschul, et al. (1990) *J. Mol. Biol.* 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) *Nucleic Acids Res.* 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, *CABIOS* (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

siRNA and shRNA Directed Against ROR2

The present invention relates to siRNA and shRNA directed against ROR2 and therapeutic uses thereof in treating and/or preventing cartilage loss, treating and/or preventing osteoarthritis, treating and/or preventing osteoarthritis associated pain, promoting cartilage repair, and/or preventing cartilage degradation.

In one embodiment, the ROR2 inhibitor of the present invention is a siRNA, which comprises a sequence selected from the group consisting of:
  (i) 5' AAGUCUACAAAGGUCACCUGU 3' (SEQ ID NO: 1), a fragment comprising at least 10 contiguous nucleotides of SEQ ID NO:1, and variants thereof having up to three nucleotide substitutions;
  (iii) 5' AAGUCUACAAAGGUCACCUGUCCUGUCUC 3' (SEQ ID NO: 2) a fragment comprising at least 10 contiguous nucleotides of SEQ ID NO: 2, and variants thereof having up to three nucleotide substitutions;
  (iii) 5' AAACAGGUGACCUUUGUAGAC 3' (SEQ ID NO: 3), a fragment comprising at least 10 contiguous nucleotides of SEQ ID NO: 3, and variants thereof having up to three nucleotide substitutions;
  (iv) 5' AAACAGGUGACCUGUAGACCCUGUCUC 3' (SEQ ID NO: 4), a fragment comprising at least 10 contiguous nucleotides of SEQ ID NO: 4, and variants thereof having up to three nucleotide substitutions; and
  (v) nucleotide sequences complementary to any one of SEQ ID NOs:1-4, nucleotide sequences complementary to fragment comprising at least 10 contiguous nucleotides of SEQ ID NOs: 1-4, and variants thereof having up to three nucleotide substitutions.

In one embodiment, the ROR2 inhibitor for use according to claim 4 or 11, wherein the siRNA comprises the sequences of:
  (i) 5' AAGUCUACAAAGGUCACCUGU 3' (SEQ ID NO: 1), a fragment comprising at least 10 contiguous nucleotides of SEQ ID NO: 1, or a variant thereof having up to three nucleotide substitutions; and
  (ii) 5' AAACAGGUGACCUUUGUAGAC 3' (SEQ ID NO: 3), a fragment comprising at least 10 contiguous nucleotides of SEQ ID NO: 3, or a variant thereof having up to three nucleotide substitutions.

Any siRNA of the invention may further comprise the nucleotide sequence of CCUGUCUC at the 3' end. The incorporation of this sequence allows facilitates synthesis of the siRNA.

The oligonucleotides of the present invention, including the siRNA and the shRNA of the present invention, may be conjugated to a carrier or encapsulated within a liposome. Thus, the present invention provides an siRNA of the invention which is conjugated to a carrier or which is encapsulated within a liposome. In one embodiment, the carrier is selected from the group consisting of atelocollagen, a lipid such as cholesterol, a biological polymer, and a metallic nanoparticle such as a gold nanoparticle.

As discussed in Example 5, the present inventors have used an siRNA-Atelocollagen conjugate directed against ROR2 to silence the ROR2 gene in vivo in Example 5. Atelocollagen-conjugated siRNA proved to be extremely efficient in engaging with its target within cartilage, where the dense, avascular extracellular matrix impedes efficient penetration of many synthetic or natural biomolecules.

Thus, in one embodiment, the siRNA of the present invention is conjugated to Atelocollagen. Atelocollagen is a highly purified pepsin-treated type I collagen. Collagen is a fibrous protein in the connective tissue that plays an important role in the maintenance of the morphology of tissues and organs. A collagen molecule has an amino acid sequence called as telopeptide at both N- and C-terminals, which confers most of the collagen's antigenicity. Atelocollagen obtained by pepsin treatment is low in immunogenicity because it lacks telopeptides, and it is used clinically for a wide range of purposes, including wound-healing, vessel prosthesis and also as a bone cartilage substitute and hemostatic agent. Atelocollagen displays low-toxicity and low-immunogenicity when it is transplanted in vivo. The use of Atecollagen as a carrier for delivery of siRNA is discussed in more detail in Minakuchi et al. 2004 (Nucleic Acids Res. 2004; 32(13): e109).

In another aspect, the present invention provides a shRNA directed against ROR2 comprising a polynucleotide sequence selected from the group consisting of:
(i) 5' GGUUCACGACUGCGAAUCCAGGACCUGGA 3' (SEQ ID NO: 15), a fragment comprising at least 10 contiguous nucleotides of SEQ ID NO: 15, and variants thereof having up to three nucleotide substitutions;
(ii) 5' AAGACCAUUACCGCCACUGGCGUCCUGUU 3' (SEQ ID NO: 16), a fragment comprising at least 10 contiguous nucleotides of SEQ ID NO: 16, and variants thereof having up to three nucleotide substitutions;
(iii) 5' AUGGAUUACAGAGGAACGGCAAGCACCAC 3' (SEQ ID NO: 17), a fragment comprising at least 10 contiguous nucleotides of SEQ ID NO: 17, and variants thereof having up to three nucleotide substitutions;
(iv) 5' AAGCAGAAGGCAUCUGCGUCCACACCGCA 3' (SEQ ID NO: 18), a fragment comprising at least 10 contiguous nucleotides of SEQ ID NO: 18, and variants thereof having up to three nucleotide substitutions;
(v) 5' CCUUGAGCAUGAUCUUCAGCUACUGUUCC 3' (SEQ ID NO: 19), a fragment comprising at least 10 contiguous nucleotides of SEQ ID NO: 19, and variants thereof having up to three nucleotide substitutions; and
(vi) nucleotide sequences complementary to any one of SEQ ID NOs: 15-19, nucleotide sequences complementary to fragment comprising at least 10 contiguous nucleotides of SEQ ID NOs: 15-19, and variants thereof having up to three nucleotide substitutions.

In another aspect, the present invention provides an shRNA of invention for use as a medicament. In another aspect, the present invention provides an shRNA directed against ROR2 for use in treating osteoarthritis and/or promoting cartilage repair and/or treating osteoarthritis associated pain in a subject. In one embodiment, the shRNA may delivered using a viral vector. The viral vector may be packaged with in a viral particle, for example, a lentiviral particle. An example of a lentiviral particle that may be used to deliver a shRNA directed against ROR2 is TL320439, which is commercially available from Origene.

Oligonucleotide Delivery

The oligonucleotides of the present invention, including the siRNAs of the invention and the shRNAs of the invention, may be introduced into cells using any suitable method. For instance transfection, electroporation, fusion, liposomes, extracellular vesicles (e.g. exosomes or microvesicles), colloidal polymeric particles, dendrimers and viral and non-viral vectors as well as other means known in the art may be used to deliver the oligonucleotide sequences to cells.

In some instances, the oligonucleotide is delivered using methods involving liposome-mediated uptake. Lipofectins and cytofectins are lipid-based positive ions that bind to negatively charged nucleic acid and form a complex that can ferry the nucleic acid across a cell membrane and may be employed. In one instance a lipofectin is used in the delivery of the oligonucleotide of the invention, particularly Lipofectamine 2000. In one instance the oligonucleotide may be delivered using a jetPRIME® reagent. For example, the oligonucleotide may be delivered to cells in vitro using at method involving jetPRIME® reagent. In some instances, no transfection reagents may be required and oligonucleotide may be taken up by target cells directly via gymnosis.

In one embodiment, the oligonucleotides of the invention may delivered using a composition comprising a dendrimer. Dendrimers are nano-sized, radially symmetric molecules with well-defined, homogeneous, and monodisperse structure that has a typically symmetric core, an inner shell, and an outer shell (Madaan et al. (2014) J Pharm Bioallied Sci. 2014 July-September; 6(3): 139-150). Any dendrimer may be suitable for delivery of olignoculetodies of the invention. The dendrimer for use with the oligonucleotides of the invention may comprise of consist of polyamidoamine (PAMAM), a poly(propylene imine) (PPI, poly-L-lysine, melamine, poly(etherhydroxylamine) (PEHAM), poly(esteramine) (PEA) and/or polyglycerol.

Delivery may be direct to the subject, or for instance to cells or tissues, for instance with the cells or tissues subsequently being reintroduced. Oligonucleotides of the invention may be directly introduced into a target cell or introduced extracellular into a cavity, interstitial space, into the circulation of a subject, introduced orally, or may be introduced by bathing a cell or organism in a solution containing the RNA using methods for introducing nucleic acid into cells in vivo.

In one embodiment, the ROR2 inhibitors or the siRNAs of the invention are delivered by intrarticular injection.

The oligonucleotides of the invention may be delivered by any suitable route of administration. In some instances, administration may be systemic, in others it may be localised. For instance, the oligonucleotides may be administered by direct injection at a tissue site or infusion into a body fluid. Vascular or extravascular circulation, the blood or lymph system, and the cerebrospinal fluid are examples of locations where the RNA may be introduced.

The oligonucleotides of the invention may be, for instance, delivered to the joint of a subject by any suitable method. In certain instances, the oligonucleotides can be delivered by transdermal methods. The oligonucleotide may also be delivered via an implantable device.

Physical methods of introducing oligonucleotide of the invention include injection of a solution containing the oligonucleotide of the invention, bombardment by particles covered by the oligonucleotide of the invention, soaking the cell or organism in a solution of the oligonucleotide of the invention, or electroporation of cell membranes in the presence of the oligonucleotide of the invention. A viral vector packaged into a viral particle can be used to achieve efficient introduction of the oligonucleotide of the invention into a cell and transcription of oligonucleotide of the invention encoded by the expression construct. Other methods known in the art for introducing nucleic acids to cells may be used, such as lipid-mediated carrier transport, chemical-mediated transport, such as calcium phosphate, and the like. The oligonucleotide of the invention may be introduced along with components that perform one or more of the following activities: enhance uptake of the oligonucleotide of the invention by a cell, inhibit annealing of single strands of oligonucleotide of the invention, stabilize single strands of oligonucleotide of the invention, prevent degradation of the oligonucleotide of the invention or other-wise increase inhibition of the target gene.

The oligonucleotides of the invention may be modified so that they target specific cells, for instance by binding to receptors found on a particular cell type. The oligonucleotides of the invention may be delivered to cells using a vector.

Vectors

The present invention also provides a vector comprising a nucleotide sequence encoding a ROR2 inhibitor of the invention or a siRNA of the invention. As used herein, the term "vector" refers to a molecule or construct suitable for delivering a nucleotide sequence encoding a ROR2 inhibitor or an siRNA of the invention to a target cell.

Viral Vectors

In one embodiment the vector is viral vector, optionally a viral vector selected from the group consisting of a lentiviral vector, a retroviral vector, and adeno-associated viral (AAV) vector. In one embodiment, the AAV vector is a self-complementary AAV (scAAV) vector. The viral vectors of the present invention may be derived or derivable from any suitable virus.

In one embodiment, the viral vector is a recombinant viral particle. A recombinant viral particle is capable of transducing a target cell with the nucleotide sequence encoding a ROR2 inhibitor or siRNA of the invention. For a retroviral particle, once within the cell the RNA genome from the vector particle is reverse transcribed into DNA and integrated into the genome of the target cell.

Lentiviral Vectors

Lentiviruses are part of a larger group of retroviruses. A detailed list of lentiviruses may be found in Coffin et al. (1997) "Retroviruses" Cold Spring Harbor Laboratory Press Eds: J M Coffin, S M Hughes, H E Varmus pp 758-763). In brief, lentiviruses can be divided into primate and non-primate groups. Examples of primate lentiviruses include but are not limited to: the human immunodeficiency virus (HIV), the causative agent of acquired immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV), feline immunodeficiency virus (FIV) and bovine immunodeficiency virus (BIV). Retroviruses—such as MLV—are unable to infect non-dividing or slowly dividing cells such as those that make up, for example, muscle, eye, brain, lung and liver tissue.

A lentiviral vector, as used herein, is a vector which comprises at least one component part derivable from a lentivirus. Preferably, that component part is involved in the biological mechanisms by which the vector infects cells, expresses genes or is replicated. The basic structure of retrovirus and lentivirus genomes share many common features such as a 5' LTR and a 3' LTR, between or within which are located a packaging signal to enable the genome to be packaged, a primer binding site, attachment sites to enable integration into a host cell genome and gag, pol and env genes encoding the packaging components—these are polypeptides required for the assembly of viral particles. Lentiviruses have additional features, such as rev and RRE sequences in HIV, which enable the efficient export of RNA transcripts of the integrated provirus from the nucleus to the cytoplasm of an infected target cell.

In the provirus, the viral genes are flanked at both ends by regions called long terminal repeats (LTRs). The LTRs are responsible for transcription by serving as enhancer-promoter sequences and polyadenylation signals thereby controlling the expression of the viral genes. The LTRs themselves are identical sequences that can be divided into three elements, which are called U3, R and U5. U3 is derived from the sequence unique to the 3' end of the RNA. R is derived from a sequence repeated at both ends of the RNA and U5 is derived from the sequence unique to the 5' end of the RNA. The sizes of the three elements can vary considerably among different viruses.

In a replication-defective lentiviral vector genome gag, pol and env may be absent or not functional.

In a typical lentiviral vector of the present invention, at least part of one or more protein coding regions essential for replication may be removed from the virus. This makes the viral vector replication-defective. Portions of the viral genome may also be replaced by a nucleotide sequence encoding a ROR2 inhibitor or siRNA of the invention in order to generate a vector comprising an nucleotide sequence encoding a ROR2 inhibitor or siRNA of the invention which is capable of transducing a target non-dividing host cell and/or integrating its genome into a host genome.

In one embodiment the lentiviral vectors are non-integrating vectors as described in WO 2007/071994. In a further embodiment the vectors have the ability to deliver a sequence which is devoid of or lacking viral RNA. In a further embodiment a heterologous binding domain (heterologous to gag) located on the RNA to be delivered and a cognate binding domain on gag or pol can be used to ensure packaging of the RNA to be delivered. Both of these vectors are described in WO 2007/072056.

The lentiviral vector may be a "non-primate" vector, i.e., derived from a virus which does not primarily infect primates, especially humans.

The viral vector may be derived from EIAV. In addition to the gag, pol and env genes EIAV encodes three other genes: tat, rev, and S2. Tat acts as a transcriptional activator of the viral LTR (Derse and Newbold (1993) Virology 194(2):530-536 and Maury et al (1994) Virology 200(2):632-642) and Rev regulates and coordinates the expression of viral genes through rev-response elements (RRE) (Martarano et al. (1994) J Virol 68(5):3102-3 111). The mechanisms of action of these two proteins are thought to be broadly similar to the analogous mechanisms in the primate viruses (Martarano et al. (1994) J Virol 68(5):3102-3111). The function of S2 is unknown. In addition, an EIAV protein, Ttm, has been identified that is encoded by the first exon of tat spliced to the env coding sequence at the start of the transmembrane protein (Beisel et al. (1993) J Virol 67(2):832-842).

The term "recombinant lentiviral vector" refers to a vector with sufficient lentiviral genetic information to allow packaging of an RNA genome, in the presence of packaging components, into a viral particle capable of infecting a target cell. Infection of the target cell may include reverse transcription and integration into the target cell genome. The recombinant lentiviral vector carries non-viral coding sequences which are to be delivered by the vector to the target cell, for example non-viral coding sequences which encoded an ROR2 inhibitor or an siRNA of the invention. A recombinant lentiviral vector is incapable of independent replication to produce infectious lentiviral particles within the final target cell. Usually the recombinant lentiviral vector lacks a functional gag-pol and/or env gene and/or other genes essential for replication. The recombinant lentiviral vector of the present invention may have a minimal viral genome.

Anti-ROR2 Antibodies

The present invention relates to antibodies that bind to ROR2, referred to herein as anti-ROR2 antibodies. The invention also relates to uses for such antibodies, such as therapeutic uses of for treating and/or preventing cartilage loss and/or treating and/or preventing osteoarthritis, treating and/or preventing osteoarthritis associated pain, promoting cartilage repair, and/or preventing cartilage degradation.

The antibodies preferably specifically bind to ROR2, that is they bind to ROR2 but they do not bind, or bind at a lower affinity, to other molecules. The term ROR2 as used herein may refer to human ROR2. Alternatively, the term ROR2 as used herein may refer to non-human ROR2, such as murine ROR2.

The sequence of a human ROR2 protein is set out in SEQ ID NO: 5. The sequence of a murine ROR2 protein is set out in SEQ ID NO: 7. An antibody of the present invention may have binding affinity for ROR2 from other mammals, for example ROR2 from primates or rodents e.g. mice or rats.

In one embodiment, antibodies of the invention block a function of ROR2, such anti-ROR2 antibodies may be referred to as "blocking antibodies" or "blocking anti-ROR2 antibodies". These terms may used interchangeably.

Blocking of ROR2 encompasses any reduction in at least one activity or function of ROR2 that results in, for example, stimulating chondrocyte differentiation associated (which is associated with increased expression of chondrocytic differentiation markers e.g. COL2A1, AGGRECAN, and/or ERG) decreased expression of Col1A1 and/or ColX, decreased expression of collagen degrading enzymes ADAMTS-4 and ADAMTS-5, increased expression of GAG, reduction in OA associated pain.

For example, blocking of ROR2 may be achieved by blocking the interaction with activating ligands such as members of the Wnt family (e.g. Wnt5a, Wnt3a, Wnt1, Wnt11, Wnt4 and Wnt16), blocking the interaction between an ROR2 protein and a members of an ROR2 receptor complex, or by blocking ROR2's interaction with downstream intracellular targets, such as 14-3-3beta scaffold protein. For example, the anti-ROR2 antibodies of the invention may block one or more the following:

(a) the interaction between an ROR2 protein and one or more activating ligands such as Wnt family members (e.g. Wnt5a, Wnt3a, Wnt1, Wnt11, Wnt4 and Wnt16);

(b) the interaction between an ROR2 protein and a members of an ROR2 receptor complex, for example the interaction between a first ROR2 protein and a second ROR2 protein, and/or the interaction between an ROR2 protein and an ROR1 protein, a frizzled receptor protein and/or a scaffold protein (e.g. a syndecan);

(c) the interaction between ROR2 interaction with downstream targets, such as 14-3-3beta scaffold protein, which may reduce or prevent the capacity of ROR2 to phosphorylate said downstream target protein (e.g. 14-3-3beta).

Blocking of ROR2 may result in decreased transcription of an endogenous Ctgf gene, Yap gene, and/or Taz gene. Blocking of ROR2 may result in decreased expression of an endogenous CTGF protein, YAP protein or TAZ protein.

Blocking encompasses both total and partial reduction of an activity or function of ROR2. For example, a blocking anti-ROR2 antibody of the invention may totally or partially reduce:

(a) the interaction between an ROR2 protein and one or more activating ligands such as Wnt family members (e.g. Wnt5a, Wnt3a, Wnt1, Wnt11, Wnt4 and Wnt16);

(b) the interaction between an ROR2 protein and a members of an ROR2 receptor complex, for example the interaction between a first ROR2 protein and a second ROR2 protein, and/or the interaction between an ROR2 protein and an ROR1 protein, a frizzled receptor protein and/or a scaffold protein (e.g. a syndecan);

(c) the interaction between ROR2 interaction with downstream targets, such as 14-3-3beta scaffold protein, which may reduce or prevent the capacity of ROR2 to phosphorylate said downstream target protein (e.g. 14-3-3beta). An anti-ROR2 antibody of the present invention may also totally or partially block the transcription of an endogenous Ctgf gene, Yap gene, and/or Taz gene expression of an endogenous CTGF protein. For example, an anti-ROR2 antibody of the invention may reduce an activity or function of ROR2 by from 10 to 50%, at least 50% or at least 70%, 80%, 90%, 95% or 99%.

Blocking of ROR2 activity or function can be measured by any suitable means. For example, blocking of the Wnt5a/ROR2 interaction can be determined by measuring the effect on ROR2 tyrosine phosphorylation and/or 14-3-3beta scaffold protein, on the basis that ROR2 tyrosine phosphorylation and 14-3-3beta scaffold protein phosphorylation is characteristic of an activated Wnt5a/ROR2 signalling pathway. Blocking of ROR2 activity can also be determined using a kinase assay in which ROR2 dependent phosphorylation of a synthetic substrate of ROR2 e.g. a short peptide derived from a natural substrate, such as Vangl2, is measured. For example, phosphorylation of Vangl2 may be measured by western blot. Blocking of ROR2 activity can also be measured by staining cells cultured in the presence or absence of ROR2 inhibitor with Alcian Blue and/or by determining the expression of Aggrecan by cells cultured in the presence or absence of ROR" inhibitor.

The terms "binding activity" and "binding affinity" are intended to refer to the tendency of an antibody molecule to bind or not to bind to a target. Binding affinity may be quantified by determining the dissociation constant (Kd) for an antibody and its target. Similarly, the specificity of binding of an antibody to its target may be defined in terms of the comparative dissociation constants (Kd) of the antibody for its target as compared to the dissociation constant with respect to the antibody and another, non-target molecule.

In one embodiment, the anti-ROR2 antibody of the invention does not bind to ROR1, i.e. the anti-ROR2 antibody does not cross react with ROR1.

Typically, the Kd for the antibody with respect to the target will be 2-fold, preferably 5-fold, more preferably 10-fold less than Kd with respect to the other, non-target molecule such as unrelated material or accompanying material in the environment. More preferably, the Kd will be 50-fold less, even more preferably 100-fold less, and yet more preferably 200-fold less.

The value of this dissociation constant can be determined directly by well-known methods, and can be computed even for complex mixtures by methods such as those, for example, set forth in Caceci et al. (Byte 9:340-362, 1984). For example, the Kd may be established using a double-filter nitrocellulose filter binding assay such as that disclosed by Wong & Lohman (Proc. Natl. Acad. Sci. USA 90, 5428-5432, 1993).

One method for the evaluation of binding affinity for ROR2 is by ELISA. Other standard assays to evaluate the binding ability of ligands such as antibodies towards targets are known in the art, including for example, Western blots, RIAs, and flow cytometry analysis. The binding kinetics (e.g., binding affinity) of the antibody also can be assessed by standard assays known in the art, such as surface plasmon resonance, for example by Biacore™ system analysis.

The binding affinity of an antibody of the invention to its target can be measured by methods known to the person skilled in the art, for example by surface plasmon resonance. A type of surface plasmon resonance is Biacore. Preferably the antibody of the invention has a binding affinity for ROR2 of 1 nM or less. Preferably the antibody of the invention has a binding affinity for ROR2 of 0.5 nM or less, 0.1 nM or less, 50 pM or less, 10 pM or less, 5 pM or less or 2 pM or less.

A competitive binding assay can be conducted in which the binding of the antibody to the target is compared to the binding of the target by another, known ligand of that target, such as another antibody. The concentration at which 50% inhibition occurs is known as the Ki. Under ideal conditions, the Ki is equivalent to Kd. The Ki value will never be less than the Kd, so measurement of Ki can conveniently be substituted to provide an upper limit for Kd.

An antibody of the invention may specifically bind to ROR2. "Specifically binding" means that an antibody binds to ROR2 with greater affinity than to another target. An antibody of the invention is preferably capable of binding to its target with an affinity that is at least two-fold, 10-fold, 50-fold, 100-fold or greater than its affinity for binding to another non-target molecule.

In one embodiment an anti-ROR2 antibody of the invention binds to an epitope within SEQ ID NO: 5 or an amino acid sequence having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9% sequence identity to SEQ ID NO: 5. In one embodiment, an anti-ROR2 antibody of the invention binds to an epitope within SEQ ID NO: 7 or an amino acid sequence having at at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9% sequence identity to SEQ ID NO: 7.

In one embodiment, an anti-ROR2 antibody of the invention binds to the extracellular portion of ROR2. In one embodiment, an anti-ROR2 antibody of the invention binds to a domain of the extracellular portion of ROR2. In one embodiment, an anti-ROR2 antibody of the invention binds to the Ig domain, the CRD or the Kringle domain of ROR2. In one embodiment, an anti-ROR2 antibody of the invention binds to the CRD of ROR2.

In one embodiment, an anti-ROR2 antibody of the invention binds to an epitope within the extracellular portion of ROR2. In one embodiment, an anti-ROR2 antibody of the invention binds to an epitope within a domain of the extracellular portion of ROR2. In one embodiment, an anti-ROR2 antibody of the invention binds to an epitope within the Ig domain, the CRD or the Kringle domain of ROR2. In one embodiment, an anti-ROR2 antibody of the invention binds to an epitope within the CRD of ROR2. In one embodiment, an anti-ROR2 antibody of invention binds to an epitope within the amino acid sequence of SEQ ID NO: 10 or an amino acid sequence having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9% sequence identity to SEQ ID NO: 10. In one embodiment, the anti-ROR2 antibody of the invention binds to an epitope within SEQ ID NO: 12 or an amino acid sequence having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9% sequence identity to SEQ ID NO: 10.

In one embodiment, an anti-ROR2 antibody of the invention binds to an epitope with an amino acid sequence encoded by a polynucleotide comprising the nucleotide sequence of SEQ ID NO: 11 or a nucleotide sequence having or an amino acid sequence having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9% sequence identity to SEQ ID NO: 11. In one embodiment, an anti-ROR2 antibody of the invention binds to an epitope with an amino acid sequence encoded by a polynucleotide comprising the nucleotide sequence of SEQ ID NO: 13 or a nucleotide sequence having or an amino acid sequence having at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9% sequence identity to SEQ ID NO: 13. The epitope sequence may comprise between 5 to 30, 5 to 25, 5 to 20, 5 to 15, or 5 to 10 contiguous amino acids of SEQ ID NOs: 5, 7, 10 or 12.

An anti-ROR2 antibody of the invention may bind to an epitope sequence of 5 to 30, 5 to 25, 5 to 20, 5 to 15, or 5 to 10 amino acids in length. For example, an anti-ROR2 antibody of the invention may bind to an epitope sequence of 5, 6, 7, 8, 9, 10, 11, 12, 13, 14 or 15 amino acids in length.

As used herein, the term "epitope" generally refers to the site on a target antigen which is recognised by an immune receptor such as an antibody. Preferably it is a short peptide derived from or as part of a protein. Epitopes can be identified from knowledge of the amino acid and corresponding DNA sequences of the peptide, as well as from the nature of particular amino acids (e.g., size, charge, etc.) and the codon dictionary, without undue experimentation. See, e.g., Ivan Roitt, Essential Immunology, 1988; Janis Kuby, Immunology, 1992 e.g., pp. 79-81.

The location of an epitope may be identified by routine methods. For example, the general location of an epitope may be determined by assessing the ability of an antibody to bind to different fragments or variant ROR2 polypeptides. The specific amino acids within ROR2 that make contact with an antibody may also be determined using routine methods. For example, the antibody and target molecule may be combined and the antibody/target complex may be crystallised. The crystal structure of the complex may be determined and used to identify specific sites of interaction between the antibody and its target.

An antibody of the invention may bind to the same epitope or region as another antibody of the invention. For example, where an antibody of the invention is known, other antibodies of the invention may be identified by comparing their binding to ROR2 with that of the known antibody.

The antibody of the invention may comprise a heavy chain and/or a light chain.

An antibody of the invention may have the ability to cross-compete with another antibody of the invention for binding to ROR2 as described herein. Such cross-competing antibodies can be identified based on their ability to cross-compete with a known antibody of the invention in standard binding assays. For example, BIAcore analysis, ELISA assays or flow cytometry may be used to demonstrate cross-competition. Such cross-competition may suggest that the two antibodies bind to the same or similar epitopes.

An antibody of the invention may therefore be identified by a method that comprises a binding assay which assesses whether or not a test antibody is able to cross-compete with a known antibody of the invention for a binding site on the target molecule. Methods for carrying out competitive binding assays are well known in the art. For example they may involve contacting together a known antibody of the invention and a target molecule under conditions under which the antibody can bind to the target molecule. The antibody/target complex may then be contacted with a test antibody and the extent to which the test antibody is able to displace the antibody of the invention from antibody/target complexes may be assessed. An alternative method may involve contacting a test antibody with a target molecule under conditions that allow for antibody binding, then adding an antibody of the invention that is capable of binding that target molecule and assessing the extent to which the antibody of the invention is able to displace the test antibody from antibody/target complexes.

The ability of a test antibody to inhibit the binding of an antibody of the invention to the target demonstrates that the test compound can compete with an antibody of the invention for binding to the target and thus that the test antibody binds to the same epitope or region on the ROR2 protein as the known antibody of the invention. A test antibody that is identified as cross-competing with a known antibody of the invention in such a method is also a potential antibody according to the present invention. The fact that the test antibody can bind ROR2 in the same region as a known antibody of the invention and cross-compete with the known antibody of the invention suggests that the test antibody may act as a ligand at the same binding site as the known antibody and that the test antibody may therefore mimic the action of the known antibody.

The known antibody of the invention may be an antibody as described herein, such as one of the ROR2 antibodies as described herein or any variant or fragment thereof as described herein that retains the ability to bind to ROR2. An antibody of the invention may bind to the same epitope as one or more of the antibodies as described herein or any variant or fragment thereof as described herein that retains the ability to bind to ROR2.

Specific binding may be assessed with reference to binding of the antibody to a molecule that is not the target. This comparison may be made by comparing the ability of an antibody to bind to the target and to another molecule. This comparison may be made as described above in an assessment of Kd or Ki. The other molecule used in such a comparison may be any molecule that is not the target molecule. Preferably the other molecule is not identical to the target molecule. Preferably the target molecule is not a fragment of the target molecule.

The term "antibody" as referred to herein includes whole antibodies and any antigen binding fragment (i.e., "antigen-binding portion") or single chains thereof. An antibody refers to a glycoprotein comprising at least two heavy (H) chains and two light (kappa)(L) chains inter-connected by disulfide bonds, or an antigen binding portion thereof. Each heavy chain is comprised of a heavy chain variable region (abbreviated herein as VH) and a heavy chain constant region. Each light chain is comprised of a light chain variable region (abbreviated herein as VL) and a light chain constant region. The variable regions of the heavy and light chains contain a binding domain that interacts with an antigen. The VH and VL regions can be further subdivided into regions of hypervariability, termed complementarity determining regions (CDR), interspersed with regions that are more conserved, termed framework regions (FR). The constant regions of the antibodies may mediate the binding of the immunoglobulin to host tissues or factors, including various cells of the immune system (e.g., effector cells) and the first component (Clq) of the classical complement system.

An antibody of the invention may be a monoclonal antibody or a polyclonal antibody. In one embodiment, an antibody of the invention is a monoclonal antibody. Polyclonal antibodies are antibodies that are derived from different B cell lines. A polyclonal antibody may comprise a mixture of different immunoglobulin molecules that are directed against a specific antigen. The polyclonal antibody may comprise a mixture of different immunoglobulin molecules that bind to one or more different epitopes within an antigen molecule. Polyclonal antibodies may be produced by routine methods such as immunisation with the antigen of interest. For example a mouse capable of expressing human antibody sequences may be immunised with human ROR2. Blood may be subsequently removed and the Ig fraction purified.

Monoclonal antibodies are immunoglobulin molecules that are identical to each other and have a single binding specificity and affinity for a particular epitope. Monoclonal antibodies (mAbs) of the present invention can be produced by a variety of techniques, including conventional monoclonal antibody methodology, for example those disclosed in "Monoclonal Antibodies; A manual of techniques", H Zola (CRC Press, 1988) and in "Monoclonal Hybridoma Antibodies: Techniques and Application", SGR Hurrell (CRC Press, 1982).

The anti-ROR2 antibody of the present invention may be a murine antibody, a rabbit antibody, a goat antibody, a camelid antibody (e.g. a llama antibody), a chimeric antibody, a humanized antibody or a human antibody.

The term "antigen-binding portion" of an antibody refers to one or more fragments of an antibody that retain the ability to specifically bind to an antigen, such as ROR2. It has been shown that the antigen-binding function of an antibody can be performed by fragments of a full-length antibody. Examples of binding fragments encompassed within the term "antigen-binding portion" of an antibody include a Fab fragment, a F(ab')2 fragment, a Fab' fragment, a Fd fragment, a Fv fragment, a dAb fragment and an isolated complementarity determining region (CDR). Single chain antibodies such as scFv and heavy chain antibodies such as VHH and camel antibodies are also intended to be encompassed within the term "antigen-binding portion" of an antibody. These antibody fragments may be obtained using conventional techniques known to those of skill in the art, and the fragments may be screened for utility in the same manner as intact antibodies.

Antibodies of the invention can be tested for binding to the target protein by, for example, standard ELISA or Western blotting. An ELISA assay can also be used to screen for hybridomas that show positive reactivity with the target protein. The binding specificity of an antibody may also be determined by monitoring binding of the antibody to cells expressing the target protein, for example by flow cytometry.

The specificity of an antibody of the invention for target protein may be further studied by determining whether or not the antibody binds to other proteins. For example, where it is desired to produce an antibody that specifically binds ROR2 or a particular part, e.g. epitope, of ROR2, the specificity of the antibody may be assessed by determining whether or not the antibody also binds to other molecules or modified forms of ROR2 that lack the part of interest.

Once a suitable antibody has been identified and selected, the amino acid sequence of the antibody may be identified by methods known in the art. The genes encoding the antibody can be cloned using degenerate primers. The antibody may be recombinantly produced by routine methods.

A "polypeptide" is used herein in its broadest sense to refer to a compound of two or more subunit amino acids, amino acid analogs, or other peptidomimetics. The term "polypeptide" thus includes short peptide sequences and also longer polypeptides and proteins. As used herein, the term "amino acid" refers to either natural and/or unnatural or synthetic amino acids, including glycine and both the D or L optical isomers, and amino acid analogs and peptidomimetics.

Isolated Cells

The present invention also provides an isolated cell comprising an ROR2 inhibitor, an oligonucleotide, a siRNA and/or a vector of the present invention. The present invention also relates to the therapeutic uses of such isolated cells in treating and/or preventing cartilage loss and/or treating and/or preventing osteoarthritis, treating and/or preventing osteoarthritis associated pain, promoting cartilage repair, and/or preventing cartilage degradation.

Also described herein is the use of inhibitors of ROR2 in methods of enhancing the capacity of autologous cell preparations to produce cartilage in vivo.

Thus, in one aspect, the present invention provides a method for enhancing the capacity of a cell to produce cartilage. In one embodiment, the method is an in vitro method. In one embodiment, the method is an ex-vivo. In one embodiment, the in vitro method enhances the capacity of cells to produce cartilage following administration to patient.

Cells of the present invention or cells that may be used in the methods of the present invention may be selected from the group consisting of: differentiated cells, non-differentiated cells, for example stem cells, such as pluripotent stem cells, multipotent stem cells, induced pluripotent stem cells, mesenchymal stem cells (MSCs). In one embodiment, the cells of the invention are MSCs. The MSCs may be condensing MSCs. MSCs can be stimulated to differentiate into condensing stem cells by contacting the MSCs with one or more growth or differentiation factors, such as one or more factors selected from the group consisting of bone morphogenetic protein (BMP)-5a, BMP-5b, fibroblast growth factor (FGF)-4, FGF-8, FGF-10, FGF basic, N-cadherin, Neural cell adhesion molecule (NCAM), Perlecan, transforming growth factor (TGF)-beta 1, TGF-beta 2 and Veriscan.

In one embodiment, the cells of the invention are chondrocytes. Chondrocytes are cells found in cartilage, which produce and maintain the cartilaginous matrix. Condensing MSC can be stimulated to differentiate into chondrocytes by contacting the condensing MSC with one or more growth or differentiation factors, such as a one or more factors selected from the group consisting of BMP-2, BMP-4, BMP-5 BMP-7, growth differentiation factor (GDF)-5/BMP-14, FGF basic, insulin-like growth factor 1 (IGF-1), TGF-beta 1 and TGF-beta 2.

Pharmaceutical Composition

The present invention also provides a pharmaceutical composition comprising an ROR2 inhibitor of the invention, a siRNA of the invention, a vector of the invention, or an isolated cell of the invention. The pharmaceutical composition will also typically comprise a pharmaceutically acceptable carrier or excipient. The pharmaceutical composition may be formulated to help it be compatible with its intended route of administration.

Examples of routes of administration which may be employed in the invention, and which in some cases include parenteral, e.g., intra-articular, intravenous, intradermal, subcutaneous, intraperitoneal, intramuscular, oral (e.g., inhalation), transdermal (topical), transmucosal, administration may be employed. The pharmaceutical compositions, ROR2 inhibitors, oligonucleotides, anti-ROR2 antibody, siRNA, vectors, or isolated cells of the invention may be, for instance, delivered by such routes. The pharmaceutical compositions of the invention may be formulated to aid compatibility with any of the preceding routes of administration. A preferred route for delivery for the pharmaceutical compositions, ROR2 inhibitors, oligonucleotides, anti-ROR2 antibodies, siRNA, vectors, or isolated cells of the invention is via intra-articular administration. In one embodiment, the intra-articular administration is via intra-articular injection or infusion (also known as joint injection or infusion).

In one embodiment, the pharmaceutical compositions, ROR2 inhibitors, oligonucleotides, anti-ROR2 antibodies, siRNAs, vectors, or isolated cells of the invention are delivered intra-articularly by a slow release implant. Where a patient is suffering from cartilage loss or a related disorder, such as osteoarthritis, of a knee joint, the slow release implant may be implanted into the infrapatellar fat pad of the knee of the patient. In one embodiment, the slow release implant is configured to control the release rate of the ROR2 inhibitor, the oligonucleotide, the anti-ROR2 antibody, the siRNA, the vectors, or the isolated cells of the invention are delivered intra-articularly. The slow release implant may comprise a carrier portion to encapsulate the ROR2 inhibitor, the oligonucleotide, the anti-ROR2 antibody, the siRNA, the vectors, or the isolated cells of the invention. In one embodiment, carrier portion comprises atelocollagen.

Pharmaceutical compositions of the invention, including in particular solutions or suspensions used for parenteral, intradermal, subcutaneous or intra-articular application, may, for example, include the following components: a sterile diluent such as water for injection, saline solution, fixed oils, polyethylene glycols, glycerine, propylene glycol or other synthetic solvents; antibacterial agents such as benzyl alcohol or methyl parabens;

antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. Possible excipients may in some instances be selected from water, salt solutions, alcohol, polyethylene glycols, gelatin, lactose, amylase, magnesium stearate, talc, silicic acid, viscous paraffin, hydroxymethylcellulose and polyvinylpyrrolidone. The pH of the composition may be adjusted with acids or bases, such as hydrochloric acid or sodium hydroxide. The composition, for instance a composition for parenteral preparation, may be enclosed in ampoules, disposable syringes or multiple dose vials made of glass or plastic. In a preferred instance, a composition of the invention has a physiological pH.

Pharmaceutical compositions suitable for injectable use, for example suitable for use in intra-articular injection, include sterile aqueous solutions (where water soluble) or dispersions and sterile powders for the extemporaneous preparation of sterile injectable solutions or dispersion. For suitable carriers may include physiological saline, bacteriostatic water, Cremophor EL™ (BASF, Parsippany, N.J.) or phosphate buffered saline (PBS). The compositions will typically be sterile.

As used herein, "pharmaceutically acceptable carrier" includes any and all solvents, dispersion media, coatings, antibacterial and antifungal agents, isotonic and absorption delaying agents, and the like that are physiologically compatible. The carrier may be suitable for parenteral, e.g. intra-articular, intravenous, intramuscular or subcutaneous administration (e.g., by injection or infusion). The carrier may be particularly suitable for intra-articular administration. Depending on the route of administration, an anti-ROR2 antibody of the invention may be coated in a material to protect the antibody from the action of acids and other natural conditions that may inactivate or denature the antibody.

Preferred pharmaceutically acceptable carriers comprise aqueous carriers or diluents. Examples of suitable aqueous carriers that may be employed in the pharmaceutical compositions of the invention include water, buffered water and saline. Examples of other carriers include ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. In many cases, it will be preferable to include isotonic agents, for example, sugars, polyalcohols such as mannitol, sorbitol, or sodium chloride in the composition.

A pharmaceutical composition of the invention also may include a pharmaceutically acceptable anti-oxidant. These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Therapeutic compositions typically must be sterile and stable under the conditions of manufacture and storage. The composition can be formulated as a solution, microemulsion, liposome, or other ordered structure suitable to high drug concentration.

Sterile injectable solutions can be prepared by incorporating the active agent (e.g. antibody) in the required amount in an appropriate solvent with one or a combination of ingredients enumerated above, as required, followed by sterilization microfiltration. Generally, dispersions are prepared by incorporating the active agent into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active agent plus any additional desired ingredient from a previously sterile-filtered solution thereof.

Pharmaceutical compositions of the invention may comprise one or more one or more ROR2 inhibitors, siRNAs, vectors, or isolated cells of the invention. Pharmaceutical compositions of the invention may comprise additional active ingredients as well one or more ROR2 inhibitors, siRNAs, vectors, or isolated cells of the invention. They may also comprise additional therapeutic or prophylactic agents. The additional therapeutic agents or prophylactic agents may be useful for treating or preventing osteoarthritis and/or promoting cartilage repair and/or treating or preventing osteoarthritis associated pain.

Pharmaceutical compositions comprising oligonucleotides of the invention encompass any pharmaceutically acceptable salts, esters, or salts of such esters of the oligonucleotide. In certain instances, a composition of the invention may include more than one oligonucleotide directed against ROR2 of the invention. Accordingly, for example, the disclosure is also drawn to pharmaceutically acceptable salts, prodrugs, pharmaceutically acceptable salts of such prodrugs, and other bioequivalents may also be employed. Suitable pharmaceutically acceptable salts include, but are not limited to, sodium and potassium salts. A prodrug may, for instance, include the incorporation of additional nucleosides at one or both ends of an oligomeric compound which are cleaved by endogenous nucleases within the body, to form the active oligonucleotide.

Administration may be, for instance, by inhalation. Systemic administration may be, for instance, by transmucosal or transdermal means. Transmucosal administration can be accomplished through the use of nasal sprays or suppositories. For transdermal administration, the oligonucleotides may be, for instance, formulated into a transdermal patches or plasters, ointments, salves, gels, or creams. The oligonucleotides may be, for instance, prepared in the form of suppositories or retention enemas. In some instances, the oligonucleotides may be formulated with carriers that protect the compound against rapid elimination from the body, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, and polylactic acid.

In one embodiment, the pharmaceutical compositions may be formulated in unit dosage forms. In some embodiments the compositions may be formulated in ampoules. The pharmaceutical compositions may be included in a container, pack, or dispenser together with instructions for administration.

The present invention also provides a kit comprising one or more ROR2 inhibitors, siRNAs, vectors, or isolated cells of the invention and optionally instructions for administration to a subject for treating osteoarthritis and/or promoting cartilage repair and/or treating osteoarthritis associated pain, preferably such a kit has the one or more ROR2 inhibitors, siRNAs, vectors, or isolated cells of the invention provided in the form of a pharmaceutical composition of the invention. The kit may also include means for administering the one or more ROR2 inhibitors, siRNAs, vectors, or isolated cells of the invention or pharmaceutical composition, for instance a syringe or other appropriate delivery device. The kit may comprise any of the means of delivery discussed herein. In one instance, the kit also comprises lipofectin and in particular an oligonucleotide of the invention formulated with lipofectin. The kit may comprise an ROR2 inhibitor, an oligonucleotide, an siRNA, a vectors, of the invention together with a slow release implant, for example a slow release implant, which comprises a carrier portion comprising atelocollagen.

The dosage of the ROR2 inhibitors, siRNAs, vectors, or isolated cells of the invention to be administered will depend upon the particular method or route of delivery being carried out, and when it is being administered to a subject, the nature of disease, the condition of the subject, the particular formulation, and the route of administration. Examples of intracellular concentrations for the oligonucleotides of the invention include those in the range from about 0.005 to 50 µM, or more preferably 0.02 to 5 µM. For administration to a subject such as a human, a daily dosage ranging from about 0.001 to 50 mg/kg, preferably 0.01 to 10 mg/kg, and more preferably from 0.1 to 5 mg/kg may be employed. The skilled person and particularly an appropriate physician will be able to identify an appropriate dosage, for instance taking factors such as age, sex, weight and so on into account.

Dosage regimens may be adjusted to provide the optimum desired response (e.g., a therapeutic response). For example, a single dose may be administered, several divided doses may be administered over time or the dose may be proportionally reduced or increased as indicated by the exigencies of the therapeutic situation. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Administration may be in single or multiple doses. Multiple doses may be administered via the same or different routes and to the same or different locations. Alternatively, doses can be via a sustained release formulation, in which case less frequent administration is required. Dosage and frequency may vary depending on the half-life of the one or more ROR2 inhibitors, siRNAs, vectors, or isolated cells of the invention in the subject and the duration of treatment desired.

Methods of Treatment and Diagnostic or Predictive Methods

The present invention also provides a method of treating and/or preventing cartilage loss, treating and/or preventing osteoarthritis, treating and/or preventing osteoarthritis associated pain, promoting cartilage repair, or preventing cartilage degradation, the method comprising administering to a subject in need thereof one or more ROR2 inhibitors, siRNAs, vectors, or isolated cells of the invention.

In addition, the present invention provides a ROR2 inhibitor for use in treating and/or preventing cartilage loss, treating and/or preventing osteoarthritis, treating and/or preventing osteoarthritis associated pain, promoting cartilage repair, or preventing cartilage degradation in a subject, wherein the inhibitor is an anti-ROR2 antibody or fragment thereof or an oligonucleotide directed against ROR2

The present invention also provides a method of diagnosing a subject with cartilage loss, osteoarthritis, osteoarthritis associated pain and/or cartilage degradation comprising the step of: determining the expression level and/or the activity of ROR2 in a sample previously obtained from the subject. The present invention also provides a method for predicting that a subject has increased susceptibility to cartilage loss, osteoarthritis, osteoarthritis associated pain and/or cartilage comprising the step of (i) determining the expression level and/or the activity of ROR2 in a sample previously obtained from the subject.

In some embodiments, the subject may be a human subject. In some embodiments, the subject may be a non-human subject. The subject may have been previously diagnosed as having cartilage loss, osteoarthritis, osteoarthritis associated pain and/or cartilage degradation. The subject may be at risk for developing cartilage loss, osteoarthritis, osteoarthritis associated pain and/or cartilage degradation, for example, the subject may have been previously determined to carry genetic markers which indicate that the subject has a higher risk of developing cartilage loss, osteoarthritis, osteoarthritis associated pain and/or cartilage degradation. The subject may be suspected of having OA. The subject may be undergoing treatment for cartilage loss, osteoarthritis, osteoarthritis associated pain and/or cartilage degradation. For example, the subject may be undergoing treatment with one or more ROR2 inhibitors, such as an ROR2 inhibitor of the present invention. The subject may have sustained an injury or trauma or have undergone a surgical intervention putting them at a higher risk of developing cartilage loss, osteoarthritis, osteoarthritis associated pain and/or cartilage degradation. For example, the subject may have previously undergone surgery to treat an anterior cruciate ligament (ACL) injury or an injury, such as a tear, to a knee meniscus. The subject may be an elderly subject. For example, the subject may be at least 40, at least 45, at least 50, at least 55, at least 60, at least 65, at least 70, at least 75, at least 80 at least 85, at least 90, or at least 95 years in age. The subject may be a female subject.

In one embodiment, the subject is may be female.

The subject may be unresponsive to other methods or composition for treating and/or preventing cartilage loss, osteoarthritis, osteoarthritis associated pain and/or cartilage degradation. For example, the subject may be unresponsive to treatment with a NSAID or an opioid analgesic.

In one embodiment, the method treatment of the invention ameliorates OA associated pain. Pain is typically measured and monitored using self administered questionnaires such as the WOMAC, IKDC, Lysholm, KOOS, Oxford Knee score and similar validated scoring systems (Collins et al. (2015) Arthritis Care Res (Hoboken). 2011 November; 63(0 11): S208-S228). Such scoring systems assess both pain and function with several sub-scores. More pain-focussed scoring systems can also be used to separate different components of pain such as pain at weight bearing from allodynia or central sensitization (for instance PainDETECT and S-LANSS; Moreton et al. (2015) Arthritis Care & Research Volume 67, Issue 4, pages 519-528, April 2015). Functional tests such as Timed 'Up & Go' or 'Stair climbing test' as described in Baert I, et al. Knee Surgery, Sports Traumatology, Arthroscopy, 2014. The present invention is further illustrated by the following examples which should not be construed as further limiting.

EXAMPLES

Example 1—Materials and Methods

Overexpression and siRNA Transfection

Human and mouse ROR2 were knocked down using siRNA, at a final concentration of 20 nM in complete DMEM using jetPRIME transfection reagent (Polyplus) according to the manufacturer's instructions. A Stealth RNAi negative control duplex of medium guanine-cytosine (GC) content (Life Technologies) or a scrambled sequence with the same GC content as the target siRNA was used as a negative control.

Micromass Culture and Alcian Blue Staining

Cells were resuspended at a density of $1 \times 10^7$ cells/mL in complete medium, and micromass cultures were obtained by pipetting 15 µL drops of cell suspension into each well of a 24 well plate. The cells were allowed to attach for 3h and then 1 mL of complete medium was added (with stimulation if indicated). Micromasses were cultured for 3 days. Micromasses were harvested for RT-PCR gene expression analysis or fixed and whole-mount stained with Alcian blue. Alcian blue extraction and quantification was performed as previously described. Images were acquired at room temperature with Leica microscope.

SUPER8XTopflash Assay

Co-transfected with SUPER8XTOPFlash TCF/LEF-firefly luciferase reporter plasmid and CMV-Renilla luciferase plasmid using JetPRIME transfection reagent (Polyplus). The cells were stimulated for 24h before luciferase activity was measured using the Dual luciferase Reporter assay system (Promega).

Validation Experiments

Atelocollagen-siRNA injected intra articularly. Mice were killed after 5 or 7 days; femoral condyles were processed for histology, all tissues between menisci and tibial growth plate taken for western blot.

Histological Analysis and OA Scoring

Histological processing and histomorphometrical analysis were performed as described elsewhere (Nalesso et al., 2016). All images were taken using the same settings on an Olympus microscope. Mice with <3 intact sections for histomorphometrical analysis were excluded (1 from each group). One mouse from the control group was identified using Grubb's test for outliers in R (p=0.04137; Grubbs, 1950, 1969), and was removed from analyses because it had not developed OA.

Statistical Analysis

Parametric data were compared with the t test, non-parametric data with the Wilcoxon-Mann-Whitney test. For multiple comparisons, the analysis of variance or Kruskal-Wallis test, including the appropriate post-hoctest, was used. p Values <0.05 were considered significant: *p<0.05; p<0.01; *p<0.001.

Figure 1B:
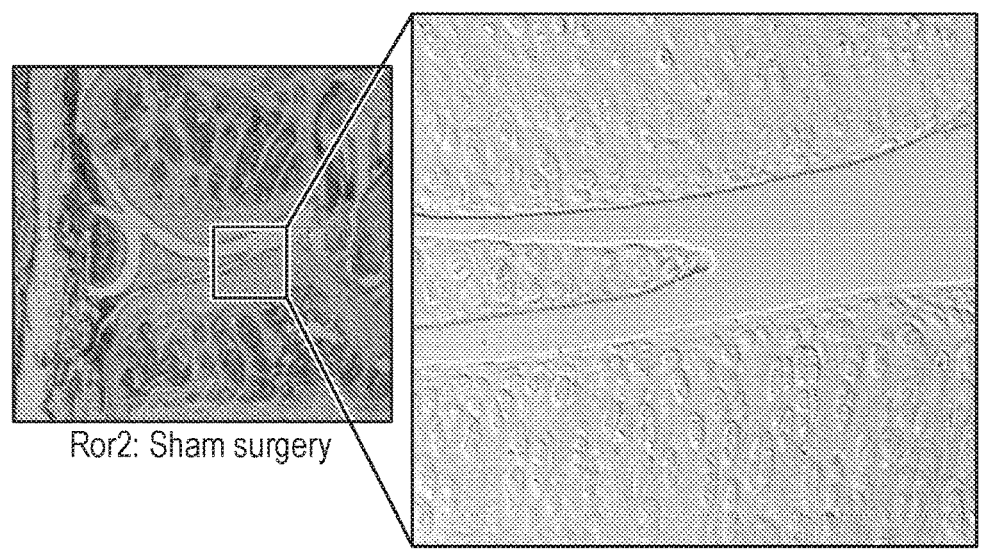
Figure 1B:
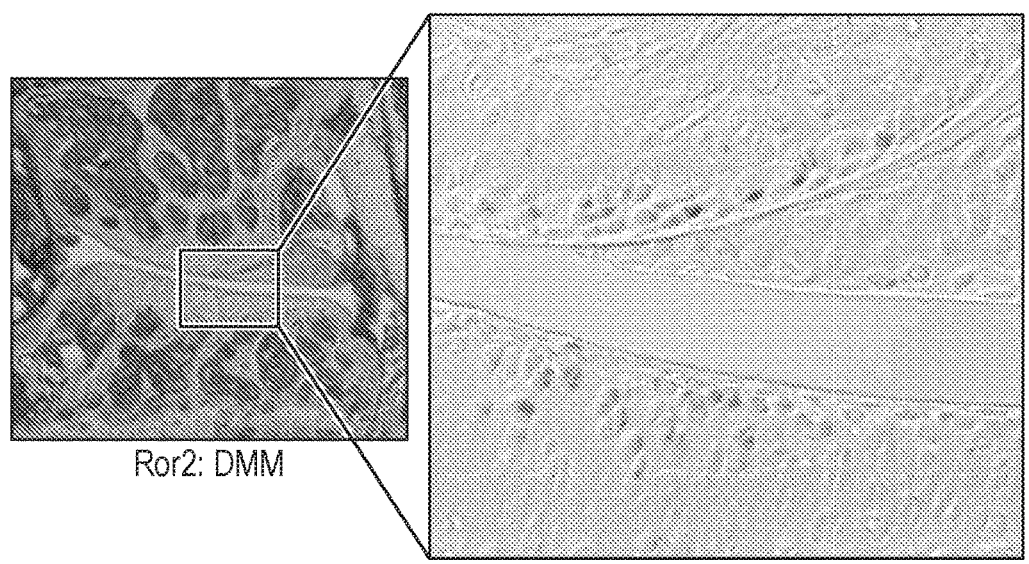
Figure 1B:
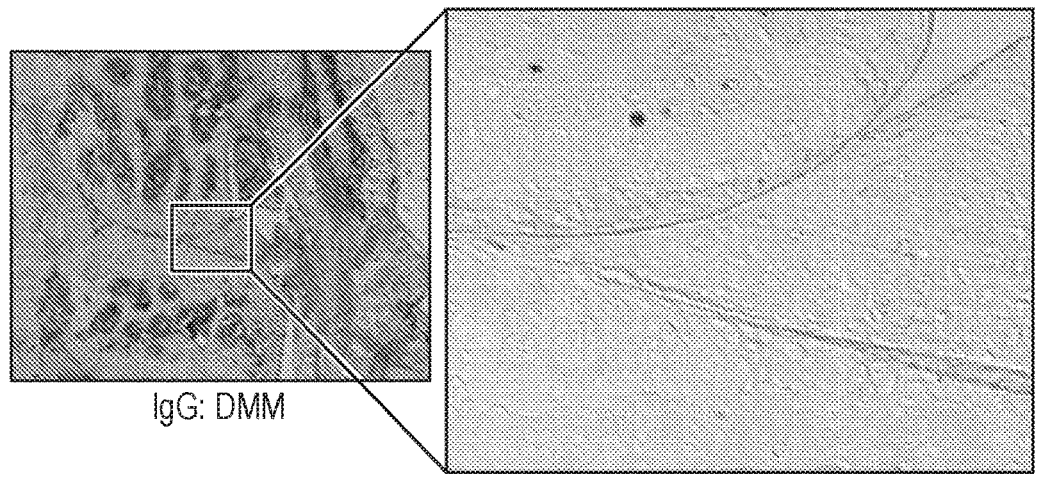
Figure 1C:
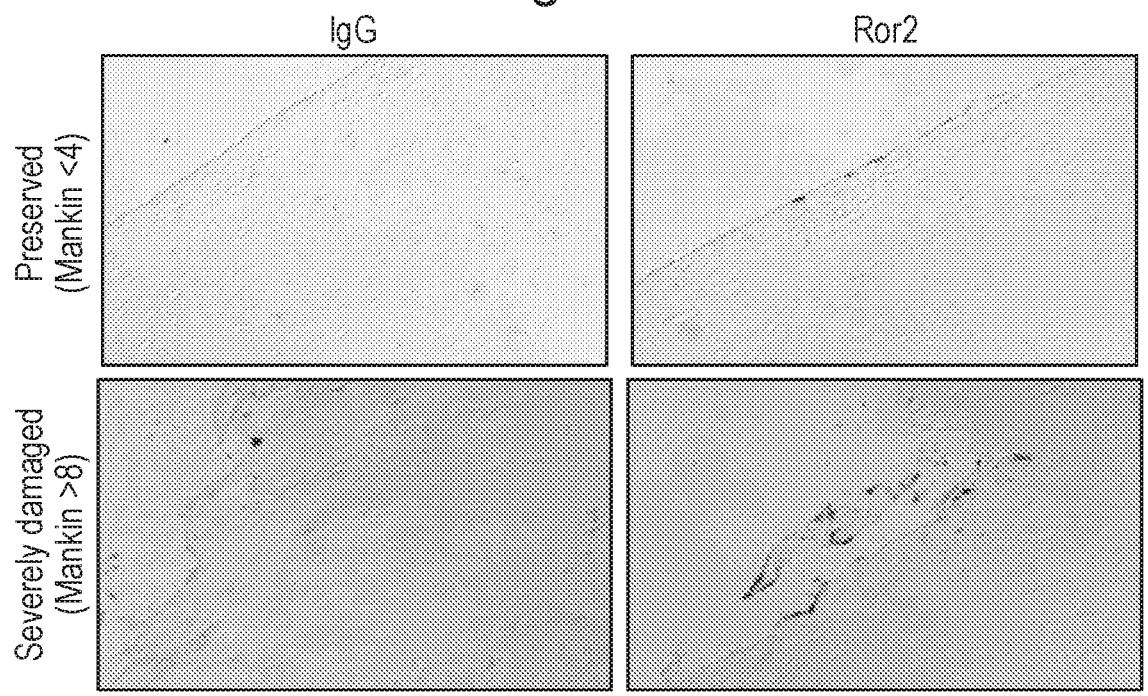
Figure 1D:
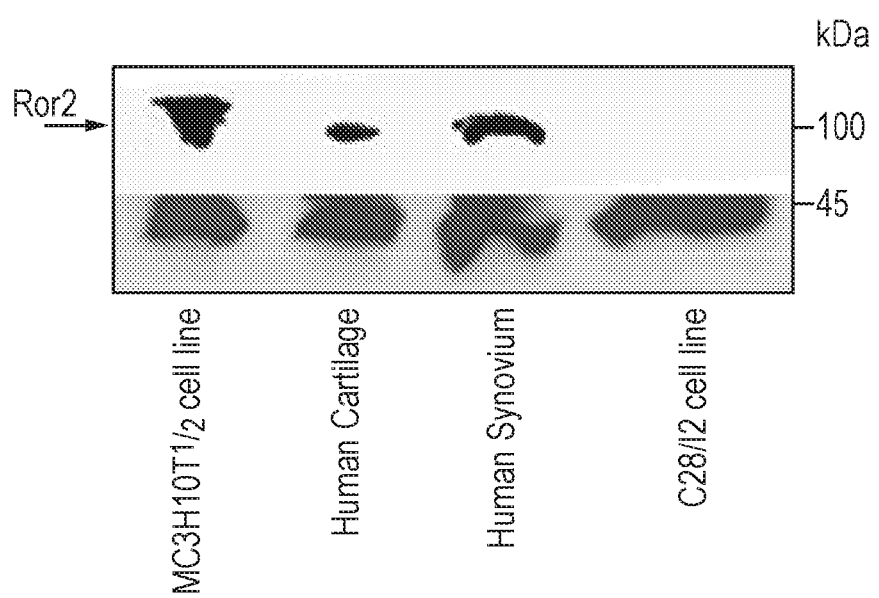

Example 2—ROR2 is not Detectable in Normal Cartilage and is Upregulated in Osteoarthritis ROR2 was detected in the most superficial cartilage layer of the articular cartilage in mouse embryos at stage 18.5 dpc (FIG. 1A). Postnatally, no ROR2 was detectable by immunofluorescence in resting conditions, however, 1 week after inducing osteoarthritis by joint destabilization, ROR2 became detectable in the upper ⅓ of the articular cartilage (FIG. 1B). To confirm ROR2 expression in humans, we compared severely damaged with relatively preserved areas of articular cartilage obtained from subjects undergoing total joint replacement. ROR2 was hardly detectable in preserved cartilage areas but consistently present in areas with high cartilage damage. ROR2 expression in human cartilage and synovial membrane was also confirmed by Western blotting (FIGS. 1C and D).

Example 3—ROR2 Overexpression Inhibits Chondrocytic Differentiation

Figure 2A:
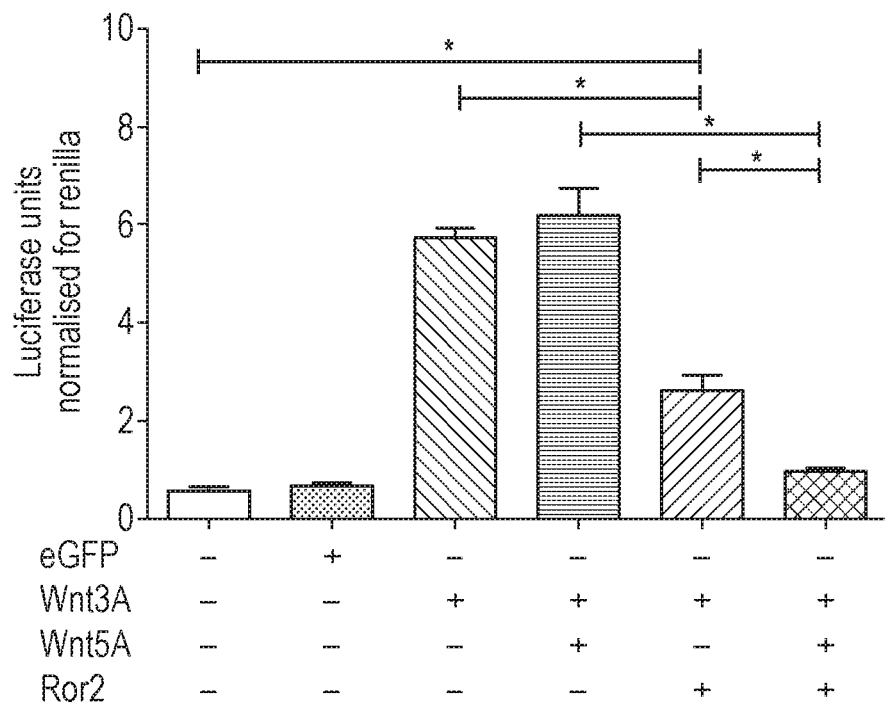
FIG. 2. ROR2 overexpression inhibits chondrocytic differentiation. (A) Results of a luciferase assay in HEK293 cells showing that co-stimulation with WNT-5A enhanced the capacity of ROR2 to inhibit WNT-3A-induced activation of WNT signalling (B) Results of a luciferase assay in MC3H10T1/2 cells showing that ROR2 overexpression inhibits WNT signalling. (C) Results of a luciferase assay showing that ROR2 overexpression did not inhibit the capacity of the GSK3 beta-inhibitor BIO to activate WNT signalling. (D) Comparison of BMP-2 induced chondrocytic differentiation of MC3H10T1/2 cells in the presence and absence of ROR2 (as measured by alcian blue staining for glycosaminoglycans). (E) Comparison of expression levels for the chondrocytic differentiation markers COL2A1 and ACAN FIG. 3. ROR2 loss of function supports chondrocytic differentiation. (A) In vitro ROR2 expression levels in response to siRNA-induced silencing of ROR2. (B) Ror2 mRNA expression levels in response to shRNA-lentivirus directed against Ror2 mRNA. (C) ROR2 protein expression levels in response to shRNA-lentivirus directed against Ror2 mRNA. (D) siRNA silencing of ROR2 is sufficient to drive chondrocytic differentiation of MC3H10T1/2 cells (in the absence of BMP-2) as assessed by Alcian blue staining. (E) shRNA-lentivirus silencing of ROR2 is sufficient to drive chondrocytic differentiation of MC3H10T1/2 cells (in the absence of BMP-2) as assessed by Alcian blue staining. (F) siRNA silencing of ROR2 resulted in induction of ACAN (aggrecan) mRNA expression. (G) shRNA-lentivirus silencing of ROR2 strongly inhibited expression of the key cartilage degrading enzymes ADAMTS-4 and ADAMTS-5. (H) Luciferase assay showing that ROR2 silencing did not result in an increase of the activation of the luciferase assay reporter by WNT-3A.
Figure 2B:
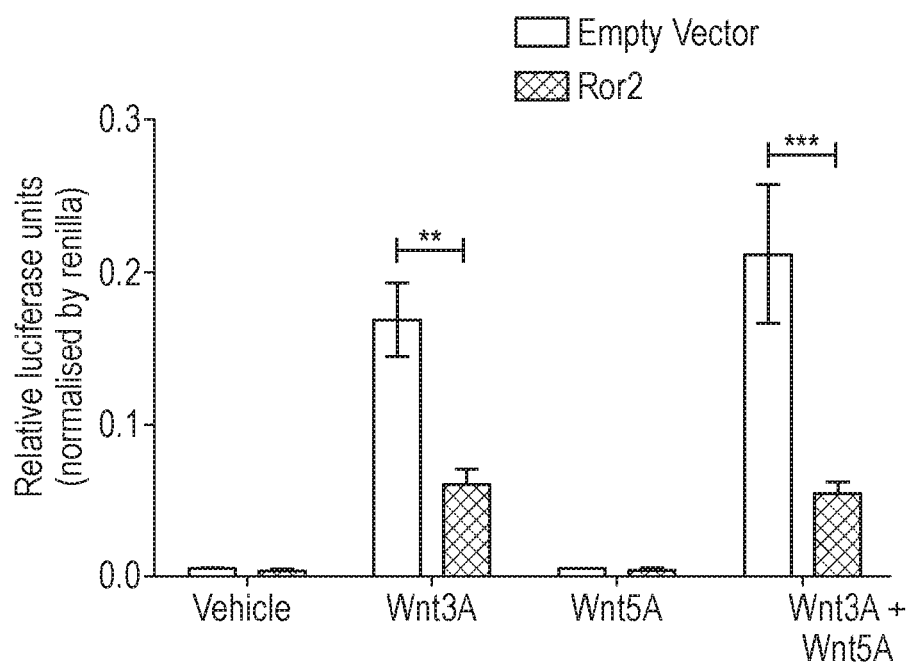
Figure 2C:
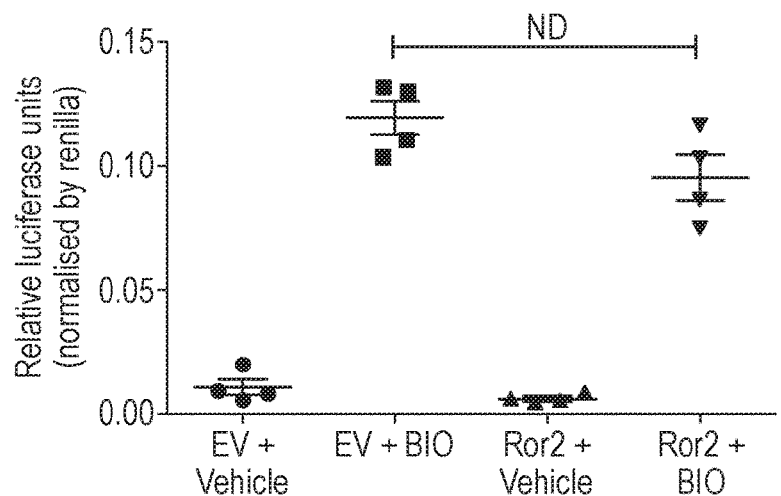

To investigate if the levels of ROR2 influence the degree of chondrocytic differentiation we performed gain of function studies on mesenchymal cell lines. First, to validate the activity of a ROR2 mammalian expression plasmid we confirmed that, in keeping with previous literature, overexpression of ROR2 in HEK293 cells inhibited the capacity of WNT3A to activate canonical WNT signalling as assessed by a luciferase reporter assay. As expected, co-stimulation with WNT-5A enhanced the capacity of ROR2 to inhibit WNT-3A-induced activation of WNT signalling (FIG. 2A). The WNT inhibitory effect of ROR2 overexpression was confirmed in the mesenchymal cell line MC3H10T1/2 (FIG. 2B). ROR2 overexpression did not inhibit the capacity of the GSK3 beta-inhibitor BIO to activate WNT signalling, thereby suggesting that the inhibitory effect is upstream of GSK3 beta (FIG. 2C).

Figure 2D:
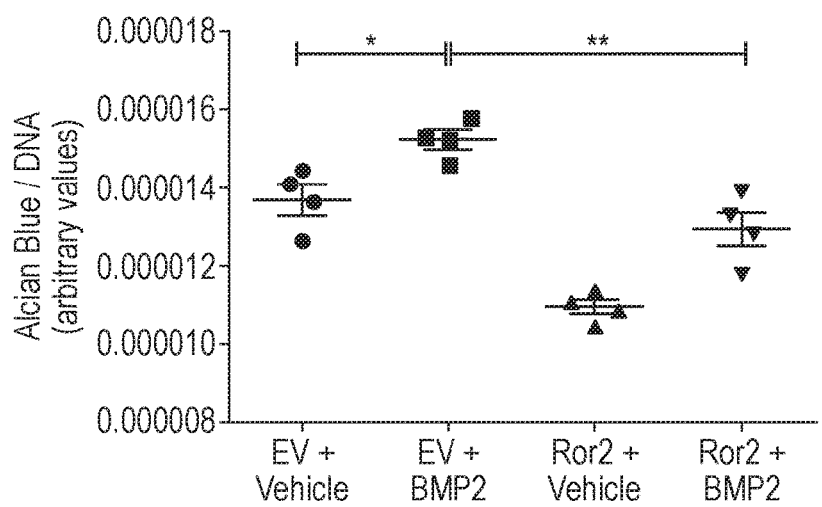
Figure 2D:
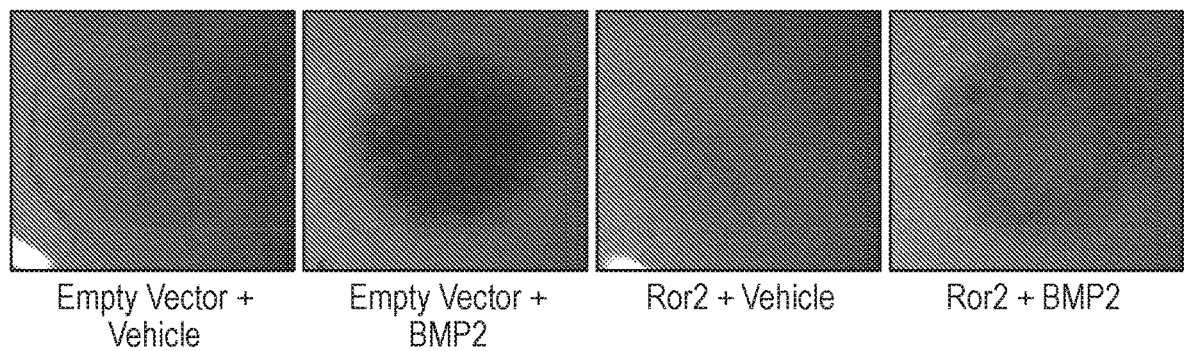
Figure 2E:
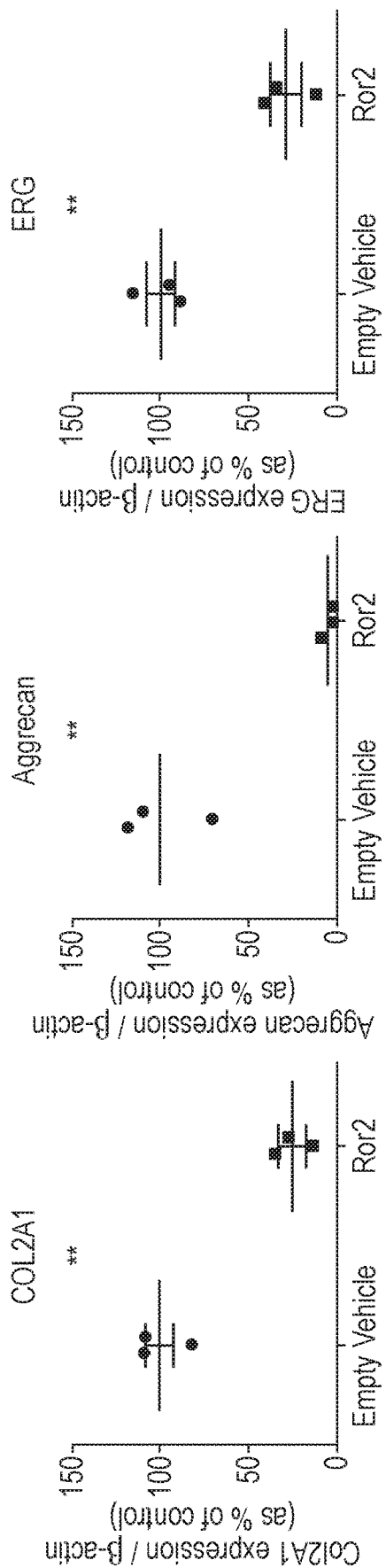
Figure 2F:
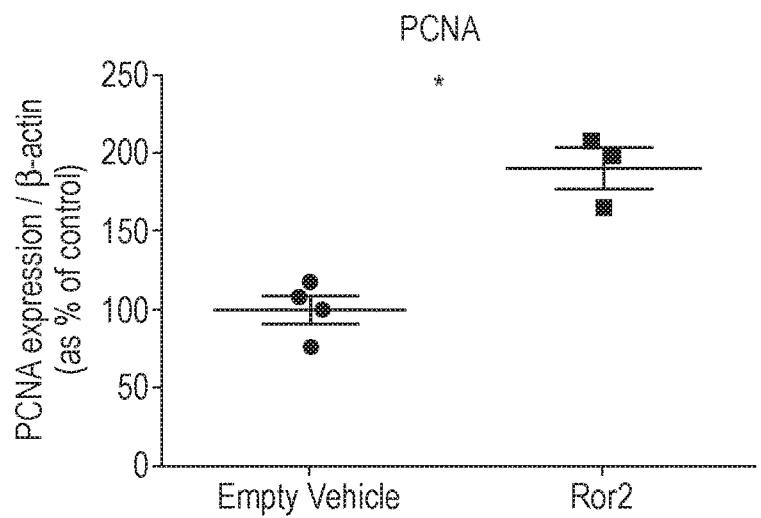

We then tested whether ROR2 overexpression modulated the capacity of MC3H10T1/2 cells to differentiate in response to bone morphogenetic protein 2 (BMP-2) (Denker et al., 1999). As expected, BMP-2 induced rapid chondrocytic differentiation of MC3H10T1/2 as assessed by Alcian blue staining. ROR2 overexpression inhibited chondrogenic differentiation of MC3H10T1/2 cells in response to BMP-2 (FIG. 2D) and the expression of the chondrocytic differentiation markers COL2A1, ACAN and ERG (FIG. 2E). ROR2 overexpression also upregulated the proliferation marker PCNA (FIG. 2F).

Example 4—ROR2 Loss of Function Supports Chondrocytic Differentiation

Figure 3A:
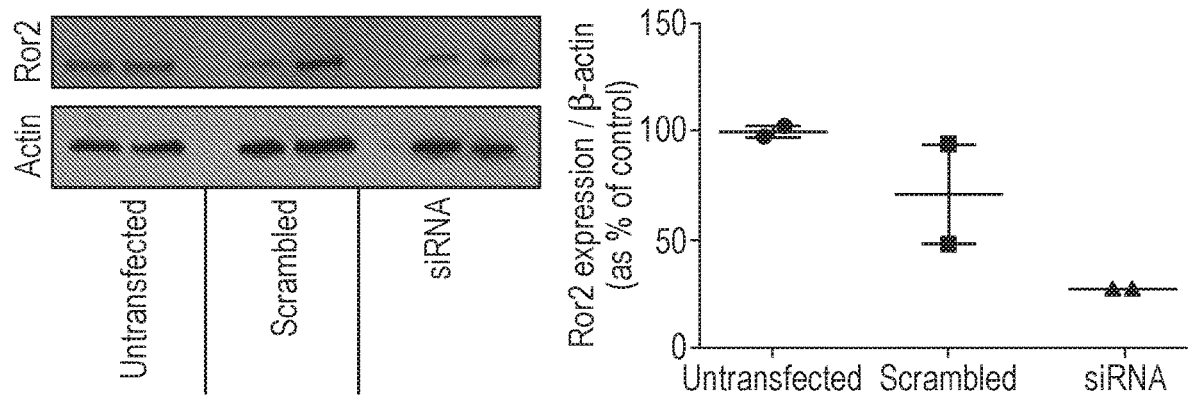
Figure 3B:
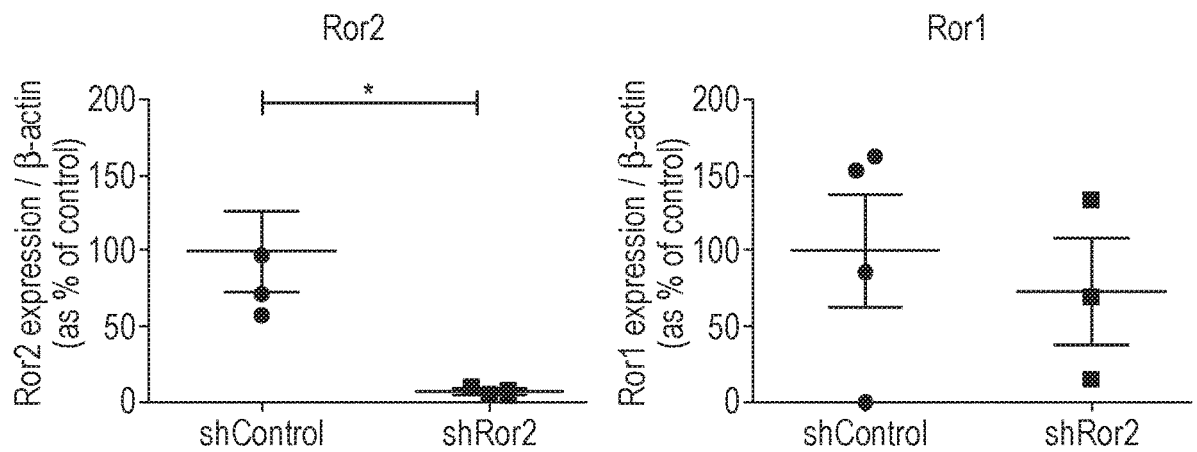
Figure 3C:
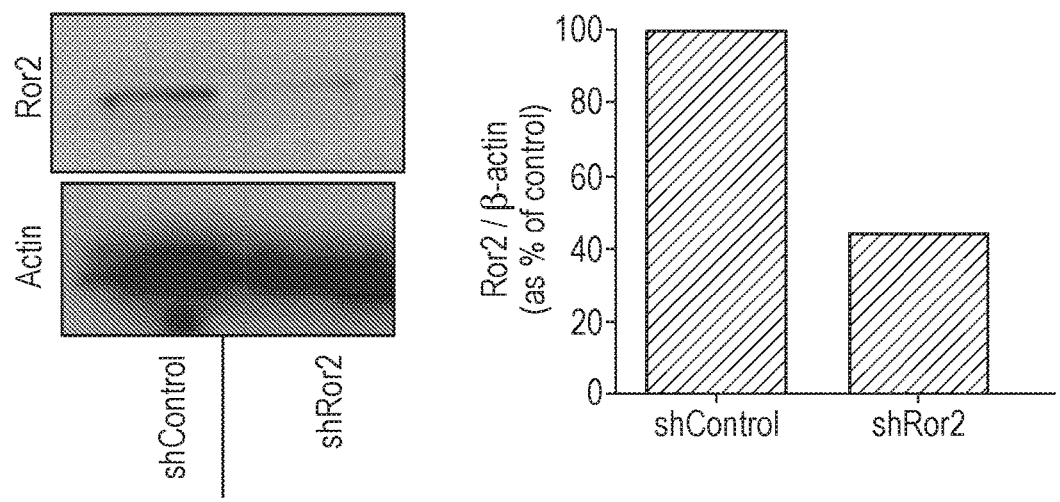
Figure 3D:
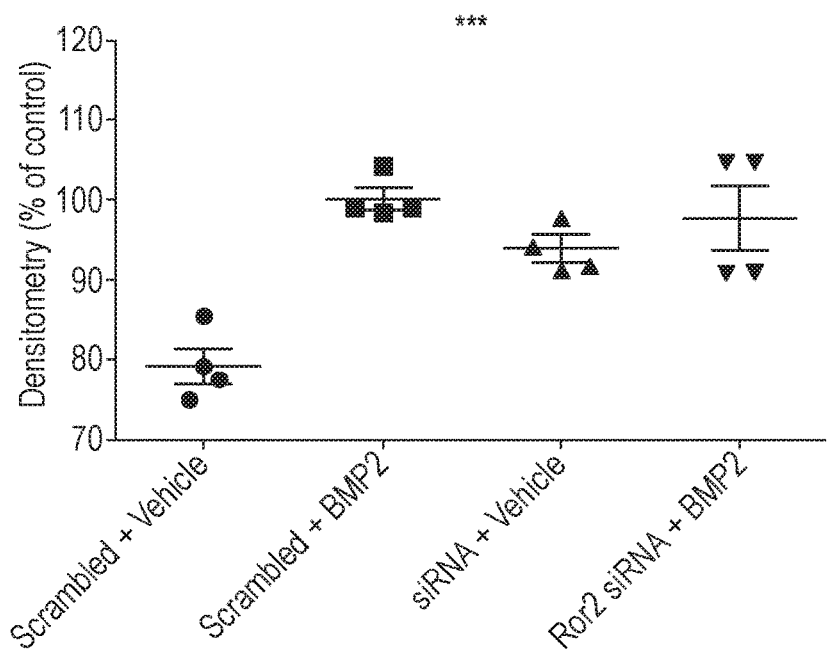
Figure 3D:
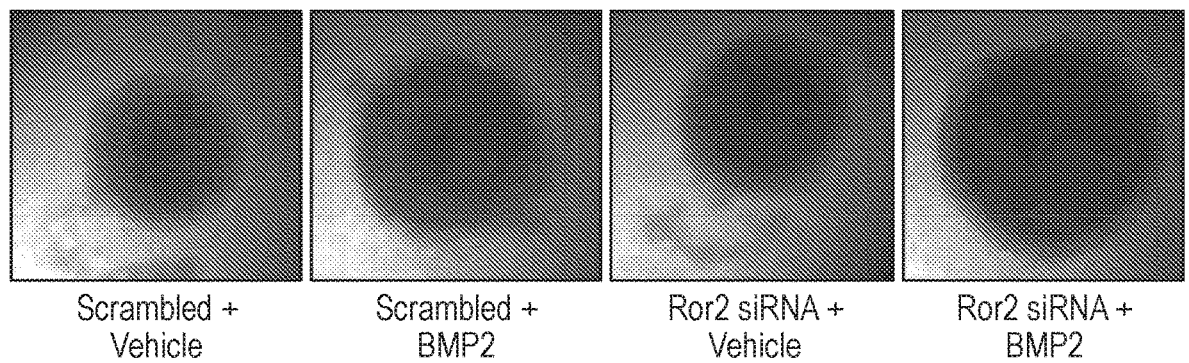
Figure 3E:
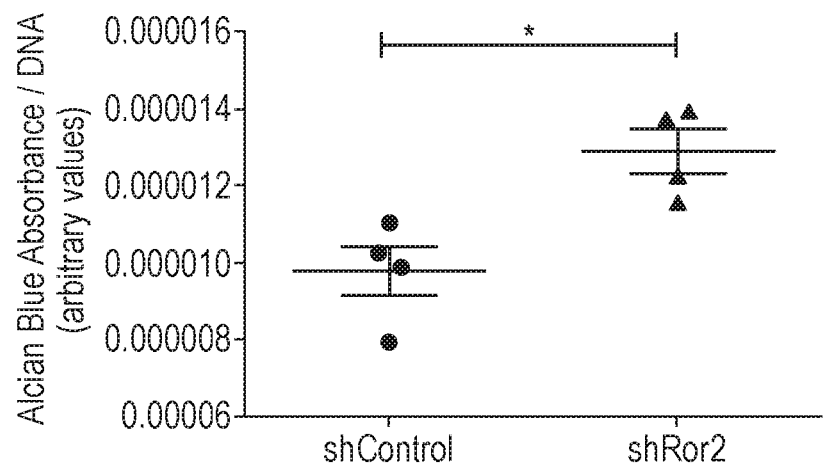
Figure 3E:
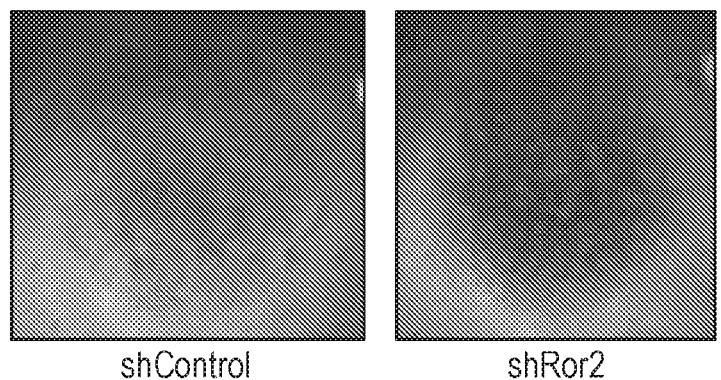
Figure 3F:
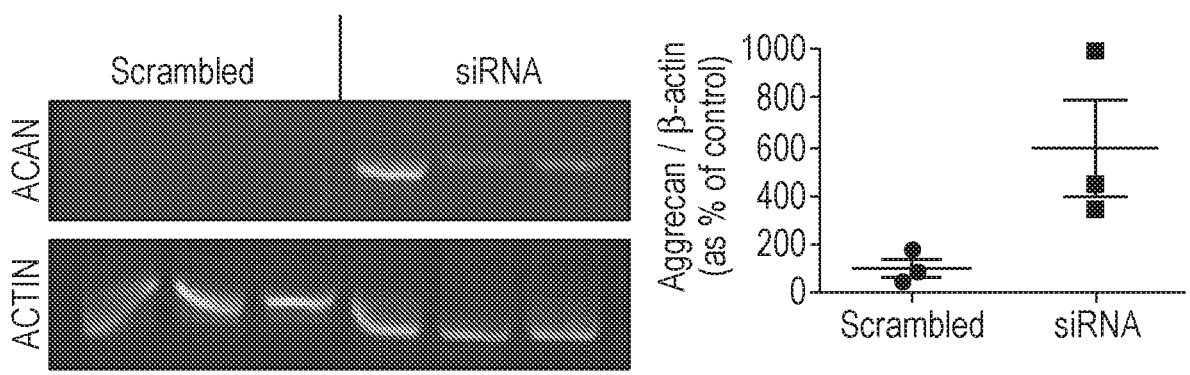
Figure 3G:
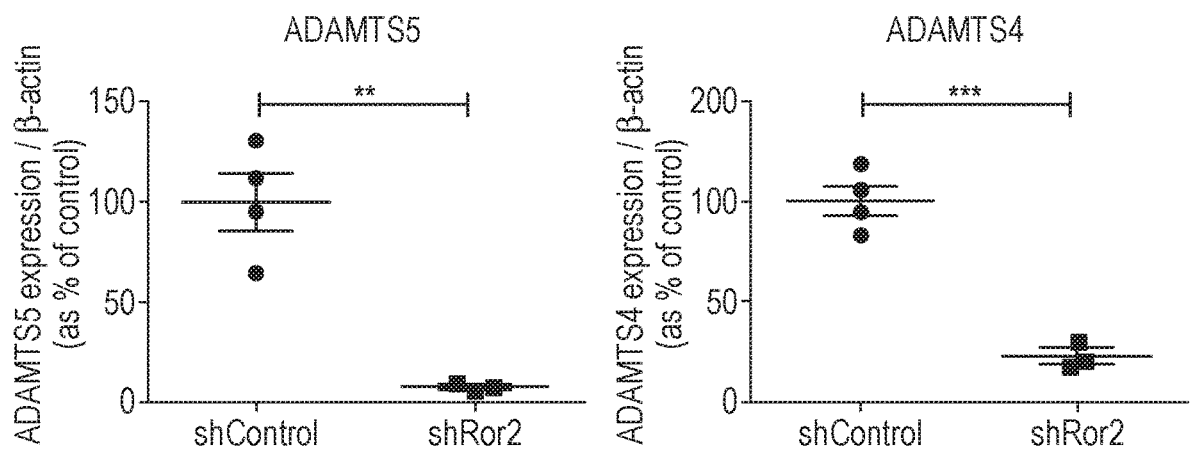
Figure 3H:
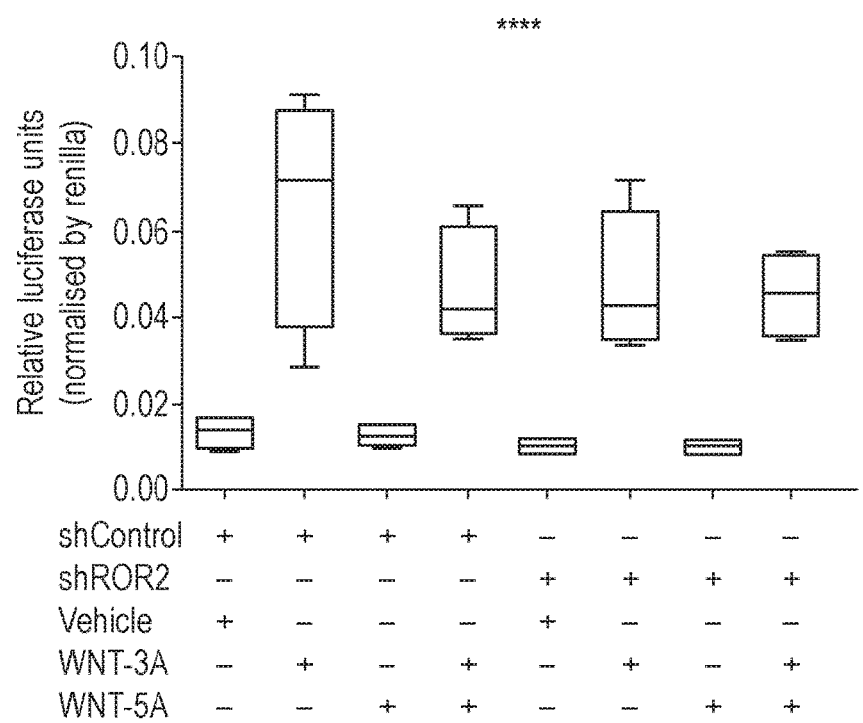

The data so far suggest that OA and inflammatory cytokines induce upregulation of ROR2 and that ROR2-dependent signalling suppresses chondrocyte differentiation. We therefore tested whether ROR2 loss of function resulted in cartilage anabolism. We designed siRNA that silenced ROR2 expression by approximately 73% at protein level in vitro (FIG. 3A). We also designed shRNA-lentivirus which downregulated Ror2 mRNA by 92% and protein by 56% (FIGS. 3B and C). The expression of Ror1 was not changed, confirming the specificity of RNA interference (FIG. 3B). As expected, the mesenchymal cell line MC3H10T1/2 differentiated towards chondrogenesis in response to BMP-2. Using either the siRNA or the shRNA-lentivirus, ROR2 silencing was sufficient to drive chondrocytic differentiation of MC3H10T1/2 cells, even without BMP-2, as assessed by Alcian blue staining (FIGS. 3D and E) and ACAN mRNA expression (FIG. 3F). In addition, ROR2 silencing strongly inhibited the expression of the key cartilage degrading enzymes ADAMTS-4 and ADAMTS-5 (FIG. 3G). Interestingly, ROR2 silencing did not result in an increase of the activation of the luciferase reporter by WNT-3A (FIG. 3H).

Figure 4A:
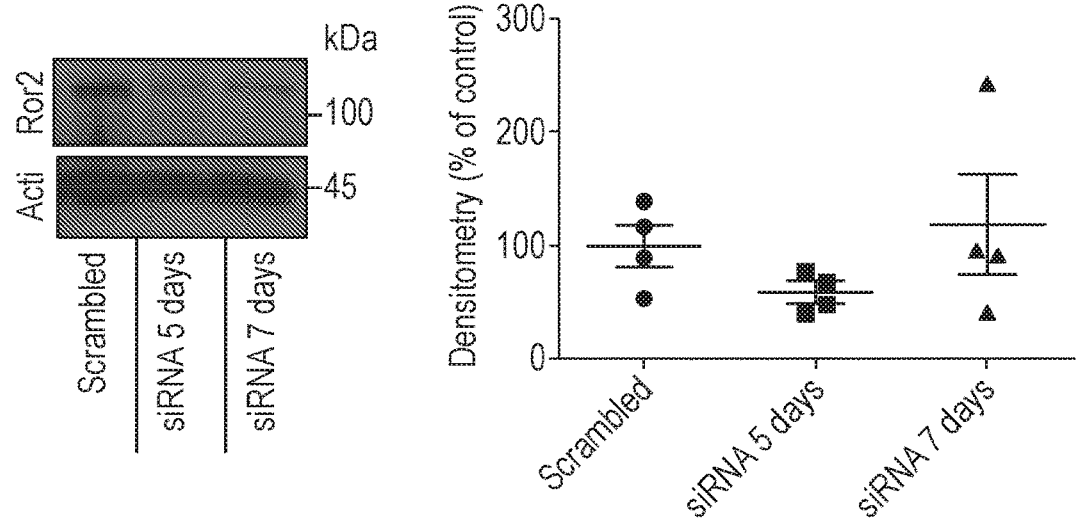
FIG. 4. ROR2 silencing in vivo resulted in improvement of symptoms and structural features of osteoarthritis. (A) Western blot showing that atelocollagen-ROR2-siRNA inhibits of ROR2 protein expression. (B) Immunofluorescence staining showing that atelocollagen-ROR2-siRNA silencing induced downregulation of ROR2 target protein CTGF. (C) Atelocollagen-ROR2-siRNA treatment of skeletally mature mice with surgically-induced menisco-ligament injury (MLI)—a model of osteoarthritis—to one hind limb resulted in significantly reduced pain on weight bearing as compared to control mice administered atelocollagen-scrambled-siRNA. 6 weeks post surgery, i.e. following 13 days of administration with atelocollagen-ROR2-siRNA, the treatment group had returned to 50% weight bearing on each hind limb, indicating absence of pain upon weight bearing. (D) siRNA silencing of ROR2 significantly reduced subchondral bone sclerosis as measured by bone volume/tissue volume ratio (BV/TV). (E) Histomorphometric analysis of Safranin-O staining intensity showing a significantly increased retention/reduction of degradation of glycosoaminoglycans (GAGs) in the treatment group. (F) Correlation between Safranin-O staining (i.e. presence of GAG) and percentage of body weight carried on the limb with osteoarthritis.
Figure 4B:
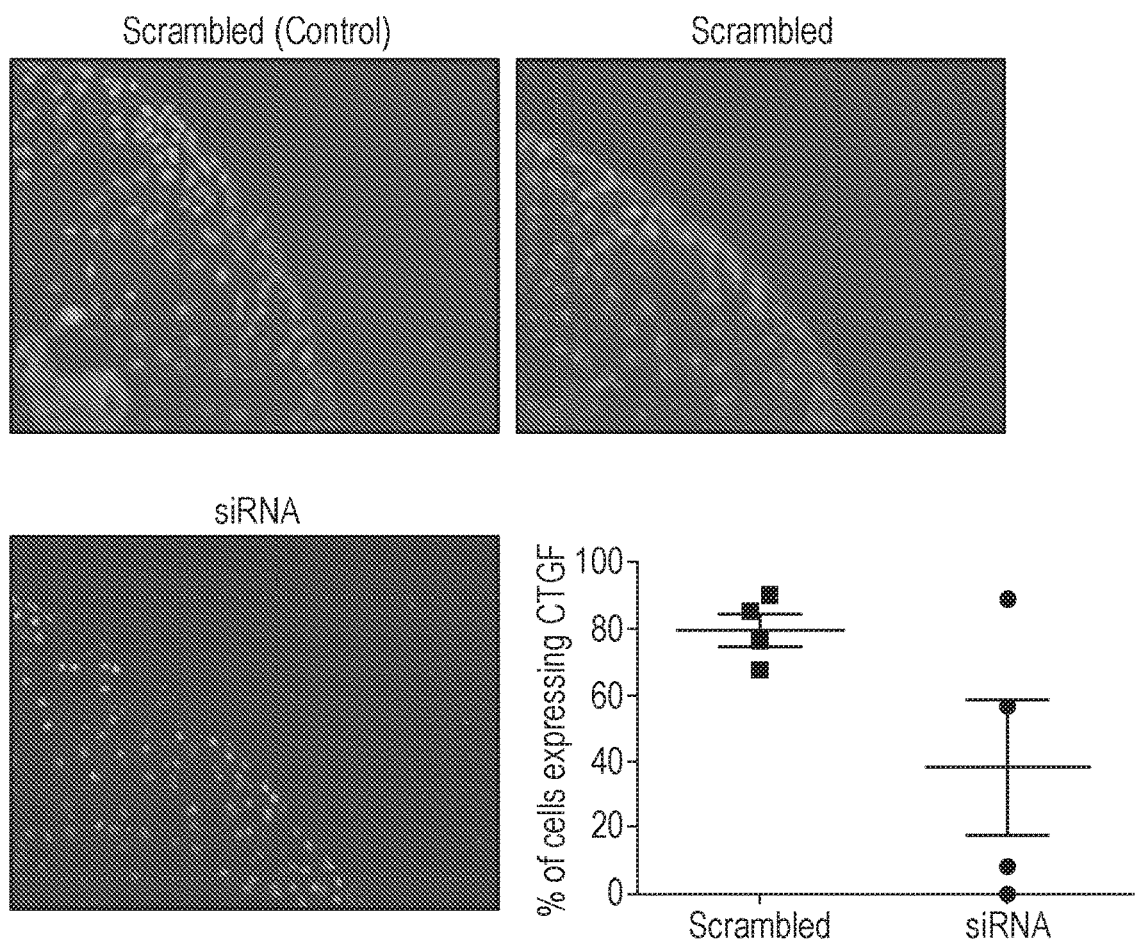

Example 5—ROR2 Silencing In Vivo Resulted in Improvement of Symptoms and Structural Features of Osteoarthritis The anabolic effect of ROR2 blockade and the suppression of key catabolic enzymes prompted us to test whether ROR2 loss of function may be beneficial in OA. In vivo, chondrocytes are difficult to target with traditional therapeutics and macromolecules because cartilage is avascular and chondrocytes are encased in a dense, strongly negatively charged extracellular matrix. To block ROR2 using a clinically relevant yet effective technology, we used siRNA coupled with Atelocollagen (Diarra et al., 2007; Distler et al., 2014). In a set of validation experiments, we established that the intra-articular injection of 7 μL of 20 μM ROR2 siRNA (or scrambled control) conjugated to 0.5% Atelocollagen achieved ~50% reduction of ROR2 protein expression for as long as 5 days (FIG. 4A). Importantly, this silencing efficiency was sufficient to downregulate the ROR2 target gene CTGF by ~60% (FIG. 4B).

Figure 4C:
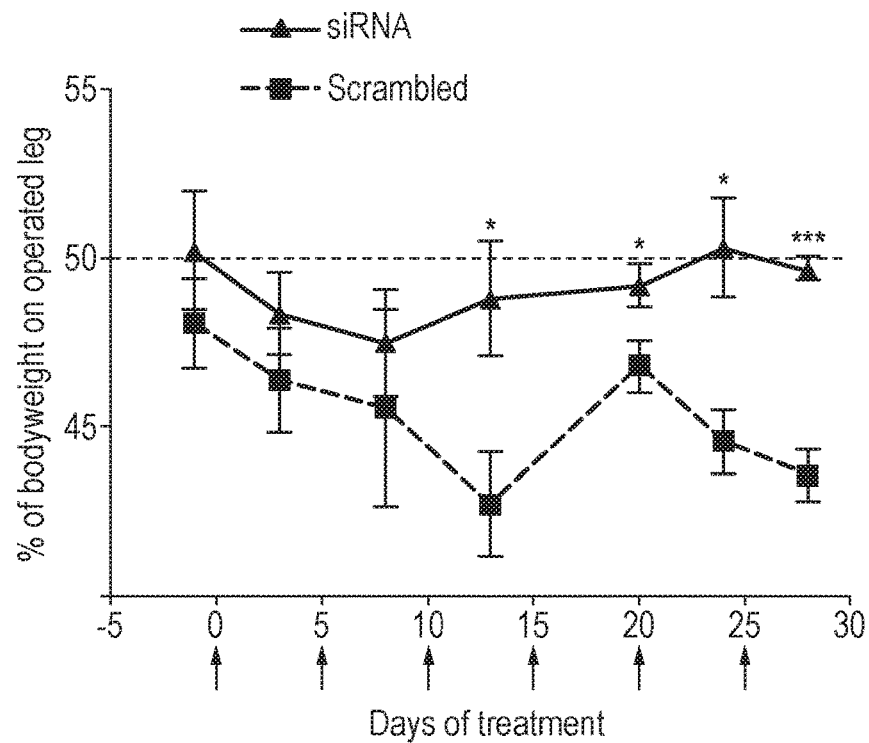

As a model of instability-induced osteoarthritis we subjected skeletally mature mice to surgical resection of the anterior horn of the medial meniscus and of the medial collateral ligament (also known as menisco-ligament injury; hereafter MLI) (Sampson et al., 2011b; Johnson et al., 2012; Hamada et al., 2014). The contralateral limb underwent sham surgery. Four weeks after surgery (when cartilage and bone lesions are already established; Sampson et al., 2011a), half of the mice received bilateral intra-articular injections of Atelocollagen-ROR2-siRNA (treatment group) and the other half atelocollagen-scrambled-siRNA (control group) every 5 days (N per group=6). By the sixth week following surgery, the mice in the control group had developed pain on weight bearing as assessed using the Linton incapacitance meter. After an initial trend towards incapacitance, at six weeks the mice in the treatment group returned to 50% weight bearing on each hind limb, indicating absence of pain upon weight bearing (FIG. 4C—day 13 of treatment).

Figure 4D:
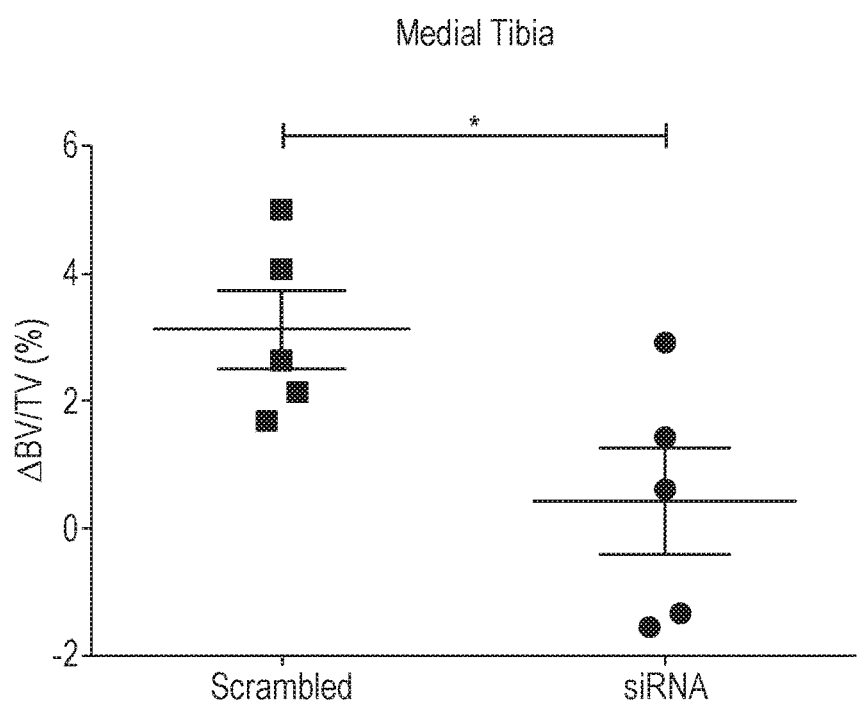
Figure 4E:
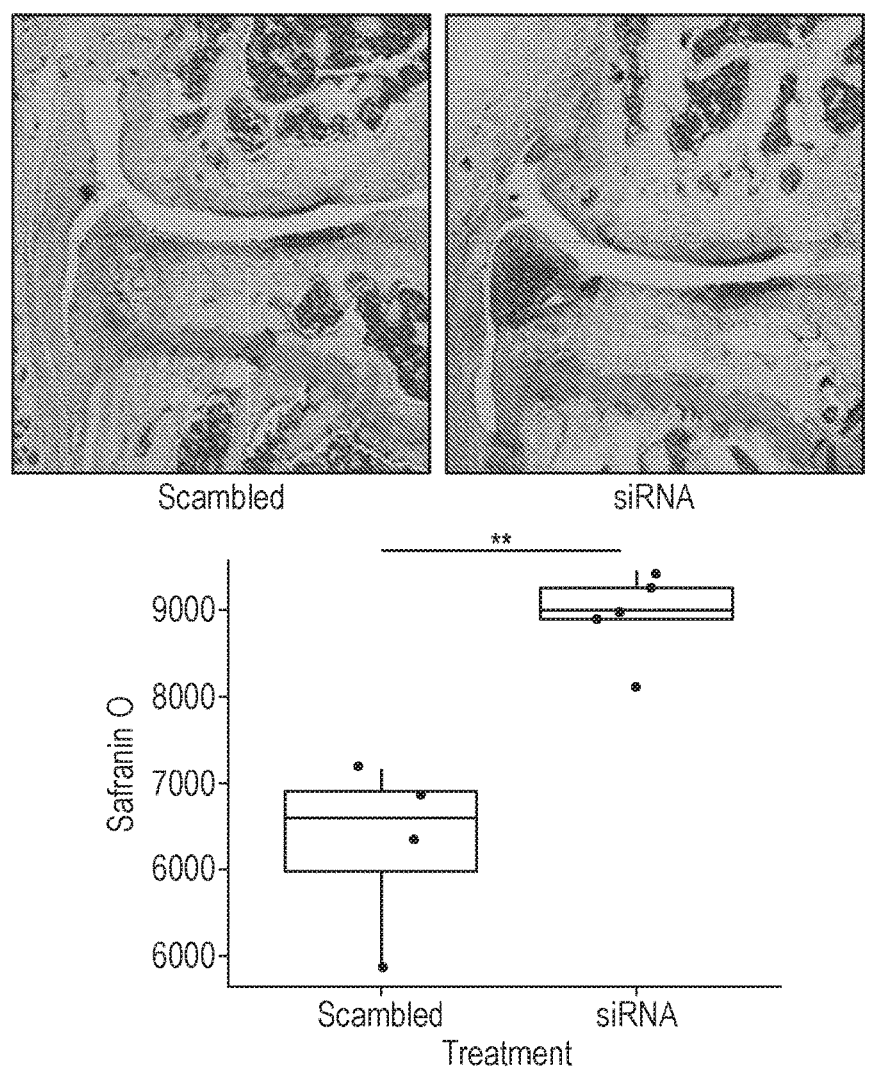
Figure 4F:
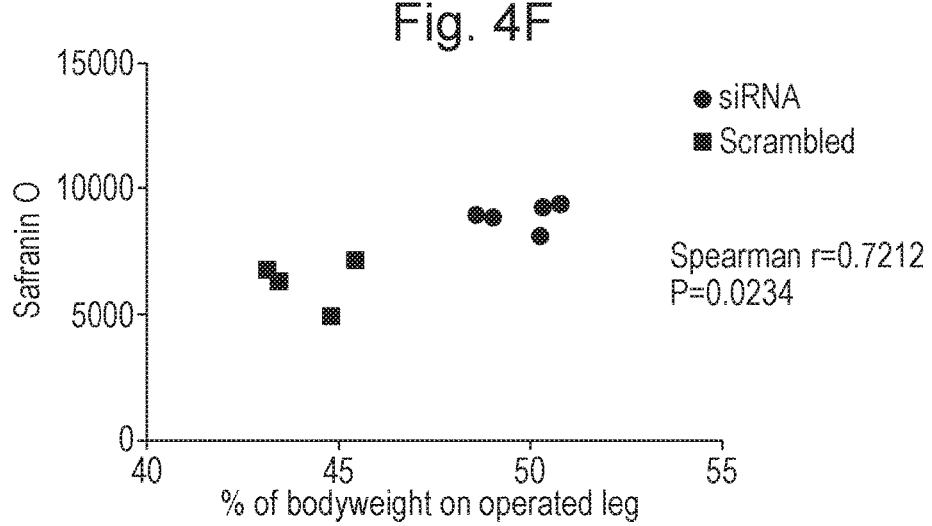

OA is associated with substantial sclerosis of the subchondral bone and the formation of new bone at the sides of the articular surface called osteophytes. ROR2 silencing was associated with normalization of the subchondral bone sclerosis as measured by bone volume/tissue volume ratio (BV/TV) (FIG. 4D). Histomorphometric analysis of Safranin-O staining intensity revealed a significantly increased retention/reduction of degradation of GAGs in the treatment group (FIG. 4E). The intensity of Safranin-O correlated strongly with incapacitance, demonstrating a link between structural and symptomatic improvements (FIG. 4F).

Figure 5:
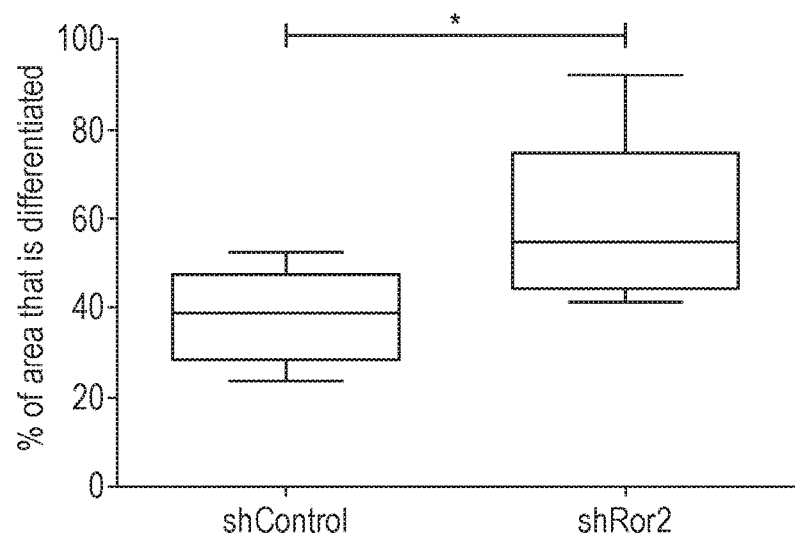
FIG. 5. ROR2 silencing supports formation of human cartilage organoids in vivo. shRNA-lentivirus silencing of ROR2 resulted in significantly increased GAG content in human cartilage organoids (generated by ectopically implanting human articular chondrocytes in nude mice).
Figure 5:
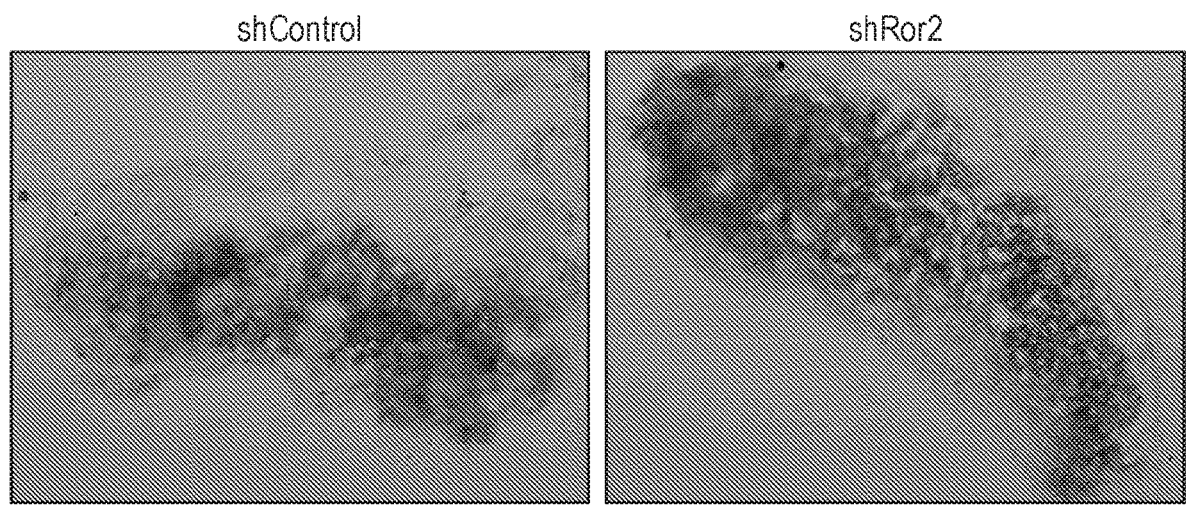

Example 6—ROR2 Silencing Supports Formation of Human Cartilage Organoids In Vivo One problem with translating data from mouse models to humans is the degree of conservation of molecular pathways across the species. To validate ROR2 as a therapeutic target in human cartilage we utilised an adoptive model in which human chondrocytes implanted ectopically in nude mice generate cartilage organoids that are phenotypically stable, resistant to vascularization and endochondral bone formation (Dell'Accio et al., 2001, 2003; Nalesso et al., 2011; Eldridge et al., 2015). ROR2 blockade was achieved by transducing chondrocytes with a lentivirus encoding either a ROR2-specific shRNA or a scrambled sequence as control. Human articular chondrocytes transduced with ROR2 shRNA had greater GAG content than controls (FIG. 5). This finding confirming that ROR2 blockade is sufficient to support cartilage differentiation in vivo in human chondrocytes.

All publications mentioned in the above specification are herein incorporated by reference. Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, cell biology, immunology or related fields are intended to be within the scope of the following claims.

SEQUENCE LISTING

```
<160> NUMBER OF SEQ ID NOS: 31

<210> SEQ ID NO 1
<211> LENGTH: 21
<212> TYPE: RNA
<213> ORGANISM: Artificial Sequence
<220> FEATURE:
<223> OTHER INFORMATION: Synthetic construct

<400> SEQUENCE: 1
aagucuacaa aggucaccug u                                              21

<210> SEQ ID NO 2
<211> LENGTH: 29
<212> TYPE: RNA
<213> ORGANISM: Artificial Sequence
<220> FEATURE:
<223> OTHER INFORMATION: Synthetic construct

<400> SEQUENCE: 2
aagucuacaa aggucaccug uccugucuc                                      29

<210> SEQ ID NO 3
<211> LENGTH: 21
<212> TYPE: RNA
<213> ORGANISM: Artificial Sequence
<220> FEATURE:
<223> OTHER INFORMATION: Synthetic construct

<400> SEQUENCE: 3
aaacagguga ccuuuguaga c                                              21

<210> SEQ ID NO 4
<211> LENGTH: 27
<212> TYPE: RNA
<213> ORGANISM: Artificial Sequence
```

<220> FEATURE:
<223> OTHER INFORMATION: Synthetic construct

<400> SEQUENCE: 4
aaacagguga ccuguagacc cugucuc                                            27

<210> SEQ ID NO 5
<211> LENGTH: 943
<212> TYPE: PRT
<213> ORGANISM: Homo sapiens

<400> SEQUENCE: 5

```
Met Ala Arg Gly Ser Ala Leu Pro Arg Pro Leu Leu Cys Ile Pro
1               5                   10                  15

Ala Val Trp Ala Ala Ala Leu Leu Leu Ser Val Ser Arg Thr Ser
                20                  25                  30

Gly Glu Val Glu Val Leu Asp Pro Asn Asp Pro Leu Gly Pro Leu Asp
                35                  40                  45

Gly Gln Asp Gly Pro Ile Pro Thr Leu Lys Gly Tyr Phe Leu Asn Phe
50                      55                  60

Leu Glu Pro Val Asn Asn Ile Thr Ile Val Gln Gly Gln Thr Ala Ile
65                  70                  75                  80

Leu His Cys Lys Val Ala Gly Asn Pro Pro Pro Asn Val Arg Trp Leu
                85                  90                  95

Lys Asn Asp Ala Pro Val Val Gln Glu Pro Arg Arg Ile Ile Ile Arg
                100                 105                 110

Lys Thr Glu Tyr Gly Ser Arg Leu Arg Ile Gln Asp Leu Asp Thr Thr
                115                 120                 125

Asp Thr Gly Tyr Tyr Gln Cys Val Ala Thr Asn Gly Met Lys Thr Ile
130                     135                 140

Thr Ala Thr Gly Val Leu Phe Val Arg Leu Gly Pro Thr His Ser Pro
145                 150                 155                 160

Asn His Asn Phe Gln Asp Asp Tyr His Glu Asp Gly Phe Cys Gln Pro
                165                 170                 175

Tyr Arg Gly Ile Ala Cys Ala Arg Phe Ile Gly Asn Arg Thr Ile Tyr
                180                 185                 190

Val Asp Ser Leu Gln Met Gln Gly Glu Ile Glu Asn Arg Ile Thr Ala
                195                 200                 205

Ala Phe Thr Met Ile Gly Thr Ser Thr His Leu Ser Asp Gln Cys Ser
                210                 215                 220

Gln Phe Ala Ile Pro Ser Phe Cys His Phe Val Phe Pro Leu Cys Asp
225                 230                 235                 240

Ala Arg Ser Arg Ala Pro Lys Pro Arg Glu Leu Cys Arg Asp Glu Cys
                245                 250                 255

Glu Val Leu Glu Ser Asp Leu Cys Arg Gln Glu Tyr Thr Ile Ala Arg
                260                 265                 270

Ser Asn Pro Leu Ile Leu Met Arg Leu Gln Leu Pro Lys Cys Glu Ala
                275                 280                 285

Leu Pro Met Pro Glu Ser Pro Asp Ala Ala Asn Cys Met Arg Ile Gly
                290                 295                 300

Ile Pro Ala Glu Arg Leu Gly Arg Tyr His Gln Cys Tyr Asn Gly Ser
305                 310                 315                 320

Gly Met Asp Tyr Arg Gly Thr Ala Ser Thr Thr Lys Ser Gly His Gln
                325                 330                 335

Cys Gln Pro Trp Ala Leu Gln His Pro His Ser His His Leu Ser Ser
```

```
              340                 345                 350
Thr Asp Phe Pro Glu Leu Gly Gly His Ala Tyr Cys Arg Asn Pro
            355                 360                 365
Gly Gly Gln Met Glu Gly Pro Trp Cys Phe Thr Gln Asn Lys Asn Val
        370                 375                 380
Arg Met Glu Leu Cys Asp Val Pro Ser Cys Ser Pro Arg Asp Ser Ser
385                 390                 395                 400
Lys Met Gly Ile Leu Tyr Ile Leu Val Pro Ser Ile Ala Ile Pro Leu
                405                 410                 415
Val Ile Ala Cys Leu Phe Phe Leu Val Cys Met Cys Arg Asn Lys Gln
            420                 425                 430
Lys Ala Ser Ala Ser Thr Pro Gln Arg Gln Leu Met Ala Ser Pro
        435                 440                 445
Ser Gln Asp Met Glu Met Pro Leu Ile Asn Gln His Lys Gln Ala Lys
        450                 455                 460
Leu Lys Glu Ile Ser Leu Ser Ala Val Arg Phe Met Glu Leu Gly
465                 470                 475                 480
Glu Asp Arg Phe Gly Lys Val Tyr Lys Gly His Leu Phe Gly Pro Ala
            485                 490                 495
Pro Gly Glu Gln Thr Gln Ala Val Ala Ile Lys Thr Leu Lys Asp Lys
            500                 505                 510
Ala Glu Gly Pro Leu Arg Glu Glu Phe Arg His Glu Ala Met Leu Arg
        515                 520                 525
Ala Arg Leu Gln His Pro Asn Val Val Cys Leu Leu Gly Val Val Thr
        530                 535                 540
Lys Asp Gln Pro Leu Ser Met Ile Phe Ser Tyr Cys Ser His Gly Asp
545                 550                 555                 560
Leu His Glu Phe Leu Val Met Arg Ser Pro His Ser Asp Val Gly Ser
                565                 570                 575
Thr Asp Asp Asp Arg Thr Val Lys Ser Ala Leu Glu Pro Pro Asp Phe
            580                 585                 590
Val His Leu Val Ala Gln Ile Ala Ala Gly Met Glu Tyr Leu Ser Ser
        595                 600                 605
His His Val His Lys Asp Leu Ala Thr Arg Asn Val Leu Val Tyr
        610                 615                 620
Asp Lys Leu Asn Val Lys Ile Ser Asp Leu Gly Leu Phe Arg Glu Val
625                 630                 635                 640
Tyr Ala Ala Asp Tyr Tyr Lys Leu Leu Gly Asn Ser Leu Leu Pro Ile
            645                 650                 655
Arg Trp Met Ala Pro Glu Ala Ile Met Tyr Gly Lys Phe Ser Ile Asp
            660                 665                 670
Ser Asp Ile Trp Ser Tyr Gly Val Val Leu Trp Glu Val Phe Ser Tyr
        675                 680                 685
Gly Leu Gln Pro Tyr Cys Gly Tyr Ser Asn Gln Asp Val Val Glu Met
        690                 695                 700
Ile Arg Asn Arg Gln Val Leu Pro Cys Pro Asp Asp Cys Pro Ala Trp
705                 710                 715                 720
Val Tyr Ala Leu Met Ile Glu Cys Trp Asn Glu Phe Pro Ser Arg Arg
            725                 730                 735
Pro Arg Phe Lys Asp Ile His Ser Arg Leu Arg Ala Trp Gly Asn Leu
            740                 745                 750
Ser Asn Tyr Asn Ser Ser Ala Gln Thr Ser Gly Ala Ser Asn Thr Thr
        755                 760                 765
```

```
Gln Thr Ser Ser Leu Ser Thr Ser Pro Val Ser Asn Val Ser Asn Ala
        770                 775                 780
Arg Tyr Val Gly Pro Lys Gln Lys Ala Pro Phe Pro Gln Pro Gln
785                 790                 795                 800
Phe Ile Pro Met Lys Gly Gln Ile Arg Pro Met Val Pro Pro Gln
                805                 810                 815
Leu Tyr Ile Pro Val Asn Gly Tyr Gln Pro Val Pro Ala Tyr Gly Ala
                820                 825                 830
Tyr Leu Pro Asn Phe Tyr Pro Val Gln Ile Pro Met Gln Met Ala Pro
        835                 840                 845
Gln Gln Val Pro Pro Gln Met Val Pro Lys Pro Ser Ser His His Ser
    850                 855                 860
Gly Ser Gly Ser Thr Ser Thr Gly Tyr Val Thr Thr Ala Pro Ser Asn
865                 870                 875                 880
Thr Ser Met Ala Asp Arg Ala Ala Leu Leu Ser Glu Gly Ala Asp Asp
                885                 890                 895
Thr Gln Asn Ala Pro Glu Asp Gly Ala Gln Ser Thr Val Gln Glu Ala
                900                 905                 910
Glu Glu Glu Glu Glu Gly Ser Val Pro Glu Thr Glu Leu Leu Gly Asp
            915                 920                 925
Cys Asp Thr Leu Gln Val Asp Glu Ala Gln Val Gln Leu Glu Ala
        930                 935                 940

<210> SEQ ID NO 6
<211> LENGTH: 3310
<212> TYPE: DNA
<213> ORGANISM: Homo sapiens

<400> SEQUENCE: 6
ggacgcatcg tagaaagggg tggtggcgcc cgaccccgcg ccccggcccg aagctctgag      60
ggcttcccgg cccccactgc ctgcggcatg gccggggct cggcgctccc gcggcggccg     120
ctgctgtgca tcccggccgt ctgggcggcc gccgcgcttc tgctctcagt gtcccggact     180
tcaggtgaag tggaggttct ggatccgaac gacccctttag gacccctttga tgggcaggac     240 ggcccgattc caactctgaa aggttacttt ctgaatttc tggagccagt aaacaatatc     300
accattgtcc aaggccagac ggcaattctg cactgcaagg tggcaggaaa ccacccccct     360
aacgtgcggt ggctaaagaa tgatgccccg gtggtgcagg agccgcggcg gatcatcatc     420
cggaagacag aatatggttc acgactgcga atccaggacc tggacacgac agacactggc     480
tactaccagt gcgtggccac caacgggatg aagaccatta ccgccactgg cgtcctgttt     540
gtgcggctgg tccaacgca cagcccaaat cataactttc aggatgatta ccacgaggat     600
gggttctgcc agccttaccg ggaattgcc tgtgcacgct tcattggcaa ccggaccatt     660
tatgtggact cgcttcagat gcagggggag attgaaaacc gaatcacagc ggccttcacc     720
atgatcggca cgtctacgca cctgtcggac cagtgctcac agttcgccat ccatcctc      780 tgccacttcg tgtttcctct gtgcgacgcg cgctcccggg cacccaagcc gcgtgagctg     840
tgccgcgacg agtgcgaggt gctggagagc gacctgtgcc gccaggagta caccatcgcc     900
cgctccaacc cgctcatcct catgcggctt cagctgccca gtgtgaggc gctgccatg     960 cctgagagcc ccgacgctgc caactgcatg cgcattggca tcccagccga gaggctgggc    1020
cgctaccatc agtgctataa cggctcaggc atggattaca gaggaacggc aagcaccacc    1080
aagtcaggcc accagtgcca gccgtgggcc ctgcagcacc ccacagcca ccacctgtcc    1140
```

| | |
|---|---|
| agcacagact tccctgagct tggaggggggg cacgcctact gccggaaccc cggaggccag | 1200 |
| atggagggcc cctggtgctt tacgcagaat aaaaacgtac gcatggaact gtgtgacgta | 1260 |
| ccctcgtgta gtccccgaga cagcagcaag atggggattc tgtacatctt ggtccccagc | 1320 |
| atcgcaattc cactggtcat cgcttgcctt ttcttcttgg tttgcatgtg ccggaataag | 1380 |
| cagaaggcat ctgcgtccac accgcagcgg cgacagctga tggcctcgcc cagccaagac | 1440 |
| atggaaatgc ccctcattaa ccagcacaaa caggccaaac tcaaagagat cagcctgtct | 1500 |
| gcggtgaggt tcatggagga gctgggagag gaccggtttg ggaaagtcta caaggtcac | 1560 |
| ctgttcggcc ctgccccggg ggagcagacc caggctgtgg ccatcaaaac gctgaaggac | 1620 |
| aaagcggagg ggcccctgcg ggaggagttc cggcatgagg ctatgctgcg agcacggctg | 1680 |
| caacacccca cgtcgtctg cctgctgggc gtggtgacca aggaccagcc cctgagcatg | 1740 |
| atcttcagct actgttcgca cggcgacctc cacgaattcc tggtcatgcg ctcgccgcac | 1800 |
| tcggacgtgg gcagcaccga tgatgaccgc acggtgaagt ccgccctgga gcccccgac | 1860 |
| ttcgtgcacc ttgtggcaca gatcgcggcg gggatggagt acctatccag ccaccacgtg | 1920 |
| gttcacaagg acctggccac ccgcaatgtg ctagtgtacg acaagctgaa cgtgaagatc | 1980 |
| tcagacttgg gcctcttccg agaggtgtat gccgccgatt actacaagct gctggggaac | 2040 |
| tcgctgctgc ctatccgctg gatggcccca gaggccatca tgtacggcaa gttctccatc | 2100 |
| gactcagaca tctggtccta cggtgtggtc ctgtgggagg tcttcagcta cggcctgcag | 2160 |
| ccctactgcg ggtattccaa ccaggatgtg gtggagatga tccggaaccg gcaggtgctg | 2220 |
| ccttgccccg atgactgtcc cgcctgggtg tatgccctca tgatcgagtg ctggaacgag | 2280 |
| ttccccagcc ggcggccccg cttcaaggac atccacagcc ggctccgagc ctggggcaac | 2340 |
| cttttccaact acaacagctc ggcgcagacc tcggggggcca gcaacaccac gcagaccagc | 2400 |
| tccctgagca ccagcccagt gagcaatgtg agcaacgccc gctacgtggg gcccaagcag | 2460 |
| aaggccccgc ccttcccaca gccccagttc atccccatga agggccagat cagacccatg | 2520 |
| gtgccccgc cgcagctcta catccccgtc aacggctacc agccggtgcc ggcctatggg | 2580 |
| gcctacctgc ccaacttcta cccggtgcag atcccaatgc agatggcccc gcagcaggtg | 2640 |
| cctcctcaga tggtccccaa gcccagctca caccacagtg gcagtggctc caccagcaca | 2700 |
| ggctacgtca ccacggcccc ctccaacaca tccatggcag acaggggcagc cctgctctca | 2760 |
| gagggcgctg atgacacaca gaacgcccca gaagatgggg cccagagcac cgtgcaggaa | 2820 |
| gcagaggagg aggaggaagg ctctgtccca gagactgagc tgctggggga ctgtgacact | 2880 |
| ctgcaggtgg acgaggccca agtccagctg gaagcttgag tggcaccagg gcccagggtt | 2940 |
| cggggataga agccccgccg agaccccaca gggacctcag tcacctttga gaagacacca | 3000 |
| tactcagcaa tcacaagagc ccgccggcca gtgggcttgt ttgcagactg ggtgaggtgg | 3060 |
| agccctgctc ctctctgtcc tctgacacag ctgcccgcc taggagcacc caagccaggc | 3120 |
| aggggggtctg gcagcacggc gtcctgggga gcaggacaca tggtcatccc cagggctgta | 3180 |
| tacattgatt ctggtggtag actggtagtg agcagcaaat gcctttcaag aaaataggtg | 3240 |
| gcagcttcac tccatgtcat atatggagtg aatatttcaa acgttggga ataagggcct | 3300 |
| gcaaaaggca | 3310 |

<210> SEQ ID NO 7
<211> LENGTH: 944
<212> TYPE: PRT

<213> ORGANISM: Mus musculus

<400> SEQUENCE: 7

Met Ala Arg Gly Trp Val Arg Pro Ser Arg Val Pro Leu Cys Ala Arg
1               5                   10                  15

Ala Val Trp Thr Ala Ala Ala Leu Leu Leu Trp Thr Pro Trp Thr Ala
            20                  25                  30

Gly Glu Val Glu Asp Ser Glu Ala Ile Asp Thr Leu Gly Gln Pro Asp
        35                  40                  45

Gly Pro Asp Ser Pro Leu Pro Thr Leu Lys Gly Tyr Phe Leu Asn Phe
    50                  55                  60

Leu Glu Pro Val Asn Asn Ile Thr Ile Val Gln Gly Gln Thr Ala Ile
65                  70                  75                  80

Leu His Cys Lys Val Ala Gly Asn Pro Pro Asn Val Arg Trp Leu
                85                  90                  95

Lys Asn Asp Ala Pro Val Val Gln Glu Pro Arg Arg Val Ile Ile Arg
                100                 105                 110

Lys Thr Glu Tyr Gly Ser Arg Leu Arg Ile Gln Asp Leu Asp Thr Thr
            115                 120                 125

Asp Thr Gly Tyr Tyr Gln Cys Val Ala Thr Asn Gly Leu Lys Thr Ile
    130                 135                 140

Thr Ala Thr Gly Val Leu Tyr Val Arg Leu Gly Pro Thr His Ser Pro
145                 150                 155                 160

Asn His Asn Phe Gln Asp Asp Gln Glu Asp Gly Phe Cys Gln Pro
                165                 170                 175

Tyr Arg Gly Ile Ala Cys Ala Arg Phe Ile Gly Asn Arg Thr Ile Tyr
                180                 185                 190

Val Asp Ser Leu Gln Met Gln Gly Glu Ile Glu Asn Arg Ile Thr Ala
    195                 200                 205

Ala Phe Thr Met Ile Gly Thr Ser Thr Gln Leu Ser Asp Gln Cys Ser
    210                 215                 220

Gln Phe Ala Ile Pro Ser Phe Cys His Phe Val Phe Pro Leu Cys Asp
225                 230                 235                 240

Ala Arg Ser Arg Ala Pro Lys Pro Arg Glu Leu Cys Arg Asp Glu Cys
                245                 250                 255

Glu Val Leu Glu Asn Asp Leu Cys Arg Gln Glu Tyr Thr Ile Ala Arg
            260                 265                 270

Ser Asn Pro Leu Ile Leu Met Arg Leu Gln Leu Pro Lys Cys Glu Ala
        275                 280                 285

Leu Pro Met Pro Glu Ser Pro Asp Ala Ala Asn Cys Met Arg Ile Gly
    290                 295                 300

Ile Pro Ala Glu Arg Leu Gly Arg Tyr His Gln Cys Tyr Asn Gly Ser
305                 310                 315                 320

Gly Ala Asp Tyr Arg Gly Met Ala Ser Thr Thr Lys Ser Gly His Gln
                325                 330                 335

Cys Gln Pro Trp Ala Leu Gln His Pro His Ser His Arg Leu Ser Ser
            340                 345                 350

Thr Glu Phe Pro Glu Leu Gly Gly Gly His Ala Tyr Cys Arg Asn Pro
        355                 360                 365

Gly Gly Gln Val Glu Gly Pro Trp Cys Phe Thr Gln Asn Lys Asn Val
    370                 375                 380

Arg Val Glu Leu Cys Asp Val Pro Pro Cys Ser Pro Arg Asp Gly Ser
385                 390                 395                 400

```
Lys Met Gly Ile Leu Tyr Ile Leu Val Pro Ser Ala Ile Pro Leu
                405                 410                 415
Val Ile Ala Cys Leu Phe Phe Leu Val Cys Met Cys Arg Asn Lys Gln
        420                 425                 430
Lys Ala Ser Ala Ser Thr Pro Gln Arg Arg Gln Leu Met Ala Ser Pro
            435                 440                 445
Ser Gln Asp Met Glu Met Pro Leu Ile Ser Gln His Lys Gln Ala Lys
    450                 455                 460
Leu Lys Glu Ile Ser Leu Ser Thr Val Arg Phe Met Glu Glu Leu Gly
465                 470                 475                 480
Glu Asp Arg Phe Gly Lys Val Tyr Lys Gly His Leu Phe Gly Pro Ala
                485                 490                 495
Pro Gly Glu Pro Thr Gln Ala Val Ala Ile Lys Thr Leu Lys Asp Lys
            500                 505                 510
Ala Glu Gly Pro Leu Arg Glu Glu Phe Arg Gln Glu Ala Met Leu Arg
        515                 520                 525
Ala Arg Leu Gln His Pro Asn Ile Val Cys Leu Leu Gly Val Val Thr
    530                 535                 540
Lys Asp Gln Pro Leu Ser Met Ile Phe Ser Tyr Cys Ser His Gly Asp
545                 550                 555                 560
Leu His Glu Phe Leu Val Met Arg Ser Pro His Ser Asp Val Gly Ser
                565                 570                 575
Thr Asp Asp Asp Arg Thr Val Lys Ser Ala Leu Glu Pro Pro Asp Phe
            580                 585                 590
Val His Val Val Ala Gln Ile Ala Ala Gly Met Glu Phe Leu Ser Ser
        595                 600                 605
His His Val Val His Lys Asp Leu Ala Thr Arg Asn Val Leu Val Tyr
    610                 615                 620
Asp Lys Leu Asn Val Arg Ile Ser Asp Leu Gly Leu Phe Arg Glu Val
625                 630                 635                 640
Tyr Ser Ala Asp Tyr Tyr Lys Leu Met Gly Asn Ser Leu Leu Pro Ile
                645                 650                 655
Arg Trp Met Ser Pro Glu Ala Val Met Tyr Gly Lys Phe Ser Ile Asp
            660                 665                 670
Ser Asp Ile Trp Ser Tyr Gly Val Val Leu Trp Glu Val Phe Ser Tyr
        675                 680                 685
Gly Leu Gln Pro Tyr Cys Gly Tyr Ser Asn Gln Asp Val Val Glu Met
    690                 695                 700
Ile Arg Ser Arg Gln Val Leu Pro Cys Pro Asp Asp Cys Pro Ala Trp
705                 710                 715                 720
Val Tyr Ala Leu Met Ile Glu Cys Trp Asn Glu Phe Pro Ser Arg Arg
                725                 730                 735
Pro Arg Phe Lys Asp Ile His Ser Arg Leu Arg Ser Trp Gly Asn Leu
            740                 745                 750
Ser Asn Tyr Asn Ser Ser Ala Gln Thr Ser Gly Ala Ser Asn Thr Thr
        755                 760                 765
Gln Thr Ser Ser Leu Ser Thr Ser Pro Val Ser Asn Val Ser Asn Ala
    770                 775                 780
Arg Tyr Met Ala Pro Lys Gln Lys Ala Gln Pro Phe Pro Gln Pro Gln
785                 790                 795                 800
Phe Ile Pro Met Lys Gly Gln Ile Arg Pro Leu Val Pro Pro Ala Gln
                805                 810                 815
Leu Tyr Ile Pro Val Asn Gly Tyr Gln Pro Val Pro Ala Tyr Gly Ala
```

```
                820                 825                 830
Tyr Leu Pro Asn Phe Tyr Pro Val Gln Ile Pro Met Gln Met Ala Pro
            835                 840                 845

Gln Gln Val Pro Pro Gln Met Val Pro Lys Pro Ser Ser His His Ser
    850                 855                 860

Gly Ser Gly Ser Thr Ser Thr Gly Tyr Val Thr Thr Ala Pro Ser Asn
865                 870                 875                 880

Thr Ser Val Ala Asp Arg Ala Ala Leu Leu Ser Glu Gly Thr Glu Asp
                885                 890                 895

Ala Gln Asn Ile Ala Glu Asp Val Ala Gln Ser Pro Val Gln Glu Ala
            900                 905                 910

Glu Glu Glu Glu Glu Gly Ser Val Pro Glu Thr Glu Leu Leu Gly Asp
        915                 920                 925

Asn Asp Thr Leu Gln Val Thr Glu Ala Ala His Val Gln Leu Glu Ala
    930                 935                 940

<210> SEQ ID NO 8
<211> LENGTH: 2835
<212> TYPE: DNA
<213> ORGANISM: Mus musculus

<400> SEQUENCE: 8
```

| | | | | | |
|---|---|---|---|---|---|
| atggctcggg | gctgggtgcg | gccgagccgt | gtgcctctgt | gcgcccgggc | cgtctggacg | 60 |
| gctgcggcgc | tcctgctctg | gacaccctgg | acggcaggtg | aagtggaaga | ttcggaggca | 120 |
| atcgacacct | tgggacaacc | tgatggaccg | gacagcccac | ttcccactct | gaaaggctac | 180 |
| tttctgaatt | ttctggagcc | agtcaacaat | atcaccattg | ttcagggcca | gacggcaatc | 240 |
| ctgcactgca | aggtggcggg | aaacccacct | cccaatgtgc | ggtggctgaa | gaatgatgcc | 300 |
| ccggttgtgc | aagagccacg | aagggtcgtc | atccggaaga | cagaatacgg | ctcccggctg | 360 |
| cggatccaag | acctggacac | aacagacaca | ggctactacc | agtgtgtggc | taccaacggg | 420 |
| ctgaagacca | tcactgccac | tggggttcta | tatgtgcggc | tcggtccgac | gcacagcccg | 480 |
| aaccacaatt | tccaggatga | cgatcaggaa | gatggcttct | gccagccgta | ccgagggatc | 540 |
| gcttgtgcgc | gcttcattgg | gaaccggact | atttatgtgg | actccctcca | gatgcagggg | 600 |
| gagattgaaa | accgaatcac | agctgccttc | accatgatcg | gcacctccac | gcaactgtca | 660 |
| gaccagtgtt | cacagtttgc | catcccatcc | ttctgccact | tcgtcttccc | tctgtgcgac | 720 |
| gcatgctccc | gggcgcccaa | gcctcgcgaa | ctgtgccggg | atgaatgtga | ggtgctggag | 780 |
| aacgacctgt | gccgccagga | gtacaccatc | gcccgctcca | acccgctcat | cctcatgcgg | 840 |
| ctccagctgc | ccaagtgcga | agcgctgccc | atgcccgaga | gcccggatgc | tgcgaactgc | 900 |
| atgcgcatcg | ggatccccgc | ggagaggctg | ggtcgctacc | accagtgcta | caacggctcc | 960 |
| ggcgccgatt | acagggggat | ggccagtacc | accaagtcag | gccaccagtg | tcagccttgg | 1020 |
| gctctgcagc | accccacag | ccatcgccta | tccagcacgg | aattccctga | ctgggaggga | 1080 |
| ggccatgcct | actgccggaa | ccccggggggc | cagatggaag | gcccgtggtg | ctttacgcag | 1140 |
| aataaaaacg | tacgcgtgga | actgtgtgac | gtaccccgt | gtagtccccg | atatggcagc | 1200 |
| aagatgggga | ttctgtacat | cctggtcccc | agcattgcta | tccccctggt | catcgcttgc | 1260 |
| ctgttcttcc | tcgtctgcat | gtgccgcaac | aaacagaagg | cttcggcctc | caccccacag | 1320 |
| cgccggcagc | tgatggccctc | tcccagccag | gacatggaga | tgccactcat | cagccagcac | 1380 |
| aaacaggcca | aactcaaaga | gatcagcttg | tccacagtga | ggttcatgga | ggagctcggg | 1440 |

```
gaggaccggt tggcaaggt ctacaaaggc cacctgttcg ggcctgcccc aggagaacca    1500
acccaggccg tggccatcaa gacgctgaaa gacaaggctg aggggcccct gcgggaggag    1560
ttccggcaag aggcgatgct ccgggcccga ctgcagcacc ccaacatcgt ctgtctccta    1620
ggcgtcgtga ccaaggacca acccttgagc atgatcttca gctactgttc catggcgac    1680 cttcatgaat tcctggtcat gcgctcgccg cactccgatg tgggcagcac cgatgacgac    1740
cgcacagtga agtcagccct ggagcccccg gacttcgtgc acgtggtggc gcagatcgct    1800
gcggggatgg agttcctgtc cagccaccac gtgtgccata aggacctggc cacacgcaat    1860
gtgctggtgt acgacaagct gaacgtgagg atctcagact gggcctcttc cgtgaggta    1920 tactccgcag attactacaa actcatgggc aattcactgc tgcccatccg ctggatgtcc    1980
cccgaggccg tcatgtatgg aaagttctcc atcgactctg acatctggtc ctacggtgtg    2040
gtcctctggg aggtctttag ctacggcctg cagcccact gtgggtactc caaccaggac    2100
gtggtggaga tgatccggag ccggcaggtg ctgcccctgcc cggatgactg ccccgcctgg    2160
gtctatgccc tcatgattga atgctggaat gagttcccaa gccggaggcc ccgctttaag    2220
gacatccaca gccggctccg gtcctggggc aacctatcca actataatag ttccgcgcag    2280
acctcaggag ccagcaacac cacacagacc agctccctga gcaccagccc cgtaagcaat    2340
gtgagcaatg cccgctatat ggcccccaag cagaaggccc agcccttccc acagcctcag    2400
ttcatcccca tgaagggtca gatcagaccc ttggtgcccc ccgcacagct gtacatcccg    2460
gtgaacggct atcagccggt accggcatac gggccctacc tgcccaactt ctacccagtc    2520
cagatcccca tgcagatggc cccacagcag gtgcccctc agatggtccc caagccgagc    2580
tcacaccaca gtggcagcgg ctccaccagc actggctacg tcaccacggc gccctccaat    2640
acatctgtgg cggacagggc ggccctactc tctgagggca ccgaggatgt acagaacatc    2700
gcggaagacg tggcccagag ccctgtgcag gaagcagagg aggaggagga ggggtctgtc    2760
cctgagactg aactcctggg agacaatgac acgctccagg tgaccgaggc ggctcatgtc    2820
cagcttgaag cctga                                                    2835
```

<210> SEQ ID NO 9  
<211> LENGTH: 25  
<212> TYPE: PRT  
<213> ORGANISM: Artificial Sequence  
<220> FEATURE:  
<223> OTHER INFORMATION: Synthetic construct

<400> SEQUENCE: 9

Ser Ser Ser Thr Thr Thr Thr Thr Thr Thr Thr Leu Leu Leu Leu Leu
1               5                   10                  15

Leu Leu Leu Leu Leu Leu Leu Leu Leu
            20                  25

<210> SEQ ID NO 10  
<211> LENGTH: 406  
<212> TYPE: PRT  
<213> ORGANISM: Homo sapiens

<400> SEQUENCE: 10

Met Ala Arg Gly Ser Ala Leu Pro Arg Arg Pro Leu Leu Cys Ile Pro
1               5                   10                  15

Ala Val Trp Ala Ala Ala Ala Leu Leu Leu Ser Val Ser Arg Thr Ser
            20                  25                  30

Gly Glu Val Glu Val Leu Asp Pro Asn Asp Pro Leu Gly Pro Leu Asp

Gly Gln Asp Gly Pro Ile Pro Thr Leu Lys Gly Tyr Phe Leu Asn Phe
    50                  55                  60

Leu Glu Pro Val Asn Asn Ile Thr Ile Val Gln Gly Gln Thr Ala Ile
 65                  70                  75                  80

Leu His Cys Lys Val Ala Gly Asn Pro Pro Asn Val Arg Trp Leu
                 85                  90                  95

Lys Asn Asp Ala Pro Val Val Gln Glu Pro Arg Arg Ile Ile Ile Arg
            100                 105                 110

Lys Thr Glu Tyr Gly Ser Arg Leu Arg Ile Gln Asp Leu Asp Thr Thr
            115                 120                 125

Asp Thr Gly Tyr Tyr Gln Cys Val Ala Thr Asn Gly Met Lys Thr Ile
130                 135                 140

Thr Ala Thr Gly Val Leu Phe Val Arg Leu Gly Pro Thr His Ser Pro
145                 150                 155                 160

Asn His Asn Phe Gln Asp Asp Tyr His Glu Asp Gly Phe Cys Gln Pro
                165                 170                 175

Tyr Arg Gly Ile Ala Cys Ala Arg Phe Ile Gly Asn Arg Thr Ile Tyr
            180                 185                 190

Val Asp Ser Leu Gln Met Gln Gly Glu Ile Glu Asn Arg Ile Thr Ala
            195                 200                 205

Ala Phe Thr Met Ile Gly Thr Ser Thr His Leu Ser Asp Gln Cys Ser
210                 215                 220

Gln Phe Ala Ile Pro Ser Phe Cys His Phe Val Phe Pro Leu Cys Asp
225                 230                 235                 240

Ala Arg Ser Arg Ala Pro Lys Pro Arg Glu Leu Cys Arg Asp Glu Cys
                245                 250                 255

Glu Val Leu Glu Ser Asp Leu Cys Arg Gln Glu Tyr Thr Ile Ala Arg
            260                 265                 270

Ser Asn Pro Leu Ile Leu Met Arg Leu Gln Leu Pro Lys Cys Glu Ala
            275                 280                 285

Leu Pro Met Pro Glu Ser Pro Asp Ala Ala Asn Cys Met Arg Ile Gly
290                 295                 300

Ile Pro Ala Glu Arg Leu Gly Arg Tyr His Gln Cys Tyr Asn Gly Ser
305                 310                 315                 320

Gly Met Asp Tyr Arg Gly Thr Ala Ser Thr Thr Lys Ser Gly His Gln
                325                 330                 335

Cys Gln Pro Trp Ala Leu Gln His Pro His Ser His His Leu Ser Ser
            340                 345                 350

Thr Asp Phe Pro Glu Leu Gly Gly Gly His Ala Tyr Cys Arg Asn Pro
            355                 360                 365

Gly Gly Gln Met Glu Gly Pro Trp Cys Phe Thr Gln Asn Lys Asn Val
370                 375                 380

Arg Met Glu Leu Cys Asp Val Pro Ser Cys Ser Pro Arg Asp Ser Ser
385                 390                 395                 400

Lys Met Gly Ile Leu Tyr
                405

<210> SEQ ID NO 11
<211> LENGTH: 1218
<212> TYPE: DNA
<213> ORGANISM: Homo sapiens

<400> SEQUENCE: 11

| | |
|---|---|
| atggcccggg gctcggcgct cccgcggcgg ccgctgctgt gcatcccggc cgtctgggcg | 60 |
| gccgccgcgc ttctgctctc agtgtcccgg acttcaggtg aagtggaggt tctggatccg | 120 |
| aacgaccctt taggaccct tgatgggcag gacggcccga ttccaactct gaaaggttac | 180 |
| tttctgaatt ttctggagcc agtaaacaat atcaccattg tccaaggcca gacggcaatt | 240 |
| ctgcactgca aggtggcagg aaacccaccc cctaacgtgc ggtggctaaa gaatgatgcc | 300 |
| ccggtggtgc aggagccgcg gcggatcatc atccggaaga cagaatatgg ttcacgactg | 360 |
| cgaatccagg acctggacac gacagacact ggctactacc agtgcgtggc caccaacggg | 420 |
| atgaagacca ttaccgccac tggcgtcctg tttgtgcggc tgggtccaac gcacagccca | 480 |
| aatcataact ttcaggatga ttaccacgag gatgggttct gccagcctta ccggggaatt | 540 |
| gcctgtgcac gcttcattgg caaccggacc atttatgtgg actcgcttca gatgcagggg | 600 |
| gagattgaaa accgaatcac agcggccttc accatgatcg gcacgtctac gcacctgtcg | 660 |
| gaccagtgct cacagttcgc catcccatcc ttctgccact cgtgtttcc tctgtgcgac | 720 |
| gcgcgctccc gggcacccaa gccgcgtgag ctgtgccgcg acgagtgcga ggtgctggag | 780 |
| agcgacctgt gccgccagga gtacaccatc gcccgctcca accgctcat cctcatgcgg | 840 |
| cttcagctgc ccaagtgtga ggcgctgccc atgcctgaga gccccgacgc tgccaactgc | 900 |
| atgcgcattg gcatcccagc cgagaggctg ggccgctacc atcagtgcta taacggctca | 960 |
| ggcatggatt acagaggaac ggcaagcacc accaagtcag gccaccagtg ccagccgtgg | 1020 |
| gccctgcagc accccacag ccaccacctg tccagcacag acttccctga gcttggaggg | 1080 |
| gggcacgcct actgccggaa ccccggaggc cagatggagg gcccctggtg ctttacgcag | 1140 |
| aataaaaacg tacgcatgga actgtgtgac gtaccctcgt gtagtccccg agacagcagc | 1200 |
| aagatgggga ttctgtac | 1218 |

<210> SEQ ID NO 12
<211> LENGTH: 126
<212> TYPE: PRT
<213> ORGANISM: Homo sapiens

<400> SEQUENCE: 12

```
Cys Gln Pro Tyr Arg Gly Ile Ala Cys Ala Arg Phe Ile Gly Asn Arg
1               5                   10                  15

Thr Ile Tyr Val Asp Ser Leu Gln Met Gln Gly Glu Ile Glu Asn Arg
            20                  25                  30

Ile Thr Ala Ala Phe Thr Met Ile Gly Thr Ser Thr His Leu Ser Asp
        35                  40                  45

Gln Cys Ser Gln Phe Ala Ile Pro Ser Phe Cys His Phe Val Phe Pro
    50                  55                  60

Leu Cys Asp Ala Arg Ser Arg Ala Pro Lys Pro Arg Glu Leu Cys Arg
65                  70                  75                  80

Asp Glu Cys Glu Val Leu Glu Ser Asp Leu Cys Arg Gln Glu Tyr Thr
                85                  90                  95

Ile Ala Arg Ser Asn Pro Leu Ile Leu Met Arg Leu Gln Leu Pro Lys
            100                 105                 110

Cys Glu Ala Leu Pro Met Pro Glu Ser Pro Asp Ala Ala Asn
        115                 120                 125
```

<210> SEQ ID NO 13
<211> LENGTH: 379
<212> TYPE: DNA
<213> ORGANISM: Homo sapiens

<400> SEQUENCE: 13

```
ctgccagcct taccggggaa ttgcctgtgc acgcttcatt ggcaaccgga ccatttatgt      60
ggactcgctt cagatgcagg gggagattga aaaccgaatc acagcggcct tcaccatgat     120
cggcacgtct acgcacctgt cggaccagtg ctcacagttc gccatcccat ccttctgcca     180
cttcgtgttt cctctgtgcg acgcgcgctc ccgggcaccc aagccgcgtg agctgtgccg     240
cgacgagtgc gaggtgctgg agagcgacct gtgccgccag gagtacacca tcgcccgctc     300
caacccgctc atcctcatgc ggcttcagct gcccaagtgt gaggcgctgc ccatgcctga     360
gagccccgac gctgccaac                                                  379
```

<210> SEQ ID NO 14
<211> LENGTH: 75
<212> TYPE: DNA
<213> ORGANISM: Artificial Sequence
<220> FEATURE:
<223> OTHER INFORMATION: Synthetic construct

<400> SEQUENCE: 14

```
agcagcagca ccaccaccac caccaccacc accctgctgc tgctgctgct gctgctgctg      60
ctgctgctgc tgctg                                                       75
```

<210> SEQ ID NO 15
<211> LENGTH: 29
<212> TYPE: RNA
<213> ORGANISM: Artificial Sequence
<220> FEATURE:
<223> OTHER INFORMATION: Synthetic construct

<400> SEQUENCE: 15

```
gguucacgac ugcgaaucca ggaccugga                                        29
```

<210> SEQ ID NO 16
<211> LENGTH: 29
<212> TYPE: RNA
<213> ORGANISM: Artificial Sequence
<220> FEATURE:
<223> OTHER INFORMATION: Synthetic construct

<400> SEQUENCE: 16

```
aagaccauua ccgccacugg cguccuguu                                        29
```

<210> SEQ ID NO 17
<211> LENGTH: 29
<212> TYPE: RNA
<213> ORGANISM: Artificial Sequence
<220> FEATURE:
<223> OTHER INFORMATION: Synthetic construct

<400> SEQUENCE: 17

```
auggauuaca gaggaacggc aagcaccac                                        29
```

<210> SEQ ID NO 18
<211> LENGTH: 29
<212> TYPE: RNA
<213> ORGANISM: Artificial Sequence
<220> FEATURE:
<223> OTHER INFORMATION: Synthetic construct

<400> SEQUENCE: 18

```
aagcagaagg caucugcguc cacaccgca                                        29
```

```
<210> SEQ ID NO 19
<211> LENGTH: 29
<212> TYPE: RNA
<213> ORGANISM: Artificial Sequence
<220> FEATURE:
<223> OTHER INFORMATION: Synthetic construct

<400> SEQUENCE: 19
ccuugagcau gaucuucagc uacuguucc                                             29

<210> SEQ ID NO 20
<211> LENGTH: 5
<212> TYPE: PRT
<213> ORGANISM: Artificial Sequence
<220> FEATURE:
<223> OTHER INFORMATION: Synthetic construct

<400> SEQUENCE: 20

Lys Asp Asp Asp Asp
1               5

<210> SEQ ID NO 21
<211> LENGTH: 15
<212> TYPE: DNA
<213> ORGANISM: Artificial Sequence
<220> FEATURE:
<223> OTHER INFORMATION: Synthetic construct

<400> SEQUENCE: 21
aaagatgatg atgat                                                            15

<210> SEQ ID NO 22
<211> LENGTH: 156
<212> TYPE: DNA
<213> ORGANISM: Artificial Sequence
<220> FEATURE:
<223> OTHER INFORMATION: Synthetic construct

<400> SEQUENCE: 22
agcagcagca ccaccaccac caccaccacc accctgctgc tgctgctgct gctgctgctg           60
ctgctgctgc tgctgaaaga tgatgatgat gaacaaaaac tcatctcaga agaggatctg          120
aatatgcata ccggtcatca tcaccatcac cattga                                    156

<210> SEQ ID NO 23
<211> LENGTH: 7
<212> TYPE: PRT
<213> ORGANISM: Artificial Sequence
<220> FEATURE:
<223> OTHER INFORMATION: Tobacco etch virus protease cleavage tag

<400> SEQUENCE: 23

Gly Gln Phe Tyr Leu Asn Glu
1               5

<210> SEQ ID NO 24
<211> LENGTH: 21
<212> TYPE: DNA
<213> ORGANISM: Artificial Sequence
<220> FEATURE:
<223> OTHER INFORMATION: Tobacco etch virus protease cleavage tag

<400> SEQUENCE: 24
ggccagtttt atctgaacga a                                                     21
```

```
<210> SEQ ID NO 25
<211> LENGTH: 162
<212> TYPE: DNA
<213> ORGANISM: Artificial Sequence
<220> FEATURE:
<223> OTHER INFORMATION: Tobacco etch virus protease cleavage tag

<400> SEQUENCE: 25
agcagcagca ccaccaccac caccaccacc accctgctgc tgctgctgct gctgctgctg      60
ctgctgctgc tgctgggcca gttttatctg aacgaagaac aaaaactcat ctcagaagag     120
gatctgaata tgcataccgg tcatcatcac catcaccatt ga                        162

<210> SEQ ID NO 26
<211> LENGTH: 431
<212> TYPE: PRT
<213> ORGANISM: Artificial Sequence
<220> FEATURE:
<223> OTHER INFORMATION: Synthetic construct

<400> SEQUENCE: 26

Met Ala Arg Gly Ser Ala Leu Pro Arg Arg Pro Leu Leu Cys Ile Pro
1               5                   10                  15

Ala Val Trp Ala Ala Ala Leu Leu Leu Ser Val Ser Arg Thr Ser
            20                  25                  30

Gly Glu Val Glu Val Leu Asp Pro Asn Asp Pro Leu Gly Pro Leu Asp
        35                  40                  45

Gly Gln Asp Gly Pro Ile Pro Thr Leu Lys Gly Tyr Phe Leu Asn Phe
    50                  55                  60

Leu Glu Pro Val Asn Asn Ile Thr Ile Val Gln Gly Gln Thr Ala Ile
65                  70                  75                  80

Leu His Cys Lys Val Ala Gly Asn Pro Pro Pro Asn Val Arg Trp Leu
                85                  90                  95

Lys Asn Asp Ala Pro Val Val Gln Glu Pro Arg Arg Ile Ile Ile Arg
            100                 105                 110

Lys Thr Glu Tyr Gly Ser Arg Leu Arg Ile Gln Asp Leu Asp Thr Thr
        115                 120                 125

Asp Thr Gly Tyr Tyr Gln Cys Val Ala Thr Asn Gly Met Lys Thr Ile
    130                 135                 140

Thr Ala Thr Gly Val Leu Phe Val Arg Leu Gly Pro Thr His Ser Pro
145                 150                 155                 160

Asn His Asn Phe Gln Asp Asp Tyr His Glu Asp Gly Phe Cys Gln Pro
                165                 170                 175

Tyr Arg Gly Ile Ala Cys Ala Arg Phe Ile Gly Asn Arg Thr Ile Tyr
            180                 185                 190

Val Asp Ser Leu Gln Met Gln Gly Glu Ile Glu Asn Arg Ile Thr Ala
        195                 200                 205

Ala Phe Thr Met Ile Gly Thr Ser Thr His Leu Ser Asp Gln Cys Ser
    210                 215                 220

Gln Phe Ala Ile Pro Ser Phe Cys His Phe Val Phe Pro Leu Cys Asp
225                 230                 235                 240

Ala Arg Ser Arg Ala Pro Lys Pro Arg Glu Leu Cys Arg Asp Glu Cys
                245                 250                 255

Glu Val Leu Glu Ser Asp Leu Cys Arg Gln Glu Tyr Thr Ile Ala Arg
            260                 265                 270

Ser Asn Pro Leu Ile Leu Met Arg Leu Gln Leu Pro Lys Cys Glu Ala
        275                 280                 285
```

```
Leu Pro Met Pro Glu Ser Pro Asp Ala Ala Asn Cys Met Arg Ile Gly
        290                 295                 300
Ile Pro Ala Glu Arg Leu Gly Arg Tyr His Gln Cys Tyr Asn Gly Ser
305                 310                 315                 320
Gly Met Asp Tyr Arg Gly Thr Ala Ser Thr Thr Lys Ser Gly His Gln
                325                 330                 335
Cys Gln Pro Trp Ala Leu Gln His Pro His Ser His His Leu Ser Ser
            340                 345                 350
Thr Asp Phe Pro Glu Leu Gly Gly Gly His Ala Tyr Cys Arg Asn Pro
        355                 360                 365
Gly Gly Gln Met Glu Gly Pro Trp Cys Phe Thr Gln Asn Lys Asn Val
    370                 375                 380
Arg Met Glu Leu Cys Asp Val Pro Ser Cys Ser Pro Arg Asp Ser Ser
385                 390                 395                 400
Lys Met Gly Ile Leu Tyr Ser Ser Ser Thr Thr Thr Thr Thr Thr Thr
                405                 410                 415
Thr Leu Leu Leu Leu Leu Leu Leu Leu Leu Leu Leu Leu Leu
        420                 425                 430
```

<210> SEQ ID NO 27
<211> LENGTH: 1374
<212> TYPE: DNA
<213> ORGANISM: Artificial Sequence
<220> FEATURE:
<223> OTHER INFORMATION: Synthetic construct

<400> SEQUENCE: 27

| | | |
|---|---|---|
| atggcccggg gctcggcgct cccgcggcgg ccgctgctgt gcatcccggc cgtctgggcg | 60 |
| gccgccgcgc ttctgctctc agtgtcccgg acttcaggtg aagtggaggt tctggatccg | 120 |
| aacgacccct taggacccct tgatgggcag gacggcccga ttccaactct gaaaggttac | 180 |
| tttctgaatt tctggagcc agtaaacaat atcaccattg tccaaggcca gacggcaatt | 240 |
| ctgcactgca aggtggcagg aaacccaccc cctaacgtgc ggtggctaaa gaatgatgcc | 300 |
| ccggtggtgc aggagccgcg gcggatcatc atccggaaga cagaatatgg ttcacgactg | 360 |
| cgaatccagg acctggacac gacagacact ggctactacc agtgcgtggc caccaacggg | 420 |
| atgaagacca ttaccgccac tggcgtcctg tttgtgcggc tgggtccaac gcacagccca | 480 |
| aatcataact tcaggatga ttaccacgag gatgggttct gccagcctta ccggggaatt | 540 |
| gcctgtgcac gcttcattgg caaccggacc atttatgtgg actcgcttca gatgcagggg | 600 |
| gagattgaaa accgaatcac agcggccttc accatgatcg gcacgtctac gcacctgtcg | 660 |
| gaccagtgct cacagttcgc catcccatcc ttctgccact cgtgtgtttcc tctgtgcgac | 720 |
| gcgcgctccc gggcacccaa gccgcgtgag ctgtgccgcg acgagtgcga ggtgctggag | 780 |
| agcgacctgt gccgccagga gtacaccatc gcccgctcca acccgctcat cctcatgcgg | 840 |
| cttcagctgc ccaagtgtga ggcgctgccc atgcctgaga gccccgacgc tgccaactgc | 900 |
| atgcgcattg gcatcccagc cgagaggctg ggccgctacc atcagtgcta taacggctca | 960 |
| ggcatggatt acagaggaac ggcaagcacc accaagtcag gccaccagtg ccagccgtgg | 1020 |
| gccctgcagc accccacag ccaccacctg tccagcacag acttccctga gcttggaggg | 1080 |
| gggcacgcct actgccggaa ccccggaggc cagatggagg gccctggtg ctttacgcag | 1140 |
| aataaaaacg tacgcatgga actgtgtgac gtaccctcgt gtagtccccg agacagcagc | 1200 |
| aagatgggga ttctgtacag cagcagcacc accaccacca ccaccaccac cctgctgctg | 1260 |

```
ctgctgctgc tgctgctgct gctgctgctg ctgaaagatg atgatgatga acaaaaactc    1320
atctcagaag aggatctgaa tatgcatacc ggtcatcatc accatcacca ttga          1374
```

<210> SEQ ID NO 28
<211> LENGTH: 457
<212> TYPE: PRT
<213> ORGANISM: Artificial Sequence
<220> FEATURE:
<223> OTHER INFORMATION: Synthetic construct

<400> SEQUENCE: 28

```
Met Ala Arg Gly Ser Ala Leu Pro Arg Pro Leu Leu Cys Ile Pro
1               5                   10                  15

Ala Val Trp Ala Ala Ala Leu Leu Leu Ser Val Ser Arg Thr Ser
                20                  25                  30

Gly Glu Val Glu Val Leu Asp Pro Asn Asp Pro Leu Gly Pro Leu Asp
            35                  40                  45

Gly Gln Asp Gly Pro Ile Pro Thr Leu Lys Gly Tyr Phe Leu Asn Phe
    50                  55                  60

Leu Glu Pro Val Asn Asn Ile Thr Ile Val Gln Gly Gln Thr Ala Ile
65                  70                  75                  80

Leu His Cys Lys Val Ala Gly Asn Pro Pro Asn Val Arg Trp Leu
                85                  90                  95

Lys Asn Asp Ala Pro Val Val Gln Glu Pro Arg Arg Ile Ile Ile Arg
                100                 105                 110

Lys Thr Glu Tyr Gly Ser Arg Leu Arg Ile Gln Asp Leu Asp Thr Thr
            115                 120                 125

Asp Thr Gly Tyr Tyr Gln Cys Val Ala Thr Asn Gly Met Lys Thr Ile
    130                 135                 140

Thr Ala Thr Gly Val Leu Phe Val Arg Leu Gly Pro Thr His Ser Pro
145                 150                 155                 160

Asn His Asn Phe Gln Asp Asp Tyr His Glu Asp Gly Phe Cys Gln Pro
                165                 170                 175

Tyr Arg Gly Ile Ala Cys Ala Arg Phe Ile Gly Asn Arg Thr Ile Tyr
            180                 185                 190

Val Asp Ser Leu Gln Met Gln Gly Glu Ile Glu Asn Arg Ile Thr Ala
    195                 200                 205

Ala Phe Thr Met Ile Gly Thr Ser Thr His Leu Ser Asp Gln Cys Ser
210                 215                 220

Gln Phe Ala Ile Pro Ser Phe Cys His Phe Val Phe Pro Leu Cys Asp
225                 230                 235                 240

Ala Arg Ser Arg Ala Pro Lys Pro Arg Glu Leu Cys Arg Asp Glu Cys
                245                 250                 255

Glu Val Leu Glu Ser Asp Leu Cys Arg Gln Glu Tyr Thr Ile Ala Arg
            260                 265                 270

Ser Asn Pro Leu Ile Leu Met Arg Leu Gln Leu Pro Lys Cys Glu Ala
    275                 280                 285

Leu Pro Met Pro Glu Ser Pro Asp Ala Ala Asn Cys Met Arg Ile Gly
290                 295                 300

Ile Pro Ala Glu Arg Leu Gly Arg Tyr His Gln Cys Tyr Asn Gly Ser
305                 310                 315                 320

Gly Met Asp Tyr Arg Gly Thr Ala Ser Thr Thr Lys Ser Gly His Gln
                325                 330                 335

Cys Gln Pro Trp Ala Leu Gln His Pro His Ser His Leu Ser Ser
            340                 345                 350
```

```
Thr Asp Phe Pro Glu Leu Gly Gly His Ala Tyr Cys Arg Asn Pro
        355                 360                 365

Gly Gly Gln Met Glu Gly Pro Trp Cys Phe Thr Gln Asn Lys Asn Val
    370                 375                 380

Arg Met Glu Leu Cys Asp Val Pro Ser Cys Ser Pro Arg Asp Ser Ser
385                 390                 395                 400

Lys Met Gly Ile Leu Tyr Ser Ser Ser Thr Thr Thr Thr Thr Thr Thr
                405                 410                 415

Thr Leu Leu Leu Leu Leu Leu Leu Leu Leu Leu Leu Leu Leu Leu Lys
                420                 425                 430

Asp Asp Asp Glu Gln Lys Leu Ile Ser Glu Glu Asp Leu Asn Met
            435                 440                 445

His Thr Gly His His His His His His
    450                 455
```

<210> SEQ ID NO 29
<211> LENGTH: 1374
<212> TYPE: DNA
<213> ORGANISM: Artificial Sequence
<220> FEATURE:
<223> OTHER INFORMATION: Synthetic construct

<400> SEQUENCE: 29

```
atggcccggg gctcggcgct cccgcggcgg ccgctgctgt gcatcccggc cgtctgggcg      60
gccgccgcgc ttctgctctc agtgtcccgg acttcaggtg aagtggaggt tctggatccg     120
aacgacccct taggacccct tgatgggcag acggcccga ttccaactct gaaaggttac     180
tttctgaatt ttctggagcc agtaaacaat atcaccattg tccaaggcca gacggcaatt     240
ctgcactgca aggtggcagg aaacccaccc cctaacgtgc ggtggctaaa gaatgatgcc     300
ccggtggtgc aggagccgcg gcggatcatc atccggaaga cagaatatgg ttcacgactg     360
cgaatccagg acctggacac gacagacact ggctactacc agtgcgtggc caccaacggg     420
atgaagacca ttaccgccac tggcgtcctg tttgtgcggc tgggtccaac gcacagccca     480
aatcataact tcaggatga ttaccacgag gatggttct gccagcctta ccggggaatt     540
gcctgtgcac gcttcattgg caaccggacc atttatgtgg actcgcttca gatgcagggg     600
gagattgaaa accgaatcac agcggccttc accatgatcg gcacgtctac gcacctgtcg     660
gaccagtgct cacagttcgc catcccatcc ttctgccact tcgtgtttcc tctgtgcgac     720
gcgcgctccc gggcacccaa gccgcgtgag ctgtgccgcg acgagtgcga ggtgctggag     780
agcgacctgt gccgccagga gtacaccatc gcccgctcca acccgctcat cctcatgcgg     840
cttcagctgc ccaagtgtga ggcgctgccc atgcctgaga gccccgacgc tgccaactgc     900
atgcgcattg gcatcccagc cgagaggctg ggccgctacc atcagtgcta acggctca     960 ggcatggatt acagaggaac ggcaagcacc accaagtcag gccaccagtg ccagccgtgg    1020
gccctgcagc accccacag ccaccacctg tccagcacag acttccctga gcttggaggg    1080
gggcacgcct actgccggaa ccccggaggc cagatggagg gcccctggtg ctttacgcag    1140
aataaaaacg tacgcatgga actgtgtgac gtaccctcgt gtagtcccg agacagcagc    1200 aagatgggga ttctgtacag cagcagcacc accaccacca ccaccaccac cctgctgctg    1260
ctgctgctgc tgctgctgct gctgctgctg ctgaaagatg atgatgatga acaaaaactc    1320
atctcagaag aggatctgaa tatgcatacc ggtcatcatc accatcacca ttga          1374
```

```
<210> SEQ ID NO 30
<211> LENGTH: 459
<212> TYPE: PRT
<213> ORGANISM: Artificial Sequence
<220> FEATURE:
<223> OTHER INFORMATION: Synthetic construct

<400> SEQUENCE: 30

Met Ala Arg Gly Ser Ala Leu Pro Arg Pro Leu Leu Cys Ile Pro
1               5                   10                  15

Ala Val Trp Ala Ala Ala Leu Leu Leu Ser Val Ser Arg Thr Ser
                20                  25                  30

Gly Glu Val Glu Val Leu Asp Pro Asn Asp Pro Leu Gly Pro Leu Asp
            35                  40                  45

Gly Gln Asp Gly Pro Ile Pro Thr Leu Lys Gly Tyr Phe Leu Asn Phe
50                  55                  60

Leu Glu Pro Val Asn Asn Ile Thr Ile Val Gln Gly Gln Thr Ala Ile
65                  70                  75                  80

Leu His Cys Lys Val Ala Gly Asn Pro Pro Asn Val Arg Trp Leu
                85                  90                  95

Lys Asn Asp Ala Pro Val Val Gln Glu Pro Arg Arg Ile Ile Ile Arg
                100                 105                 110

Lys Thr Glu Tyr Gly Ser Arg Leu Arg Ile Gln Asp Leu Asp Thr Thr
            115                 120                 125

Asp Thr Gly Tyr Tyr Gln Cys Val Ala Thr Asn Gly Met Lys Thr Ile
            130                 135                 140

Thr Ala Thr Gly Val Leu Phe Val Arg Leu Gly Pro Thr His Ser Pro
145                 150                 155                 160

Asn His Asn Phe Gln Asp Asp Tyr His Glu Asp Gly Phe Cys Gln Pro
                165                 170                 175

Tyr Arg Gly Ile Ala Cys Ala Arg Phe Ile Gly Asn Arg Thr Ile Tyr
            180                 185                 190

Val Asp Ser Leu Gln Met Gln Gly Glu Ile Glu Asn Arg Ile Thr Ala
            195                 200                 205

Ala Phe Thr Met Ile Gly Thr Ser Thr His Leu Ser Asp Gln Cys Ser
210                 215                 220

Gln Phe Ala Ile Pro Ser Phe Cys His Phe Val Phe Pro Leu Cys Asp
225                 230                 235                 240

Ala Arg Ser Arg Ala Pro Lys Pro Arg Glu Leu Cys Arg Asp Glu Cys
                245                 250                 255

Glu Val Leu Glu Ser Asp Leu Cys Arg Gln Glu Tyr Thr Ile Ala Arg
            260                 265                 270

Ser Asn Pro Leu Ile Leu Met Arg Leu Gln Leu Pro Lys Cys Glu Ala
            275                 280                 285

Leu Pro Met Pro Glu Ser Pro Asp Ala Ala Asn Cys Met Arg Ile Gly
290                 295                 300

Ile Pro Ala Glu Arg Leu Gly Arg Tyr His Gln Cys Tyr Asn Gly Ser
305                 310                 315                 320

Gly Met Asp Tyr Arg Gly Thr Ala Ser Thr Thr Lys Ser Gly His Gln
                325                 330                 335

Cys Gln Pro Trp Ala Leu Gln His Pro His Ser His His Leu Ser Ser
            340                 345                 350

Thr Asp Phe Pro Glu Leu Gly Gly Gly His Ala Tyr Cys Arg Asn Pro
            355                 360                 365

Gly Gly Gln Met Glu Gly Pro Trp Cys Phe Thr Gln Asn Lys Asn Val
```

```
           370                 375                 380
Arg Met Glu Leu Cys Asp Val Pro Ser Cys Ser Pro Arg Asp Ser Ser
385                 390                 395                 400

Lys Met Gly Ile Leu Tyr Ser Ser Ser Thr Thr Thr Thr Thr Thr Thr
                405                 410                 415

Thr Leu Leu Leu Leu Leu Leu Leu Leu Leu Leu Leu Leu Leu Leu Gly
            420                 425                 430

Gln Phe Tyr Leu Asn Glu Gln Lys Leu Ile Ser Glu Glu Asp Leu
            435                 440                 445

Asn Met His Thr Gly His His His His His His
        450                 455
```

<210> SEQ ID NO 31
<211> LENGTH: 1380
<212> TYPE: DNA
<213> ORGANISM: Artificial Sequence
<220> FEATURE:
<223> OTHER INFORMATION: Synthetic construct

<400> SEQUENCE: 31

```
atggcccggg gctcggcgct cccgcggcgg ccgctgctgt gcatcccggc cgtctgggcg      60
gccgccgcgc ttctgctctc agtgtcccgg acttcaggtg aagtggaggt tctggatccg     120
aacgacccct taggacccct tgatgggcag gacggcccga ttccaactct gaaaggttac     180
tttctgaatt tctggagcc agtaaacaat atcaccattg tccaaggcca gacggcaatt     240
ctgcactgca aggtggcagg aaacccaccc cctaacgtgc ggtggctaaa gaatgatgcc     300
ccggtggtgc aggagccgcg gcggatcatc atccggaaga cagaatatgg ttcacgactg     360
cgaatccagg acctggacac gacagacact ggctactacc agtgcgtggc caccaacggg     420
atgaagacca ttaccgccac tggcgtcctg tttgtgcggc tgggtccaac gcacagccca     480
aatcataact tcaggatga ttaccacgag gatgggttct gccagcctta ccggggaatt     540
gcctgtgcac gcttcattgg caaccggacc atttatgtgg actcgcttca gatgcagggg     600
gagattgaaa accgaatcac agcggccttc accatgatcg gcacgtctac gcacctgtcg     660
gaccagtgct cacagttcgc catcccatcc ttctgccact cgtgtttcc tctgtgcgac     720
gcgcgctccc gggcacccaa gccgcgtgag ctgtgccgcg acgagtgcga ggtgctggag     780
agcgacctgt gccgccagga gtacaccatc gcccgctcca acccgctcat cctcatgcgg     840
cttcagctgc caagtgtga ggcgctgccc atgcctgaga ccccgacgc tgccaactgc     900
atgcgcattg catcccagc cgagaggctg ggccgctacc atcagtgcta taacggctca     960
ggcatggatt acagaggaac ggcaagcacc accaagtcag ccaccagtg ccagccgtgg    1020
gccctgcagc accccacag ccaccacctg tccagcacag acttccctga gcttggaggg    1080
gggcacgcct actgccggaa ccccggaggc cagatggagg gcccctggtg ctttacgcag    1140
aataaaaacg tacgcatgga actgtgtgac gtaccctcgt gtagtccccg agacagcagc    1200
aagatgggga ttctgtacag cagcagcacc accaccacca ccaccaccac cctgctgctg    1260
ctgctgctgc tgctgctgct gctgctgctg ctgggccagt tttatctgaa cgaagaacaa    1320
aaactcatct cagaagagga tctgaatatg cataccggtc atcatcacca tcaccattga    1380
```

The invention claimed is:
1. A receptor tyrosine kinase-like orphan receptor 2 (ROR2) inhibitor that is an siRNA which comprises a nucleotide sequence selected from the group consisting of:
   (i) 5' AAGUCUACAAAGGUCACCUGU 3' (SEQ ID NO: 1), a fragment comprising at least 10 contiguous nucleotides of SEQ ID NO:1, and variants thereof having up to three nucleotide substitutions;
   (ii) 5' AAGUCUACAAAGGUCACCUGUCCUGUCUC 3' (SEQ ID NO: 2) a fragment comprising at least 10 contiguous nucleotides of SEQ ID NO: 2, and variants thereof having up to three nucleotide substitutions;
   (iii) 5' AAACAGGUGACCUUUGUAGAC 3' (SEQ ID NO: 3), a fragment comprising at least 10 contiguous nucleotides of SEQ ID NO: 3, and variants thereof having up to three nucleotide substitutions; and
   (iv) 5' AAACAGGUGACCUGUAGACCCUGUCUC 3' (SEQ ID NO: 4), a fragment comprising at least 10 contiguous nucleotides of SEQ ID NO: 4, and variants thereof having up to three nucleotide substitutions.

* * * * *